United States Patent
Blazar et al.

(10) Patent No.: US 10,993,959 B2
(45) Date of Patent: May 4, 2021

(54) METHODS AND COMPOSITIONS FOR INCREASING THE SUPPRESSIVE FUNCTION OF REGULATORY T-CELLS (TREGS)

(71) Applicants: Regents of the University of Minnesota, Minneapolis, MN (US); New York University, New York, NY (US)

(72) Inventors: Bruce R. Blazar, Golden Valley, MN (US); Cameron McDonald-Hyman, St. Paul, MN (US); Michael Dustin, New York, NY (US); Sudha Kumari, New York, NY (US); Tom Neubert, New York, NY (US); James Muller, New York, NY (US); Keli Hippen, Minneapolis, MN (US)

(73) Assignees: Regents of the University of Minnesota, Minneapolis, MN (US); New York University, New York, NY (US)

( * ) Notice: Subject to any disclaimer, the term of this patent is extended or adjusted under 35 U.S.C. 154(b) by 134 days.

(21) Appl. No.: 15/757,516

(22) PCT Filed: Sep. 2, 2016

(86) PCT No.: PCT/US2016/050215
§ 371 (c)(1),
(2) Date: Mar. 5, 2018

(87) PCT Pub. No.: WO2017/041002
PCT Pub. Date: Mar. 9, 2017

(65) Prior Publication Data
US 2019/0022125 A1    Jan. 24, 2019

Related U.S. Application Data

(60) Provisional application No. 62/214,680, filed on Sep. 4, 2015.

(51) Int. Cl.
*A61K 48/00* (2006.01)
*C12N 15/11* (2006.01)
(Continued)

(52) U.S. Cl.
CPC .......... *A61K 31/7105* (2013.01); *A61K 35/17* (2013.01); *A61P 35/00* (2018.01);
(Continued)

(58) Field of Classification Search
CPC .... A61K 31/7105; A61K 35/00; A61K 35/17; C12N 15/1137; C12N 15/1138; C12N 5/0637
See application file for complete search history.

(56) References Cited

U.S. PATENT DOCUMENTS 4,683,195 A    7/1987   Mullis et al.
4,683,202 A    7/1987   Mullis
(Continued)

OTHER PUBLICATIONS

Ex Vivo—downloaded from https://en.wikipedia.org/wiki/Ex_vivo on May 18, 2020.*

(Continued)

*Primary Examiner* — Terra C Gibbs
(74) *Attorney, Agent, or Firm* — Fish & Richardson P.C.

(57) ABSTRACT

Methods and compositions for increasing the suppressive function of regulatory T-cells (Tregs) are provided.

16 Claims, 15 Drawing Sheets

Specification includes a Sequence Listing.

(51) Int. Cl.
*C07H 21/02* (2006.01)
*C07H 21/04* (2006.01)
*A61K 31/7105* (2006.01)
*C12N 15/113* (2010.01)
*A61P 35/00* (2006.01)
*A61K 35/17* (2015.01)
*C12N 5/0783* (2010.01)

(52) U.S. Cl.
CPC ........ *C12N 5/0637* (2013.01); *C12N 15/1137* (2013.01); *C12N 15/1138* (2013.01); *C12N 2310/14* (2013.01)

(56) References Cited

U.S. PATENT DOCUMENTS

| | | |
|---|---|---|
| 4,800,159 A | 1/1989 | Mullis et al. |
| 4,965,188 A | 10/1990 | Mullis et al. |
| 2011/0142814 A1 | 6/2011 | Zanin-Zhorov et al. |
| 2012/0196919 A1 | 8/2012 | Brown et al. |

OTHER PUBLICATIONS

In situ—downloaded from https://en.wikipedia.org/wiki/In_situ on May 18, 2020.*

Intermediate Filament—downlaoded from https://en.wikipedia.org/wiki/Intermediate_filament on May 18, 2020.*

Ivaska et al. (The EMBO Journal, 2005 vol. 24:3834-3845).*

Billadeau et al., "Regulation of T-cell activation by the cytoskeleton," Nat. Rev. Immunol., 7(2):131-143, Feb. 2007.

Chenna et al., "Multiple sequence alignment with the Clustal series of programs," Nucleic. Acids. Res., 31(13):3497-500, Jul. 2003.

Liang et al., "The lymphoid lineage-specific actin-uncapping protein Rltpr is essential for costimulation via CD28 and the development of regulatory T cells," Nat. Immunol., 14(8):858-866, Aug. 2013.

Liang, "Distinct roles for CARMIL isoforms in cell migration," Mol. Biol. Cell., 20(24):5290-305, Dec. 2009.

Liang, "The lymphoid lineage-specific actin-uncapping protein Rltpr is essential for costimulation via CD28 and the development of regulatory T cells," Nat. Immunol., 14(8):858-66, Aug. 2013.

McDonald-Hyman et al., "Protein Kinase C-Theta Interacts with mTORC2 and Vimentin to Limit Regulatory T-Cell Function," Blood, 126:849, 2015.

Smith et al., "Total silencing by intron-spliced hairpin RNAs," Nature, 407(6802):319-20, Sep. 2000.

Wesley et al., "Construct design for efficient, effective and high-throughput gene silencing in plants," The Plant J., 27(6):581-90, Sep. 2001.

* cited by examiner

PANELS A-E

METHODS AND COMPOSITIONS FOR INCREASING THE SUPPRESSIVE FUNCTION OF REGULATORY T-CELLS (TREGS)

CROSS-REFERENCE TO RELATED APPLICATIONS

This application is a National Stage application under 35 U.S.C. § 317 of International Application No. PCT/US2016/050215, having an International Filing Date of Sep. 2, 2016, which claims the benefit of priority under 35 U.S.C. § 119(e) to U.S. Provisional Application Ser. No. 62/214,680, filed Sep. 4, 2015, the disclosures of which are incorporated herein by reference in their entirety.

FEDERALLY SPONSORED RESEARCH OR DEVELOPMENT

This invention was made with government support under HL11879 awarded by National Institutes of Health. The government has certain rights in the invention.

TECHNICAL FIELD

This disclosure generally relates to T-cells and methods of engineering T-cells to reduce or eliminate graft-vs.-host-disease.

BACKGROUND

Regulatory T-cells (Tregs) play a critical role in preventing and treating autoimmune and alloimmune reactions, including graft-versus-host disease (GVHD) and solid organ transplant rejection, allergies and responses to foreign antigens (e.g., microbes, protein replacement therapy for deficiency disorders). Two recent clinical trials demonstrated that, in patients undergoing hematopoietic stem cell transplantation, adoptive transfer of Tregs significantly reduced the incidence of grades II-IV GVHD. While Tregs significantly reduced GVHD severity, they did not eliminate GVHD. One potential way to augment Treg-mediated inhibition of GVHD is to increase Treg suppressive potency. It was previously shown that Treg-specific inhibition of protein kinase C-theta (PKC-θ) enhances Treg function. However, it is unclear whether PKC-θ inhibition can boost Treg function in a systemic inflammatory condition like GVHD. Furthermore, the mechanism by which PKC-θ inhibition augments Treg function is unknown.

SUMMARY

In one aspect, a method of reducing or eliminating the vimentin protein and/or the RLTPR protein and/or the PKC-θ protein in Treg cells in provided. Such a method typically includes contacting the Treg cells with a vimentin-specific and/or a RLTPR-specific and/or a PKC-θ-specific inhibitory nucleic acid molecule.

In some embodiments, the vimentin-specific inhibitory nucleic acid molecule is complementary to at least a portion of the sequence shown in SEQ ID NO: 1. In some embodiments, the RLTPR-specific inhibitor nucleic acid is complementary to at least a portion of the sequence shown in SEQ ID NO: 5. In some embodiments, the PKC-θ-specific inhibitory nucleic acid molecule is complementary to at least a portion of the sequence shown in SEQ ID NO: 9. Representative vimentin-specific inhibitory nucleic acid molecules have the sequence shown in SEQ ID NO: 13, 14, 15 or 16.

In some embodiments, the vimentin-specific and/or the RLTPR-specific and/or the PKC-θ-specific inhibitory nucleic acid molecule is a RNAi nucleic acid molecule. In some embodiments, the vimentin-specific and/or the RLTPR-specific and/or the PKC-θ-specific inhibitory nucleic acid molecule is an antisense nucleic acid molecule. In some embodiments, the vimentin-specific and/or the RLTPR-specific and/or the PKC-θ-specific inhibitor nucleic acid molecule is a siRNA nucleic acid molecule.

In some embodiments, the Treg cells are contacted in vitro. In some embodiments, the Treg cells are contacted in situ. In some embodiments, the Treg cells are contacted in vivo in an individual who has received or is receiving a bone marrow transplant.

In some embodiments, the Treg cells exhibit a phenotype of at least one of the following: reduced PKC-θ auto-phosphorylation at Ser676; improved ability to suppress CD4+ and CD8+ Tcon proliferation; increased surface expression of Nrp1; increased surface expression of Lag3; increased basal and maximal oxygen consumption rate (OCR); increased BoDipy$_{C1-C2}$ uptake; increased expression of CD71; increased expression of CD98; increased expression of CPT1a; or reduced activity of mTORC2, compared to Tregs that lack the vimentin-specific and/or the RLTPR-specific and/or the PKC-θ-specific inhibitory nucleic acid molecule, respectively.

In another aspect, a method of increasing or augmenting the suppressor cell potency of Treg cells is provided. Typically, such a method includes reducing or eliminating vimentin and/or RLTPR and/or PKC-θ in the Treg cells.

In some embodiments, reducing or eliminating the vimentin and/or the RLTPR and/or the PKC-θ in the Treg cells comprising contacting the Treg cells with a moiety selected from the group consisting of a nucleic acid, a nuclease, an antibody, a ligand, a peptide, a drug, a chemical, or a small molecule. Representative nucleic acids include, without limitation, a vimentin-specific and/or a RLTPR-specific and/or a PKC-θ-specific inhibitory nucleic acid molecule. In some embodiments, the vimentin-specific and/or the RLTPR-specific and/or the PCK-θ-specific inhibitory nucleic acid molecule is selected from the group consisting of a RNAi nucleic acid molecule, an antisense nucleic acid molecule, and a siRNA nucleic acid molecule.

In some embodiments, the vimentin-specific inhibitory nucleic acid molecule is complementary to at least a portion of the sequence shown in SEQ ID NO: 1. In some embodiments, the RLTPR-specific inhibitory nucleic acid molecule is complementary to at least a portion of the sequence shown in SEQ ID NO: 5. In some embodiments, the PKC-θ-specific inhibitory nucleic acid molecule is complementary to at least a portion of the sequence shown in SEQ ID NO: 9.

In some embodiments, the method is performed in vitro. In some embodiments, the method is performed in situ. In some embodiments, the method is performed on an individual who has received or is receiving a bone marrow transplant.

In some embodiments, the Treg cells in which the vimentin, and/or RLTPR and/or PCK-θ has been reduced or eliminated exhibit a phenotype of at least one of the following: reduced PKC-θ auto-phosphorylation at Ser676; improved ability to suppress CD4+ and CD8+ Tcon proliferation; increased surface expression of Nrp1; increased surface expression of Lag3; increased basal and maximal oxygen consumption rate (OCR); increased BoDipy$_{C1-C12}$ uptake; increased expression of CD71; increased expression of CD98; increased expression of CPT1a; or reduced activity of mTORC2, compared to Tregs in which vimentin, RLTPR and/or PCK-θ, respectively, is not reduced or eliminated.

In still another aspect, a method of disrupting the structural integrity or the metabolic activity of Treg cells is provided. Typically, such a method includes reducing or eliminating vimentin and/or RLTPR and/or PKC-θ in the Treg cells.

In yet another aspect, a method of screening for compounds that increasing or augmenting the suppressor cell potency of Treg cells is provided. Typically, such a method includes contacting Treg cells with a test compound and determining whether or not the structural integrity or metabolic activity of the cell is disrupted. Disruption of the structural integrity or metabolic activity of the cell can be determined, for example, by detecting a reduction or elimination of vimentin and/or RLTPR and/or PKC-θ in the Treg cells. A test compound that disrupts the structural integrity or metabolic activity of the cell is indicative of a compound that increases or augments the suppressor cell potency of Treg cells.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

Panel A shows acute GVHD. Lethally irradiated BALB/c mice were given 10e6 C57BL/6 bone marrow only (BM), or BM with 2e6 CD4+25−/CD8+25− Tcon cells without (BM+T) or with 1e6 Tregs treated with either DMSO (DMSO) or 10 µM AEB071 (AEB071) for 30 minutes. Compared to DMSO, Tregs treated with AEB071 significantly increased recipient survival (p=0.0036).

Panel B shows Treg activation. Tregs were treated with DMSO or AEB071 as above, and activated overnight with plate bound anti-CD3/28 and IL-2. AEB071 treatment significantly increased the surface expression of Neuropilin-1.

Panel C shows Treg activation. Tregs were treated with DMSO or AEB071 as above, and activated overnight with plate bound anti-CD3/28 and IL-2. AEB071 treatment significantly increased the surface expression of Lymphocyte activation gene 3 (Lag3).

Panel D shows Treg metabolic activity. Tregs were treated with DMSO or AEB071 and activated as above. Oxygen consumption rate (OCR) analysis revealed that AEB071 treatment significantly increased baseline Treg OCR (time 0-19 min) and maximal OCR (time=53-70 min).

Panel E shows Treg suppression. Tregs were transfected with vimentin siRNA (vim) or control (GFP), and activated for 36 hours. CFSE-labeled Tcon were mixed with T-cell depleted splenocytes and soluble anti-CD3 mAb. Treg:Tcon ratios of 1:1-1:27 were plated and CFSE dilution assessed after 3 days.

Figure 2A:
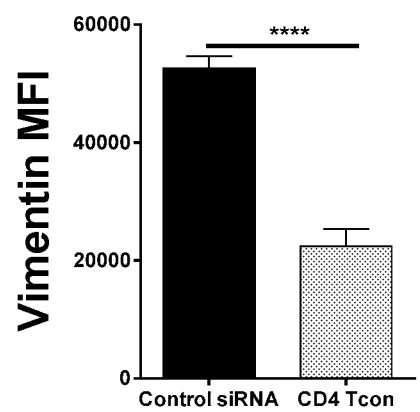

FIG. 2A shows that vimentin is highly enriched in Tregs compared to conventional CD4+ T-cells (CD4 Tcon).

Figure 2B:
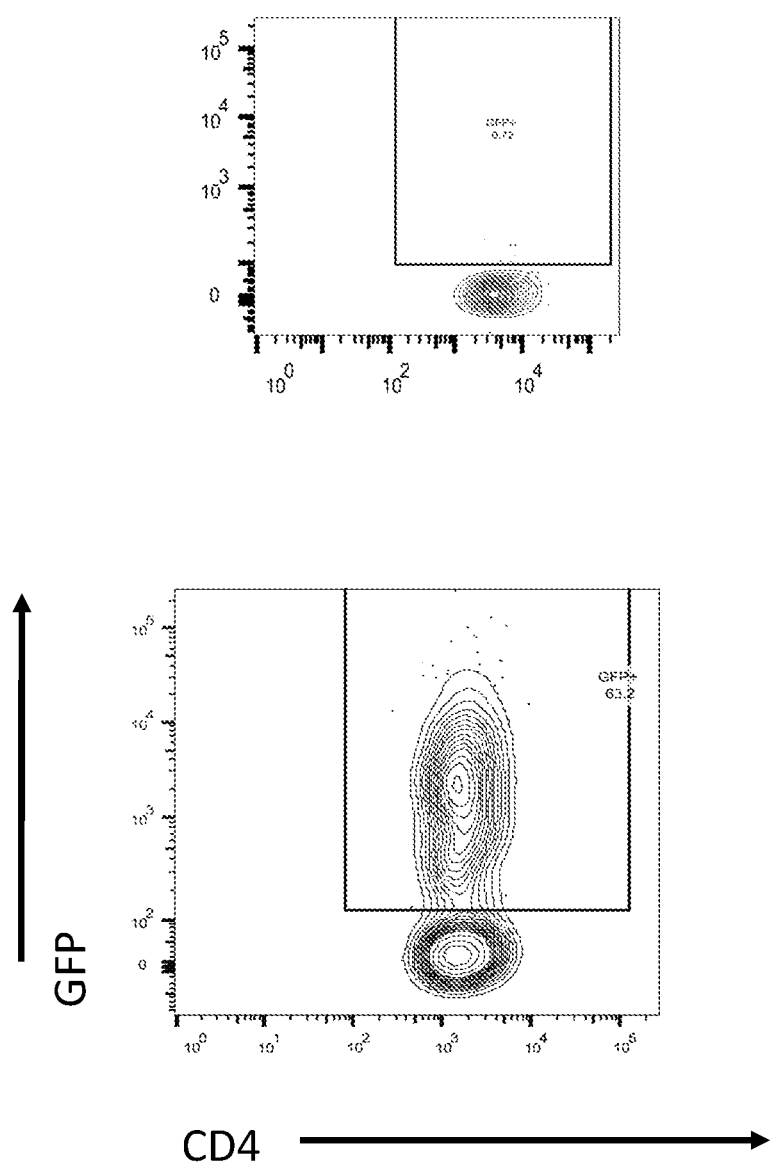

FIG. 2B shows that, compared to the transfection control (top panel), transfection with GFP-siRNA using the transfection protocol described herein yielded 50-60% or greater transfection of Tregs.

Figure 2C:
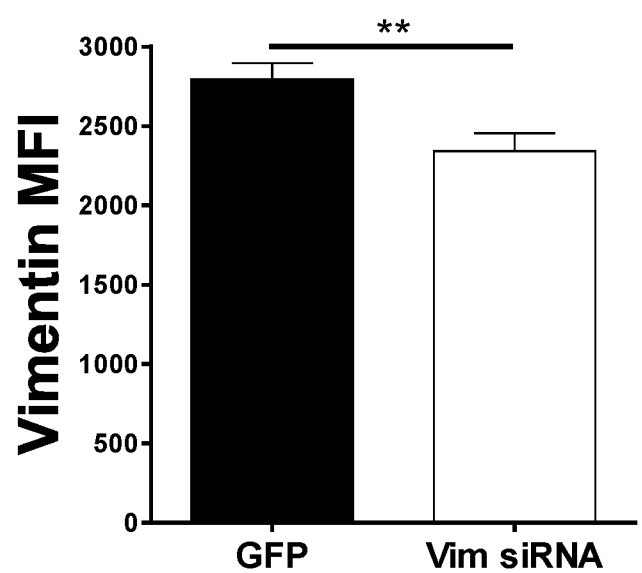

FIG. 2C shows that, compared to the control GFP-siRNA (GFP), when utilizing vimentin siRNA (vim siRNA) and the transfection protocol described herein, vimentin levels were knocked down by 15-30%.

Figure 3A:
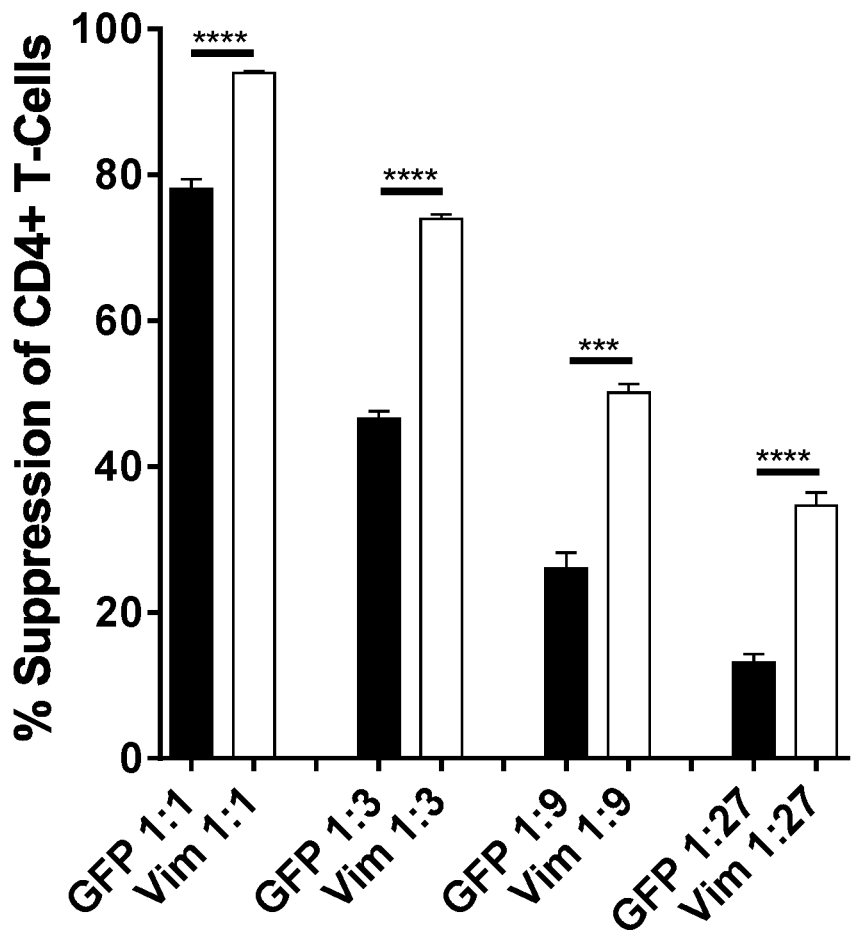

FIG. 3A shows that, in standard in vitro suppression assays, vimentin siRNA-transfected Tregs (Vim) were able to suppress proliferation of CD4 conventional T-cells significantly better than control GFP-siRNA transfected Tregs (GFP). Treg:Tcon ratios of 1:1-1:27 are represented with 1:1, 1:3 etc. denotations in the x-axis labels.

Figure 3B:
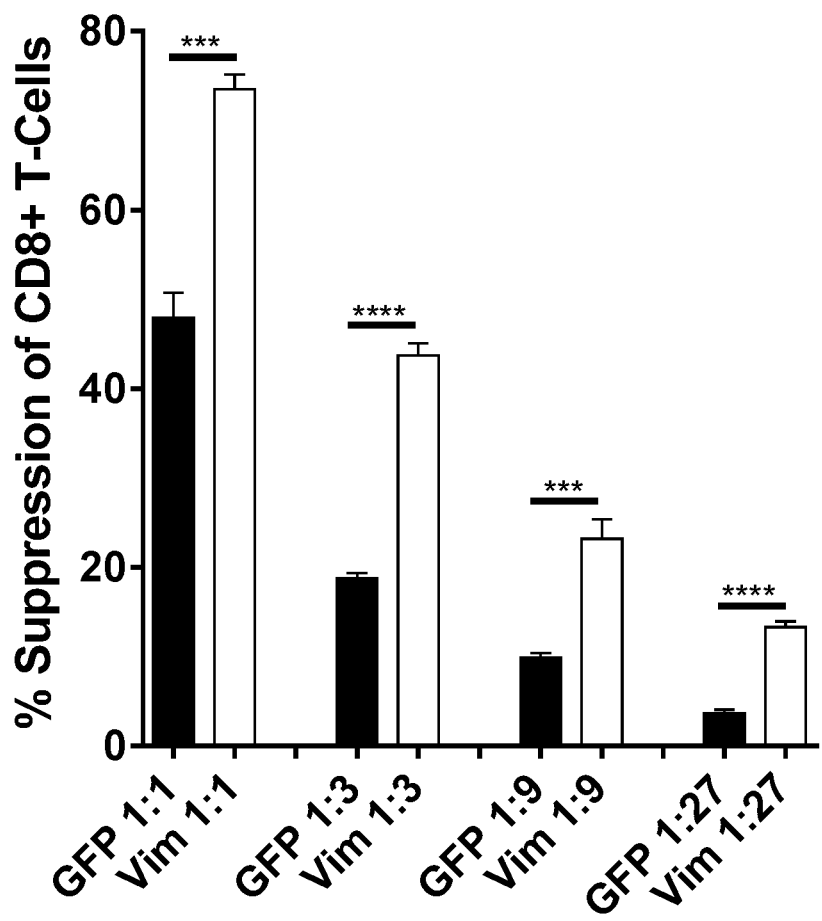

FIG. 3B shows that, in standard in vitro suppression assays, vimentin siRNA-transfected Tregs (Vim) were able to suppress proliferation of CD8 conventional T-cells significantly better than control GFP-siRNA transfected Tregs (GFP). Treg:Tcon ratios of 1:1-1:27 are represented with 1:1, 1:3 etc. denotations in the x-axis labels.

Figure 4A:
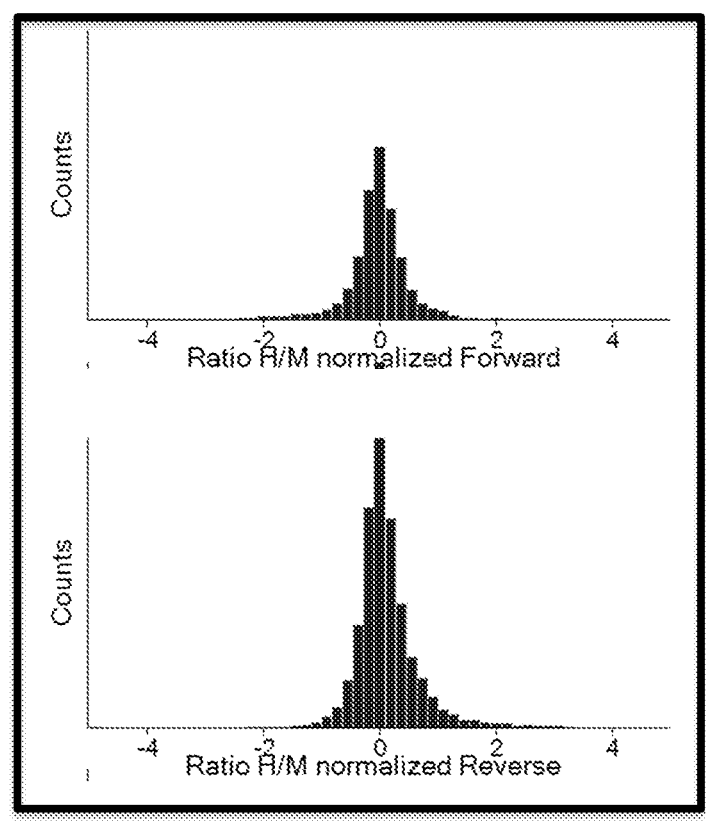

FIG. 4A are histograms showing a symmetrical distribution of the labeling of the samples.

Figure 4B:
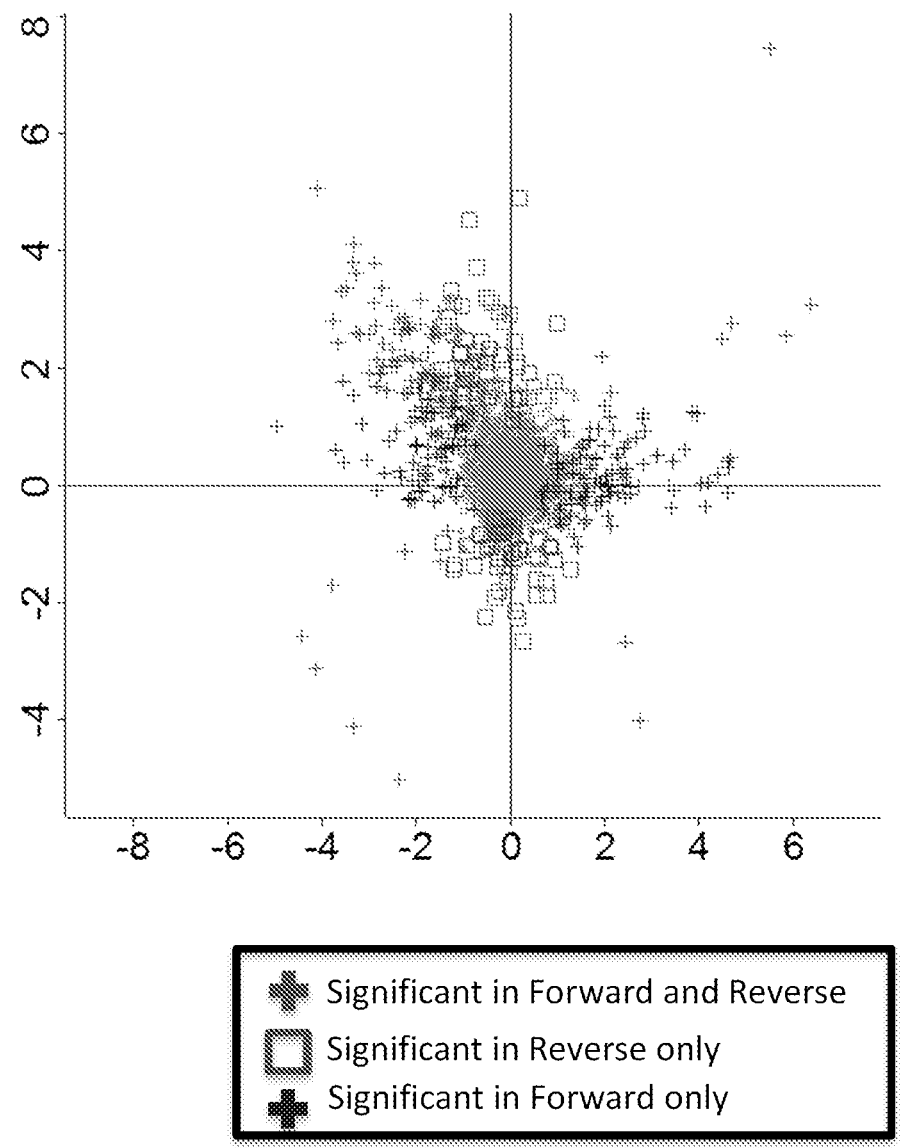

FIG. 4B is a scatter plot showing the consistency between labeled samples.

Figure 5:
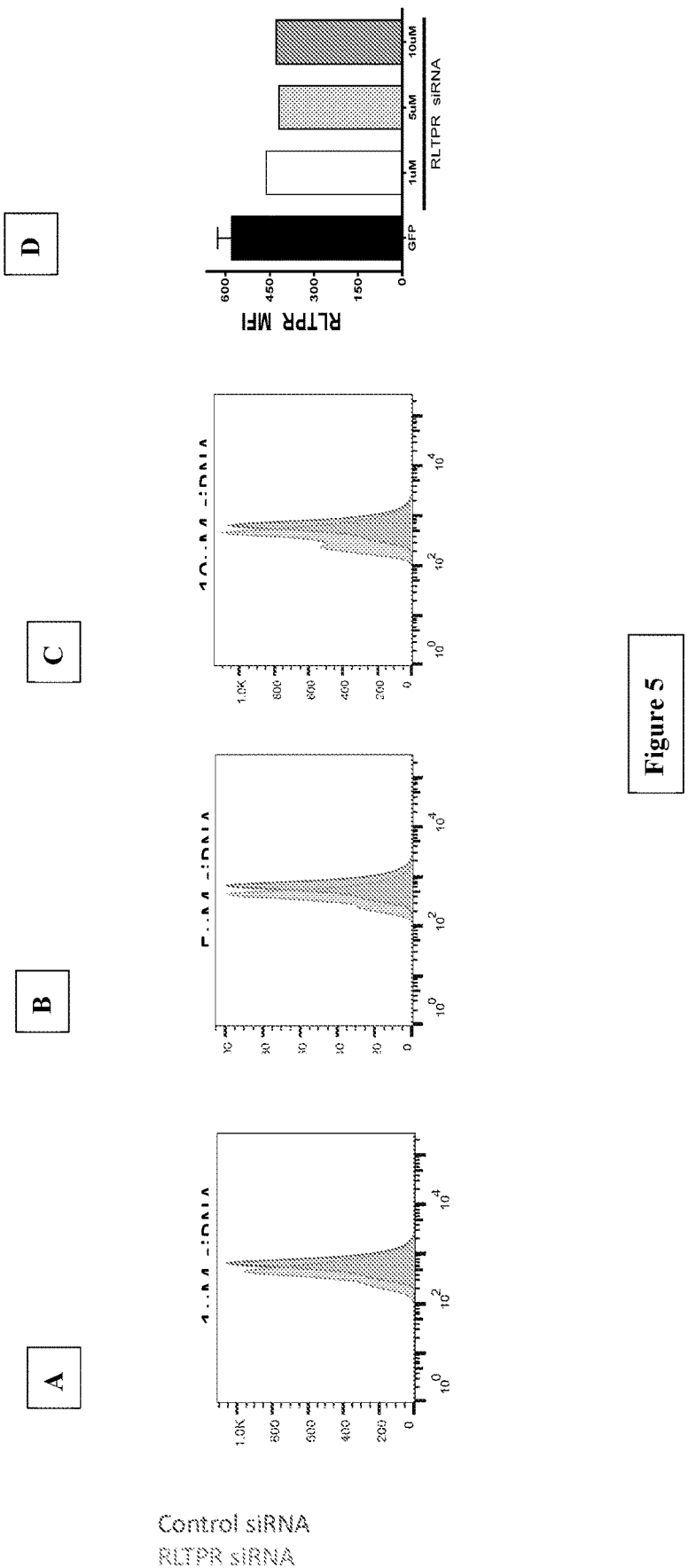

FIG. 5, Panels A-D, show that RLTPR siRNA significantly decreased the amount of RLTPR protein in Treg cells.

Figure 6A:
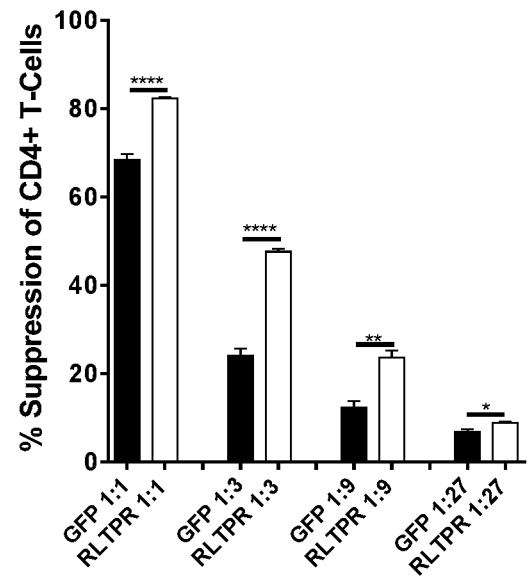

FIG. 6A is a graph showing that RLTPR siRNA increased suppression of CD4+ T-cells in vitro.

Figure 6B:
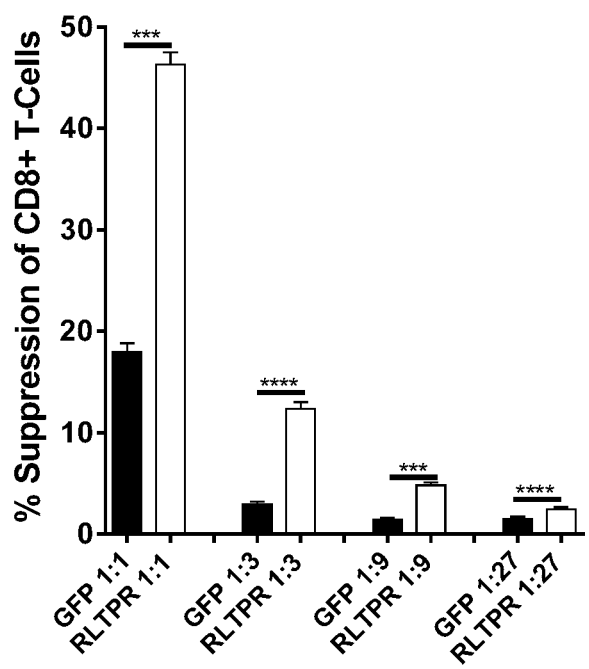

FIG. 6B is a graph showing that RLTPR siRNA increased suppression of CD8+ T-cells in vitro.

Figure 7A:
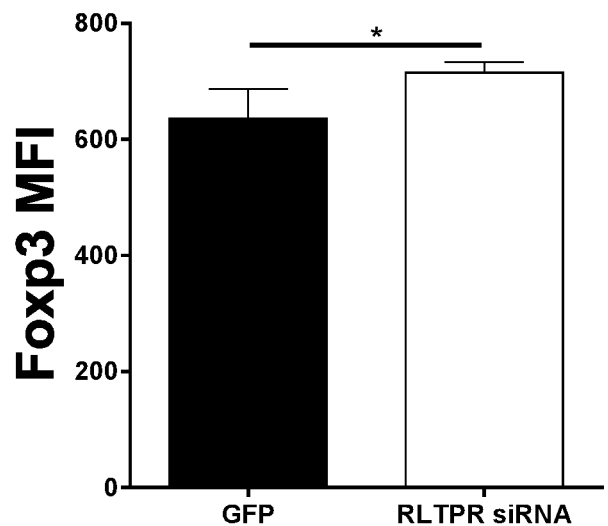

FIG. 7A is a graph showing that RLTPR siRNA resulted in a significant increase in the expression of Foxp3 in Treg cells in vitro ($p<0.05$).

Figure 7B:
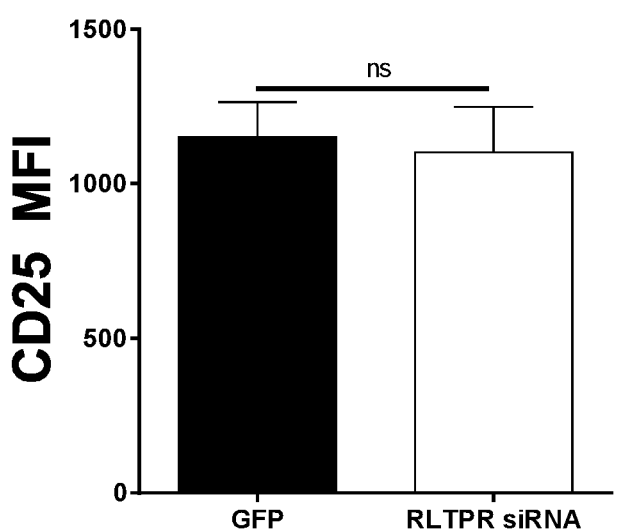

FIG. 7B is a graph showing that RLTPR siRNA had no significant effect on the expression of CD25 in Treg cells in vitro.

Figure 7C:
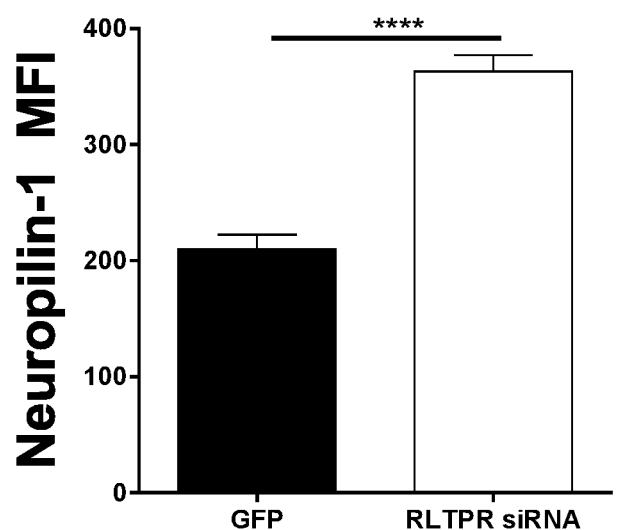

FIG. 7C is a graph showing that RLTPR siRNA significantly increased the expression of neuropilin-1 (Nrp1) in Treg cells in vitro ($p<0.0001$).

Figure 8:
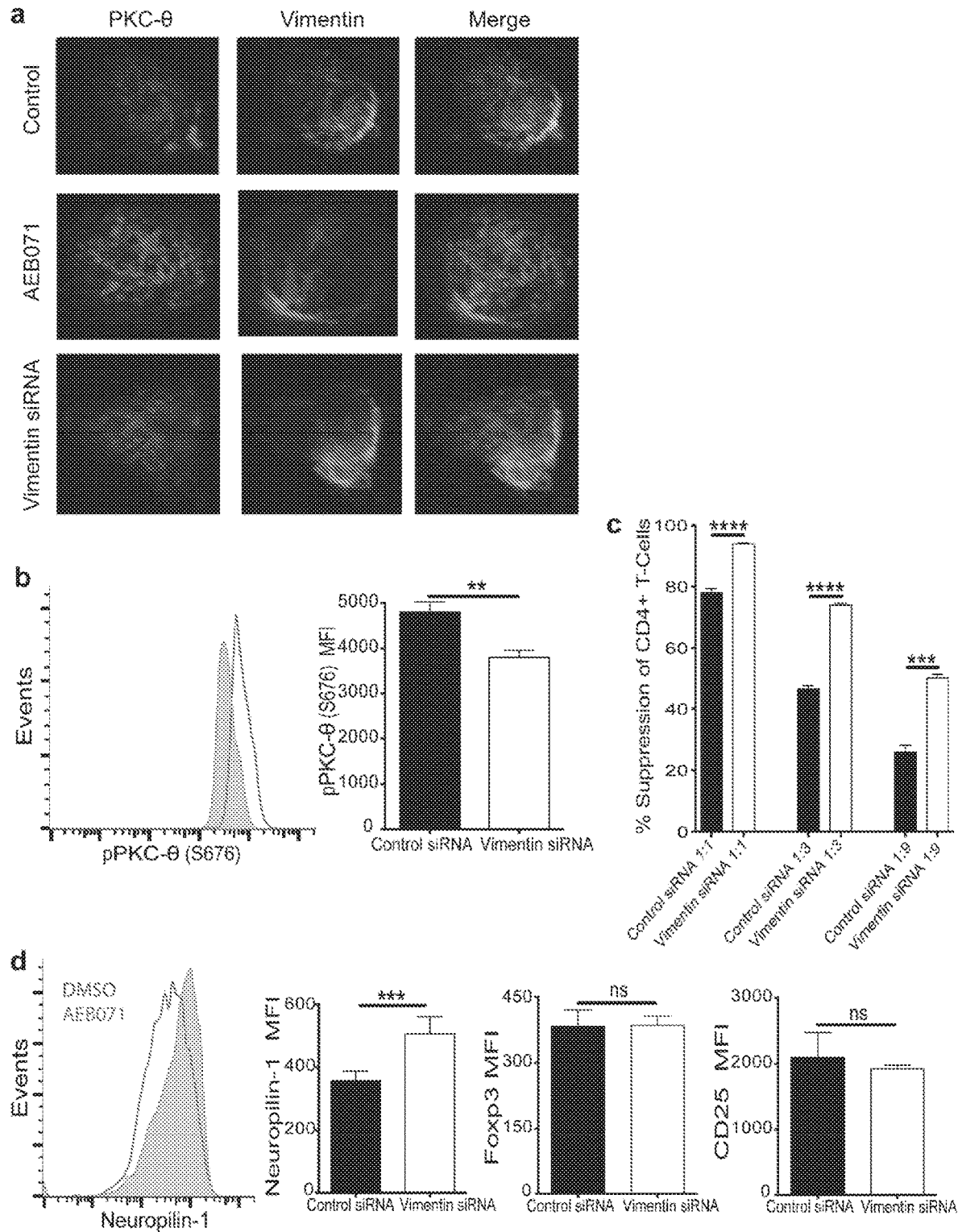

FIG. 8A are photographs of the results of experiments in which Tregs were pre-treated with DMSO (control), AEB071, or vimentin siRNA, then activated. PKC-θ and vimentin staining were analyzed by confocal microscopy. Data show one experiment representative of 4 independent experiments.

FIG. 8B is a representative histogram of PKC-θ phosphorylated at Ser676 after vimentin siRNA treatment, and a graph showing median fluorescent intensity (MFI) quantification. Data show one experiment representative of 2 independent experiments. n=4 replicates/group. Bars show mean±SEM. *, $p<0.05$; , $P<0.01$; *, $P<0.0001$; ****, $p<0.00001$ (Student's t-tests or one-way ANOVA with Tukey's post-test).

FIG. 8C is a graph showing percent in vitro suppression of CD4+ Tcon proliferation by control and vimentin siRNA-treated Tregs in a standard in vitro Treg suppression assay. 1:1-1:9 indicates Treg:Tcon ratio. Data show one experiment representative of 3 independent experiments. n=4 replicates/group. Bars show mean±SEM. *, $p<0.05$; , $p<0.01$; *, $P<0.0001$; ****, $p<0.00001$ (Student's t-tests or one-way ANOVA with Tukey's post-test).

FIG. 8D shows a representative histogram of Neuropilin-1 expression, and graphs showing MFI quantifications of Nrp1, Foxp3 and CD25. Data show one experiment representative of 3 independent experiments. n=4 replicates/group. Bars show mean±SEM. *, p<0.05; , P<0.01; *, P<0.0001; ****, p<0.00001 (Student's t-tests or one-way ANOVA with Tukey's post-test).

Figure 9:
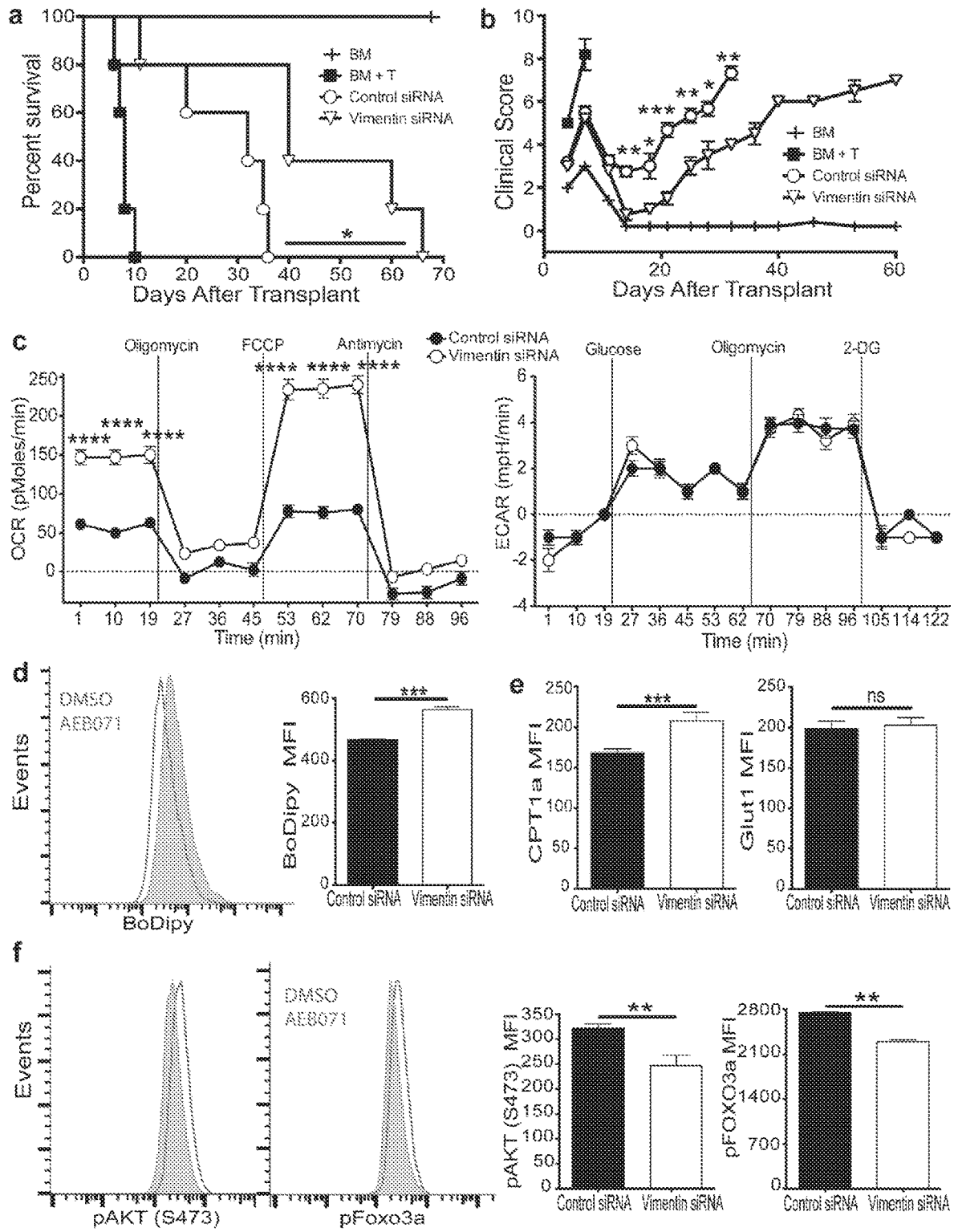

FIG. 9A is a graph showing the percent survival of recipients. Tregs were transfected with either control (non-targeting) or vimentin siRNA. Recipient mice were given BM alone, BM+Tcon (BM+T), or BM+Tcon+Tregs; Tregs pre-treated with control or vimentin siRNA. Data show one experiment representative of 3 independent experiments. n=5 mice/group/experiment. Bars show mean±SEM. Survival differences analyzed by log-rank test. *, p<0.05; , P<0.01; *, P<0.0001; ****, p<0.00001 (Student's t-tests or one-way ANOVA with Tukey's post-test).

FIG. 9B is a graph showing the clinical GVHD scores (0=no disease, 10=most severe disease) for recipients. Tregs were transfected with either control (non-targeting) or vimentin siRNA. Recipient mice were given BM alone, BM+Tcon (BM+T), or BM+Tcon+Tregs; Tregs pre-treated with control or vimentin siRNA. Data show one experiment representative of 3 independent experiments. n=5 mice/group/experiment. Bars show mean±SEM. Survival differences analyzed by log-rank test. *, p<0.05; , P<0.01; *, P<0.0001; ****, p<0.00001 (Student's t-tests or one-way ANOVA with Tukey's post-test).

FIG. 9C is a graph showing basal and maximal oxygen consumption rate (OCR) and extracellular acidification rate (ECAR) measured after transfection. Tregs were transfected with either control (non-targeting) or vimentin siRNA. Data show one experiment representative of 3 independent experiments. n=5 replicates/group. Bars show mean±SEM. Survival differences analyzed by log-rank test. *, p<0.05; , P<0.01; *, P<0.0001; ****, p<0.00001 (Student's t-tests or one-way ANOVA with Tukey's post-test).

FIG. 9D is a representative histogram showing BoDipy$_{C1-C12}$ uptake and a graph showing median fluorescent intensity (MFI) quantification of splenic Tregs from recipients on D4 after transplant. Tregs were transfected with either control (non-targeting) or vimentin siRNA, and recipients were given BM+Tcon+Tregs. Data show one experiment representative of 3 independent experiments. n=4 replicates/group. Bars show mean±SEM. Survival differences analyzed by log-rank test. *, p<0.05; , P<0.01; *, P<0.0001; ****, p<0.00001 (Student's t-tests or one-way ANOVA with Tukey's post-test).

FIG. 9E is a graph showing quantification of Glut1 and CPT1a MFI from flow cytometry analysis of splenic Tregs from recipients on D4 after transplant. Tregs were transfected with either control (non-targeting) or vimentin siRNA, and recipients were given BM+Tcon+Tregs. Data show one experiment representative of 3 independent experiments. n=4 replicates/group. Bars show mean±SEM. Survival differences analyzed by log-rank test. *, p<0.05; , P<0.01; *, P<0.0001; ****, p<0.00001 (Student's t-tests or one-way ANOVA with Tukey's post-test).

FIG. 9F are representative histograms showing Akt phosphorylation at Ser473 and Foxo3a phosphorylation (at Ser253) after control and vimentin siRNA transfection, and graphs showing corresponding MFI quantifications. Tregs were transfected with either control (non-targeting) or vimentin siRNA. Data show one experiment representative of 2 independent experiments. n=4 replicates/group. Bars show mean±SEM. Survival differences analyzed by log-rank test. *, p<0.05; , P<0.01; *, P<0.0001; ****, p<0.00001 (Student's t-tests or one-way ANOVA with Tukey's post-test).

Figure 10:
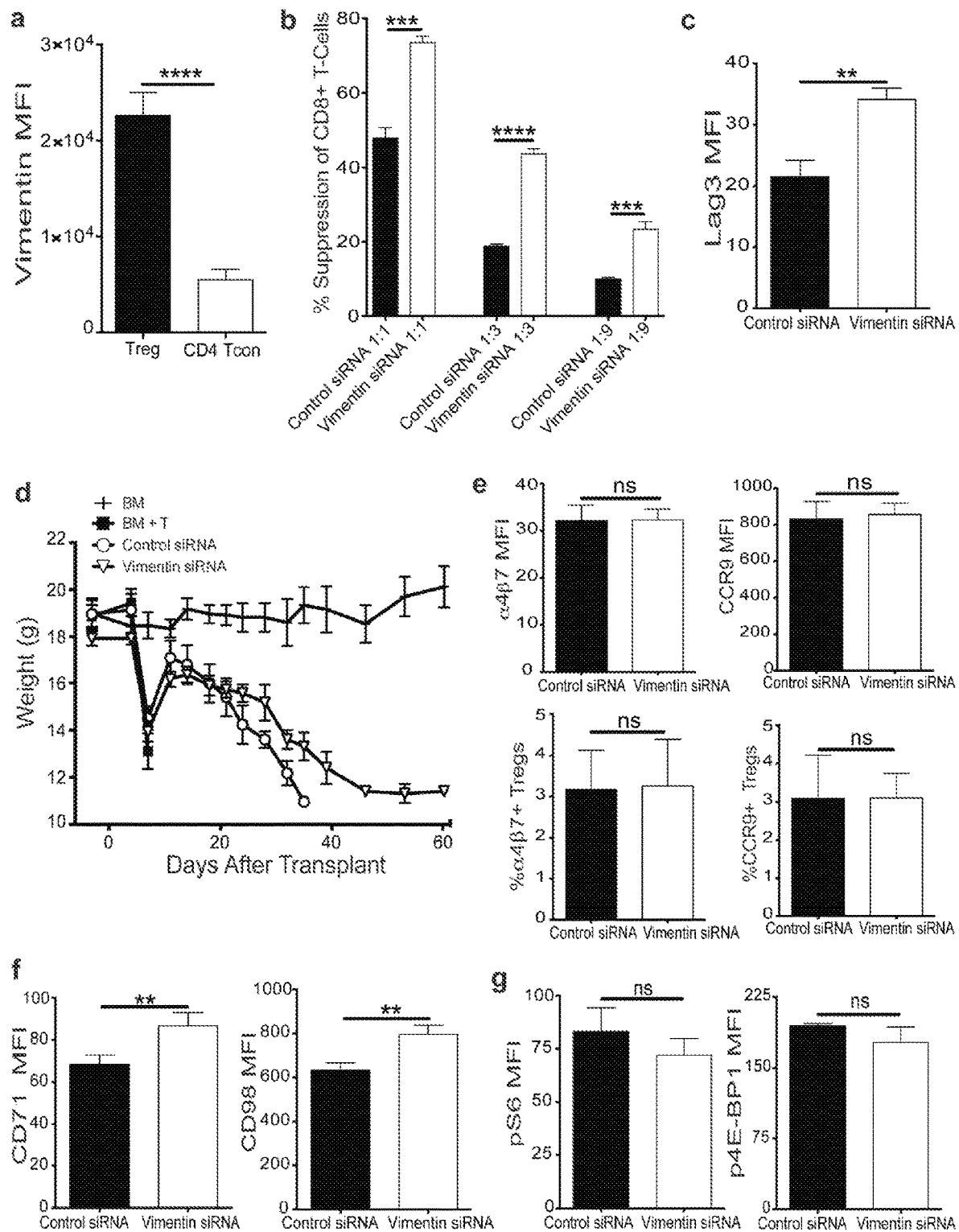

FIG. 10A is a graph showing the quantification of vimentin median fluorescent intensity (MFI) from flow cytometry analysis of purified Tregs and CD4+ Tcon. Data show one experiment representative of 4 independent experiments. n=4 replicates/group. Bars show mean±SEM. *, p<0.05; , P<0.01; *, P<0.0001; ****, p<0.00001 (Student's t-tests).

FIG. 10B is a graph showing the percent in vitro suppression of CD8+ Tcon proliferation in a standard in vitro Treg suppression assay. Data show one experiment representative of 3 independent experiments. n=4 replicates/group. Bars show mean±SEM. *, p<0.05; , P<0.01; *, P<0.0001; ****, p<0.00001 (Student's t-tests).

FIG. 10C is a graph showing MFI quantification of Lag3 expression in purified Tregs from flow cytometry analysis. Data show one experiment representative of 3 independent experiments. n=4 replicates/group. Bars show mean±SEM. *, p<0.05; , P<0.01; *, P<0.0001; ****, p<0.00001 (Student's t-tests).

FIG. 10D is a graph showing recipient weights from mice given only BM, BM+Tcon (BM+T), or BM+Tcon+Tregs. Data show one experiment representative of 3 independent experiments. n=5 mice/group/experiment. Bars show mean±SEM. *, p<0.05; , P<0.01; *, P<0.0001; ****, p<0.00001 (Student's t-tests).

FIG. 10E are graphs showing quantifications of alpha4beta7 and CCR9 MFI, and graphs showing percent of alpha4beta7 and CCR9 positive Tregs after transfection. Data show one experiment representative of 2 independent experiments. n=4 replicates/group. Bars show mean±SEM. *, p<0.05; , P<0.01; *, P<0.0001; ****, p<0.00001 (Student's t-tests).

FIG. 10F are graphs showing the quantification of CD71 and CD98 MFI from splenic Tregs from recipient mice transplanted with BM+Tcon+Tregs on D4 after transplant. Data show one experiment representative of 2 independent experiments. n=4 replicates/group. Bars show mean±SEM. *, p<0.05; , P<0.01; *, P<0.0001; ****, p<0.00001 (Student's t-tests).

FIG. 10G are graphs showing quantifications of S6 and 4E-BP1 phosphorylation after transfection. Data show one experiment representative of 2 independent experiments. n=4 replicates/group. Bars show mean±SEM. *, p<0.05; , P<0.01; *, P<0.0001; ****, p<0.00001 (Student's t-tests).

DETAILED DESCRIPTION

The present disclosure provides evidence that disrupting cytoskeletal structure in Tregs results in a release of structural components from physical constraints that is then able to increase suppressor cell potency. This effect can be direct (e.g., the molecule or compound released from the structural components within the Treg cells can exert this effect) or indirect (e.g., a molecule or compound that, upon binding to a binding partner such as, without limitation, adapter molecules, signaling molecules, enzymes, or molecules involved in degradation, recycling, mobility, metabolism, and/or differentiation, results in a release of one or more physical constraints in the Treg cells) or a combination thereof. Simply by way of example, and without being bound by any particular mechanism, such physical constraints within the Treg cells may occur at a cellular level (e.g., on the membrane of the cell, involving one or more cell-to-cell communication mechanisms) or at an intracellular level (e.g., on one or more organelles). This is the first evidence that there are structurally-based processes that occur within Treg cells that regulate their suppressor potency.

This phenomenon (e.g., the occurrence of structurally-based processes within Treg cells that regulate their suppressor potency) can be used in methods of increasing or augmenting the function (e.g., suppressor potency) of Treg cells. As described herein, increasing or augmenting the function of Treg cells can be accomplished by reducing or eliminating any of the vimentin protein, the RLTPR protein, or the PKC-θ protein, or a combination thereof.

Vimentin is a type III intermediate filament protein, and is the major cytoskeleton protein in mesenchymal cells. Vimentin plays a significant role in maintaining the position of organelles within the three-dimensional cell, but, at the same time, vimentin is a dynamic protein that allows for some of the structural flexibility exhibited by cells. The human vimentin nucleic acid sequence is shown in SEQ ID NO: 1, and the encoded protein is shown in SEQ ID NO: 2. The mouse vimentin nucleic acid sequence is shown in SEQ ID NO: 3, and the encoded protein is shown in SEQ ID NO: 4.

RLTPR is also known as CARMIL2 and is an adaptor protein that links PKC-θ with CD28. RLTPR knock-out mice exhibit a phenotype similar to CD28 knock-out mice, underscoring the importance of RLTPR in CD28/PKC-θ signaling (see, Liang, 2013, Nat. Immunol., 14(8):858-66). In addition, RLTPR also links protein kinase C-theta (PKC-θ) with the intermediate filament, vimentin (see, Liang, 2009, Mol. Biol. Cell., 20(24):5290-305). The human RLTPR nucleic acid sequence is shown in SEQ ID NO: 5, and the encoded protein is shown in SEQ ID NO: 6. The mouse RLTPR nucleic acid sequence is shown in SEQ ID NO: 7, and the encoded protein is shown in SEQ ID NO: 8.

Protein kinase C-theta (PKC-θ; also known as PRKCQ) is a member of the PKC family of serine- and threonine-specific protein kinases. PKC-θ is a calcium-independent and phospholipid-dependent protein kinase. The human PKC-θ nucleic acid sequence is shown in SEQ ID NO: 9, and the encoded protein is shown in SEQ ID NO: 10. The mouse PKC-θ nucleic acid sequence is shown in SEQ ID NO: 11, and the encoded protein is shown in SEQ ID NO: 12.

A nucleic acid encoding vimentin from human is shown in SEQ ID NO: 1, and a nucleic acid encoding vimentin from mouse is shown in SEQ ID NO: 3. In addition, a nucleic acid encoding RLTPR from human is shown in SEQ ID NO: 5, and a nucleic acid encoding RLTPR from mouse is shown in SEQ ID NO: 7. Further, a nucleic acid encoding PKC-θ from human is shown in SEQ ID NO:9, and a nucleic acid encoding PKC-θ from mouse is shown in SEQ ID NO:11. Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

The sequence of the vimentin polypeptide from human is shown in SEQ ID NO: 2, and the sequence of the vimentin polypeptide from mouse is shown in SEQ ID NO: 4. In addition, the sequence of the RLTPR polypeptide from human is shown in SEQ ID NO: 6, and the sequence of the RLTPR polypeptide from mouse is shown in SEQ ID NO: 8. Further, the sequence of the PKC-θ polypeptide from human is shown in SEQ ID NO:10, and the sequence of the PKC-θ polypeptide from mouse is shown in SEQ ID NO:12. As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Nucleic acids can be detected using any number of amplification techniques (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid. Nucleic acids also can be detected using hybridization.

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is oftentimes accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

A construct, sometimes referred to as a vector, containing a nucleic acid (e.g., a coding sequence or a RNAi nucleic acid molecule) is provided. Constructs, including expression constructs (or expression vectors), are commercially available or can be produced by recombinant DNA techniques routine in the art. A construct containing a nucleic acid can have expression elements operably linked to such a nucleic acid, and further can include sequences such as those encoding a selectable marker (e.g., an antibiotic resistance gene). A construct can encode a chimeric or fusion polypeptide (i.e., a first polypeptide operatively linked to a second polypeptide). Representative first (or second) polypeptides are those that can be used in purification of the other (i.e., second (or first), respectively) polypeptide including, without limitation, 6xHis tag or glutathione S-transferase (GST).

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame).

Constructs as described herein can be introduced into a host cell. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer. As used herein, "host cell" refers to the particular cell into which the nucleic acid is introduced and also includes the progeny or potential progeny of such a cell. A host cell can be any prokaryotic or eukaryotic cell. For example, nucleic acids can be introduced into bacterial cells such as E. coli, or into insect cells, yeast or mammalian cells (such as Chinese hamster ovary cells (CHO) or COS cells). Other suitable host cells are known to those skilled in the art.

A number of methods are known in the art that can be used to reduce or eliminate vimentin and/or RLTPR and/or PKC-θ polypeptides. For example, RNA interference (RNAi) nucleic acid molecules, nucleases (e.g., CRISPR, TALENs, megaTALs, meganucleases, zinc finger nucleases); antibodies (e.g., Fab, Fab2, chimeric, humanized); or ligands, peptides, drugs, chemicals, or small molecules that competitively bind vimentin or RLTPR or PKC-θ, that down-regulate vimentin or RLTPR or PKC-θ expression (transcription of DNA into RNA or translation of RNA into protein), that increase vimentin or RLTPR or PKC-θ degradation, or that cause intracellular depletion (e.g., by secretion) of vimentin or RLTPR or PKC-θ, can be used to reduce or eliminate vimentin and/or RLTPR and/or PKC-θ.

RNA interference (RNAi), also referred to as post-transcriptional gene silencing (PTGS), is known in the art and, as indicated herein, can be used to reduce or eliminate vimentin and/or RLTPR and/or PKC-θ polypeptides. RNAi is a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). In some instances, the use of RNAi can involve the introduction of long dsRNA (e.g., greater than 50 bps) or siRNAs (e.g., 12 to 23 bps) that have complementarity to the target gene, both of which are processed by the endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery. Irrespective of the particular type used (e.g., dsRNA, siRNA or shRNA), such RNAi nucleic acid molecules can be referred to as "specific inhibitory nucleic acid molecules" (e.g., a vimentin-specific inhibitory nucleic acid molecule, a RLTPR-specific inhibitory nucleic acid molecule, a PKC-θ-specific inhibitory nucleic acid molecule).

A RNAi nucleic acid molecule as described herein includes a nucleic acid molecule that is complementary to at least a portion of a target mRNA (i.e., a vimentin or a RLTPR or a PKC-θ mRNA); this nucleic acid molecule typically is referred to as an "antisense strand". Generally, the antisense strand includes at least 12 contiguous nucleotides of the DNA sequence (e.g., the vimentin nucleic acid sequence shown in SEQ ID NO: 1 or 3; the RLTPR nucleic acid sequence shown in SEQ ID NO: 5 or 7; or the PKC-θ nucleic acid sequence shown in SEQ ID NO: 9 or 11); it would be appreciated that the antisense strand has the "RNA equivalent" sequence of the DNA (e.g., uracils instead of thymines; ribose sugars instead of deoxyribose sugars).

A RNAi nucleic acid molecule can be, for example, 12 to 500 nucleotides in length (e.g., 12 to 50, 12 to 45, 12 to 30, 15 to 47, 15 to 38, 15 to 29, 16 to 53, 17 to 44, 17 to 38, 18 to 36, 19 to 49, 20 to 60, 20 to 40, 25 to 75, 25 to 100, 28 to 85, 30 to 90, 12 to 100, 12 to 300, 12 to 450, 15 to 70, 15 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, the antisense strand (e.g., a first nucleic acid) can be accompanied by a "sense strand" (e.g., a second nucleic acid), which is complementary to the antisense strand. In the latter case, each nucleic acid (e.g., each of the sense and antisense strands) can be between 12 and 500 nucleotides in length (e.g., between 12 to 50, 12 to 45, 12 to 30, 14 to 47, 15 to 38, 16 to 29, 17 to 53, 17 to 44, 17 to 38, 18 to 36, 19 to 49, 20 to 60, 20 to 40, 25 to 75, 25 to 100, 28 to 85, 30 to 90, 12 to 100, 13 to 300, 14 to 450, 16 to 70, 16 to 150, 16 to 275, 17 to 74, 17 to 162, 17 to 305, 18 to 60, 18 to 75, 18 to 250, 18 to 400, 20 to 35, 20 to 60, 20 to 80, 20 to 175, 20 to 225, 20 to 325, 20 to 400, 20 to 475, 25 to 45, 25 to 65, 25 to 100, 25 to 200, 25 to 250, 25 to 300, 25 to 350, 25 to 400, 25 to 450, 30 to 280, 35 to 250, 200 to 500, 200 to 400, 250 to 450, 250 to 350, or 300 to 400 nucleotides in length).

In some embodiments, a spacer nucleic acid, sometimes referred to as a loop nucleic acid, can be positioned between the sense strand and the antisense strand. In some embodiments, the spacer nucleic acid can be an intron (see, for example, Wesley et al., 2001, The Plant J., 27:581-90). In some embodiments, although not required, the intron can be functional (i.e., in sense orientation; i.e., spliceable) (see, for example, Smith et al., 2000, Nature, 407:319-20). A spacer nucleic acid can be between 20 nucleotides and 1000 nucleotides in length (e.g., 25-800, 25-600, 25-400, 50-750, 50-500, 50-250, 100-700, 100-500, 100-300, 250-700, 300-600, 400-700, 500-800, 600-850, or 700-1000 nucleotides in length).

In some embodiments, a construct can be produced by operably linking a promoter to a DNA region, that, when transcribed, produces an RNA molecule capable of forming a hairpin structure; and a DNA region involved in transcription termination and polyadenylation. It would be appreciated that the hairpin structure has two annealing RNA sequences, where one of the annealing RNA sequences of the hairpin RNA structure includes a sense sequence identical to at least 15 consecutive nucleotides of a vimentin or a RLTPR or a PKC-θ nucleotide sequence, and where the second of the annealing RNA sequences includes an antisense sequence that is identical to at least 15 consecutive nucleotides of the complement of the vimentin or the RLTPR or the PKC-θ nucleotide sequence. In addition, as indicated herein, the DNA region can include an intron (e.g., a functional intron). When present, the intron generally is located between the two annealing RNA sequences in sense orientation such that it is spliced out by the cellular machinery (e.g., the spliceosome). Such a construct can be introduced into one or more plant cells to reduce the phenotypic expression of a vimentin or a RLTPR or a PKC-θ nucleic acid (e.g., a nucleic acid sequence that is normally expressed in a Treg cell).

In some embodiments, a construct (e.g., an expression construct) can include an inverted-duplication of a segment of a target nucleic acid sequence, where the inverted-duplication includes a nucleotide sequence substantially identical to at least a portion of the target nucleic acid and the complement of a portion of the target nucleic acid. It would be appreciated that a single promoter can be used to drive expression of the inverted-duplication nucleic acid, and that the inverted-duplication typically contains at least one copy of the portion of the target nucleic acid in the sense orientation. Such a construct can be introduced into one or more Treg cells to delay, inhibit or otherwise reduce the expression of the target nucleic acid in the Treg cells.

Representative siRNA nucleic acid molecules directed toward vimentin are shown in SEQ ID NOs: 13, 14, 15, and 16. It would be appreciated by the skilled artisan that the region of complementarity, between the antisense strand of the RNAi and the mRNA or between the antisense strand of the RNAi and the sense strand of the RNAi, can be over the entire length of the RNAi nucleic acid molecule, or the region of complementarity can be less than the entire length of the RNAi nucleic acid molecule. For example, a region of complementarity can refer to, for example, at least 12 nucleotides in length up to, for example, 500 nucleotides in length (e.g., at least 12, 13, 14, 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 nucleotides in length). In some embodiments, a region of complementarity can refer to, for example, at least 12 contiguous nucleotides in length up to, for example, 500 contiguous nucleotides in length (e.g., at least 12, 13, 14, 15, 16, 17, 18, 19, 20, 25, 28, 30, 35, 49, 50, 60, 75, 80, 100, 150, 180, 200, 250, 300, 320, 385, 420, 435 nucleotides in length up to, e.g., 30, 35, 36, 40, 45, 49, 50, 60, 65, 75, 80, 85, 90, 100, 175, 200, 225, 250, 280, 300, 325, 350, 400, 450, or 475 contiguous nucleotides in length).

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides (or amino acid residues) between the two nucleic acids (or polypeptides) is determined. The number of identical matches is divided by the length of the aligned region (i.e., the number of aligned nucleotides (or amino acid residues)) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences (nucleic acid or polypeptide), and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

A construct (also known as a vector) containing a RNAi nucleic acid molecule is provided. Constructs, including expression constructs, are described herein and are known to those of skill in the art. Expression elements (e.g., promoters) that can be used to drive expression of a RNAi nucleic acid molecule are known in the art and include, without limitation, constitutive promoters such as, without limitation, the cassava mosaic virus (CsMVM) promoter, the cauliflower mosaic virus (CaMV) 35S promoter, the actin promoter, or the glyceraldehyde-3-phosphate dehydrogenase promoter, or tissue-specific promoters such as, without limitation, root-specific promoters such as the putrescine N-methyl transferase (PMT) promoter or the quinolinate phosphosibosyltransferase (QPT) promoter. It would be understood by a skilled artisan that a sense strand and an antisense strand can be delivered to and expressed in a target cell on separate constructs, or the sense and antisense strands can be delivered to and expressed in a target cell on a single construct (e.g., in one transcript). As discussed herein, a RNAi nucleic acid molecule delivered and expressed on a single strand also can include a spacer nucleic acid (e.g., a loop nucleic acid) such that the RNAi forms a small hairpin (shRNA).

Treg cells can be contacted in vitro, in situ, or in vivo with any of the moieties discussed herein (e.g., nucleic acids, nucleases, antibodies, ligands, peptides, drugs, chemicals, or small molecules) using any number of methods known to those skilled in the art. For example, Treg cells can be contacted with any of the moieties discussed herein (e.g., a nucleic acid (e.g., a vimentin-specific and/or a RLTPR-specific and/or a PKC-θ-specific inhibitory nucleic acid molecule; e.g., one or more RNAi molecules)) in vitro, in situ, or in vivo.

For example, one or more nucleic acids can be attached to or contained within a carrier such as, without limitation, liposomes, nanoparticles, or antibodies. Such carriers can be delivered to an individual (e.g., a patient) using routine cellular therapies, and such carriers can be targeted to Treg cells using one or more Treg targeting moieties such as, for example, cytokines that preferentially activate Tregs such as IL2; or the use of one or more moieties that specifically binds to a ligand that is preferentially expressed by Tregs such as neuropillin-1, lag3, TIGIT, CD39, CD73, IL10R, ST2, PD-1, CTLA4, CD49d, GITR, GARP, FR4.

The methods described herein can be applied to an individual who has received or is receiving a bone marrow transplant or a solid organ transplant. Alternatively, the methods described herein can be applied to an individual in order to treat or mitigate the symptoms of an autoimmune disease, or to induce tolerance to one or more foreign antigens (for example, in cases of enzyme therapy, gene therapy, antibody therapy, or drug therapy). Further, the methods described herein can be applied to an individual in order to treat or mitigate the symptoms of one or more allergic reactions.

Following contact with one or more of the moieties described herein, the Treg cells (e.g., Treg cells in which the vimentin, and/or RLTPR and/or PCK-θ has been reduced or eliminated) typically exhibit at least one of the following phenotypes (relative to Tregs in which vimentin, RLTPR and/or PCK-θ is not reduced or eliminated (e.g., relative to Tregs that lack the vimentin-specific and/or the RLTPR-specific and/or the PKC-θ-specific inhibitory nucleic acid molecule)): reduced PKC-θ auto-phosphorylation at Ser676; improved ability to suppress CD4+ and CD8+ Tcon proliferation; increased surface expression of Nrp1; increased surface expression of Lag3; increased basal and maximal oxygen consumption rate (OCR); increased BoDipy$_{C1-C12}$ uptake; increased expression of CD71; increased expression of CD98; increased expression of CPT1a; or reduced activity of mTORC2.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—PKC-θ Inhibition and Treg Function

Using a mouse MHC class I/II disparate acute GVHD model, it was found that freshly isolated Tregs treated for 30 minutes with 10 μM of the clinically available PKC-θ inhibitor, AEB071, suppressed GVHD mortality (FIG. 1A) and severity significantly better than DMSO-treated Tregs. As Tregs exert much of their protective effect against GVHD early in the course of the disease, proliferation of GVHD-causing conventional T-cells (Tcon) on D4 after transplant was analyzed. A significant reduction in Tcon proliferation in mice given AEB071 treated Tregs was observed compared to DMSO treated Tregs. Multi-photon microscopy on D4 was performed after transplant using TEα-GFP Tcon, CD11c-eYFP antigen presenting cells (APCs) and wild-type Tregs. Compared to DMSO, AEB071-treated Tregs significantly increased Tcon velocity and displacement from APCs. Increased velocity and displacement are indicative of decreased Tcon-APC interactions, suggesting reduced priming when AEB071-treated Tregs are present.

Figure 1:
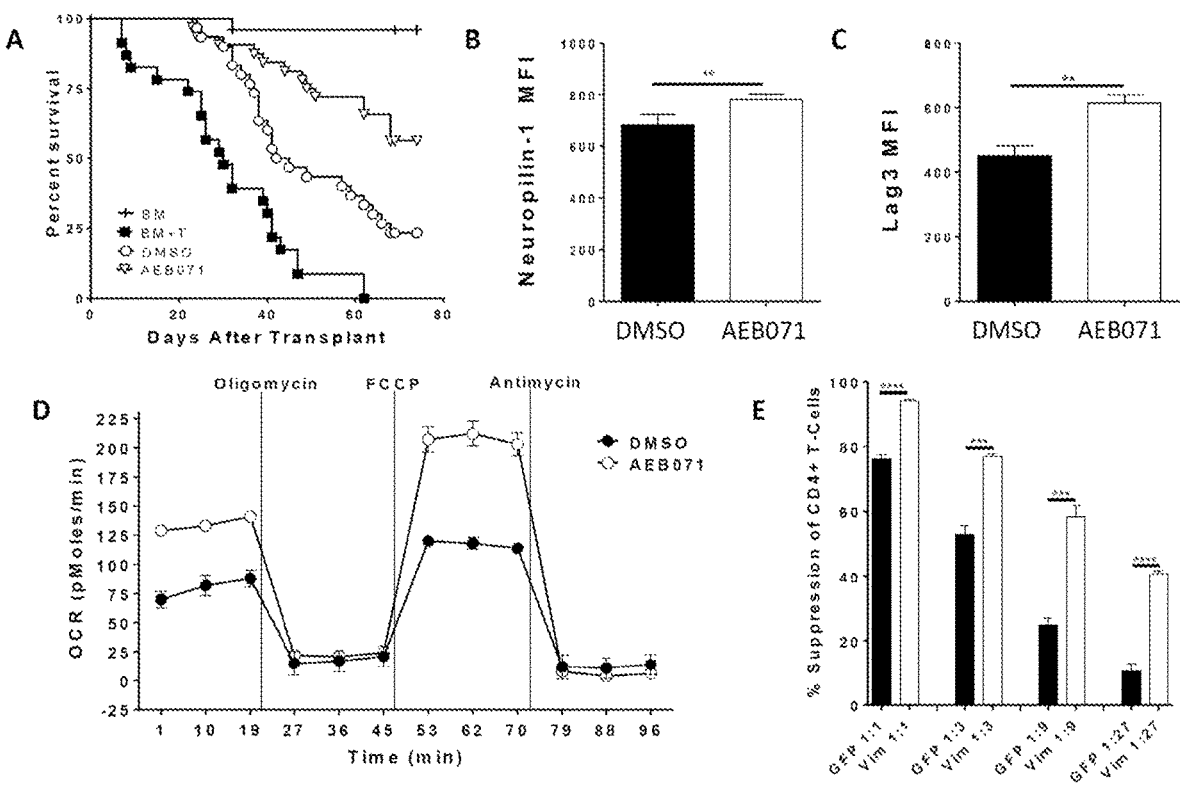
FIG. 1 shows that PKC-θ inhibition and vimentin siRNA treatment increase Treg function.

AEB071 vs DMSO treatment of Tregs resulted in augmented expression of the suppressive molecules, Neuropilin-1 (Nrp1) and Lymphocyte activation gene 3 (Lag3), after in vitro activation (FIGS. 1B and 1C) and in Tregs isolated from acute GVHD mice. Antibody blockade of Nrp1 and Lag3 in in vitro trans-well suppression assays reduced the effect of AEB071 treatment, suggesting that these molecules play a role in enhancing Treg function after PKC-θ inhibition. Flow cytometry analysis of phosphorylated proteins in activated Tregs revealed that PKC-θ inhibition resulted in reduced phosphorylation of the mTORC2 target, FoxO3a, but not mTORC1 targets, S6 and 4E-BP1. In addition, the mTORC2-specific phosphorylation site on Akt, serine 473, was reduced, whereas the mTORC1-specific phosphorylation site, threonine 308, was unaltered. Together, these data suggest reduced mTORC2 activity. Reduced phosphorylation increases FoxO3a nuclear translocation, which may result in increased Nrp1 and Lag3 expression, since FoxO3a has binding sites in both gene promoters. As both mTORC1 and mTORC2 are involved in T-cell metabolism, the effect of AEB071 treatment on Treg oxygen consumption rate (OCR) was investigated. Compared to DMSO, AEB071 treatment significantly increased Treg baseline and maximal OCRs after activation (FIG. 1D). Increased OCR has been associated with increased Treg function.

To identify additional alterations in phosphorylated proteins after PKC-θ inhibition, a phosphoproteomic screen was performed using in vitro-expanded human Tregs treated with AEB701 or DMSO. Significant alterations in phosphorylation sites on 72 proteins was observed, including reduced phosphorylation of an adaptor molecule that links PKC-θ to the intermediate filament, vimentin. It was found that vimentin is highly upregulated in Tregs compared to Tcon and that, in Tregs, vimentin interacts with PKC-θ after activation. AEB071 treatment reduced the interaction between vimentin and PKC-θ. As with AEB071 treatment, vimentin siRNA significantly increased Treg suppression in vitro compared to control-transfected Tregs (FIG. 1E), and augmented expression of Nrp1 and Lag3. AEB071-treatment of vimentin siRNA transfected Tregs did not further augment Treg function, suggesting an overlapping mechanism.

In summary, the data presented herein demonstrates that PKC-θ interacts with mTORC2 and vimentin to modulate multiple aspects of Treg function, and that a brief incubation of Tregs with a PKC-θ inhibitor or a reduction in vimentin protein levels may be viable methods to enhance the efficacy of Treg therapeutics.

Example 2—T-Cell Purification from Lymph Nodes

Lymph nodes were harvested into a gentle MACS C tube containing PBS with at least 2% FBS. The tissue was homogenized one or two times on the Miltenyi GentleMACS dissociator using the Spleen-1 protocol, inverting the tube between runs.

The tissue was spun at 1200 RPM for 10 minutes at 4° C. The supernatant was removed and the pellet was resuspended in MACS buffer (PBS containing 2% FBS and 1 mM EDTA). The solution was filtered through a 70 μM cell strainer into a 50 mL tube. The original C-tube was washed with additional MACS buffer and put through the strainer. The cells were counted at least three different times, and resuspended at 100×10e6 cells/mL in a 50 mL tube.

FCS was added to the cells at 50 μL/mL and a biotin-labeled antibody (e.g., anti-CD4, CD8, CD19, B220, CD11b, CD11c, anti-CD25, anti-NK1, anti-gamma delta TCR) was added and incubated for 10 minutes at room temperature. RapidSphere Magnetic Particles were added at 35 μL/mL and incubated for 10 minutes at room temperature. If the volume of cells after the RapidSpheres were added was between 1 and 10 mL, then 25 mL of MACS buffer was added and the sample was mixed gently. If the volume of cells after the RapidSpheres were added was between 11 and 40 mL, then 50 mL of MACS buffer was added and the sample was mixed gently. The samples were incubated on the magnet for 5 minutes at room temperature.

The negative fraction (e.g., the purified cells) were pipetted off and transferred to a different 50 mL tube. Cells were stained with anti-CD4, anti-CD8, and anti-CD25 antibodies to test for purity, and then counted at least three times. If the purity is not ideal, the sample can be placed in the magnet for another 5 minutes and the purity re-checked.

Example 3—T-Cell Purification from Spleen

The spleen was gently harvested into a MACS C tube containing PBS and at least 2% FBS. The tissue was homogenized 1 to 2 times on the Miltenyi GentleMACS dissociator using the Spleen-1 protocol, inverting the tube between runs. The tubes were spun at 1200 RPM for 10 minutes at 4° C.

The supernatant was removed and resuspended in 0.5-1 mL ACK lysis buffer (per spleen), and incubated for 1 minute. The C-tube was filled with MACS/PBS+2% FBS, and the solution was filtered through a 100 μM cell strainer into a 50 mL tube. The C-tube was washed with additional MACS buffer and put through the strainer. The sample was spun at 1200 rpm for 10 minutes at 4° C., the supernatant was removed, and the cells resuspended in MACS buffer. The cells were counted as least three times, and resuspended at 100×10e6 cells/mL in a fresh 50 mL tube.

FCS was added at 50 μL/mL, antibodies labeled with biotin were added (anti-CD19, B220, CD11b, CD11c, anti-CD4, CD8, CD25, NK1.1, DXS, gamma delta TCR), and incubated for 10 minutes at room temperature. RapidSphere Magnetic Particles were added at 55 μL/mL, and the sample was incubated for 10 minutes at room temperature. If the volume of cells after adding the RapidSpheres was between 1 and 10 mL, then 25 mL of MACS buffer was added and the sample gently mixed. If the volume of cells after adding the RapidSpheres was between 11 and 40 mL, then 50 mL of MACS buffer was added and the sample gently mixed. The samples were incubated on the magnet for 5 minutes at room temperature.

The negative fraction (e.g., purified cells) was pipetted off and transferred to another 50 mL tube. The cells were stained with anti-CD4, anti-CD8, and anti-CD25 to test for purity, then counted. If the purity is not ideal, the cells were placed in contact with the magnet for another 5 minutes, and their purity checked.

Example 4—T-Cell Purification Using CD25 Positive Selection

Cells were resuspended at 100×10e6 cells/mL. A selection antibody (anti-CD25 labeled with phycoerythrin (PE)) was added at 0.1 µl/10e6 cells (2 µg/mL), and the sample was incubated for 10 minutes at 4° C. The cells were washed one time with MACS buffer, spun at 1500 RPM for 5 minutes at 4° C., and the supernatant was removed.

Cells were resuspended at 0.8 mL/100×10e6 cells, and 1 µl/10e6 of anti-PE micro beads were added and incubated for 15 minutes at 4° C. Cells were washed one time with MACS buffer, spun at 1500 RPM for 5 minutes at 4 C, and the supernatant was removed. Cells were resuspended in a volume to bring the cells to 200×10e6 cells/mL.

A MS or LS column were placed on a magnet with a filter on top. The filter was washed with 500 µL MS or 2 mL LS buffer, and the column was loaded with the cells. The column was washed five times with 500 µL MS or 3 mL LS buffer. The column was removed from the magnet and the column was loaded with 1 mL MS or 5 mL LS buffer. The column was flushed with a plunger into a 15 mL tube. The cells were spun down, resuspended in 1 mL, and the steps above were repeated with a second MS/LS column. The cells were stained with anti CD4/8 to test for purity and counted at least three times.

Example 5—Amaxa Transfection (Nucleofection) Protocol for Mouse T-Cells

The number of cells was calculated to determine the number of cuvettes needed (e.g., 2-5.5 M cells per cuvette). After determining the number of cuvettes needed, 2 mL of fully supplemented Amaxa media with 300 IU/mL recombinant human IL-2 for each cuvette was warmed in a 12 well warm plate. After the cells are counted, they are pelleted by centrifugation at 1500 RPM for 5 minutes at 30° C.

As much of the supernatant as possible was removed, and cells were re-suspended in 100 µL of room temperature Amaxa Nucleofector solution per sample. Each sample contained about 2-5.5×10e6 healthy CD4+ T-cells in 100 µL of RT Nucleofector Solution. It would be appreciated that transfection will kill cell that are not healthy. To ensure healthy cells, the cells were rested for 2-4 hours to overnight in RPMI-c with 300 IU/mL recombinant human IL-2 at 37° C. prior to transfection.

Cell solutions were aliquoted into Amaxa cuvettes as follows: 10 µL of vim siRNA was added to a final concentration of 5 or 5 µL of Amaxa GFP was added to a final concentration of 2.5 µg per sample, then 100 µL of cells were added to each cuvette, and each cuvette was capped. A mock control cuvette using no GFP/siRNA also was included.

Cuvettes were loaded into the Amaxa Nucleofector II machine and transfected using Nucleofector Program X-001 for mouse CD4 T-cells. After transfection, the transfer pipettes provided by Amaxa were used to mix about 200-300 µL of warmed media with the cell solution in the cuvette, and the cells were gently transferred into a 12 well plate. The cells were allowed to rest in the incubator for 4-5 hours.

While the cells were resting, the same volume of new Amaxa media supplemented with 300 IU/mL rhIL-2 was warmed. After 4-5 hours, the cells were removed from each well, and spun down at 1500 RPM for 5 minutes at 37° C. As much of the supernatant as possible was removed, and the pellet was re-suspended in the warmed media containing rhIL-2. Cells were placed in a 12 well plate that had been coated with 10 µg/mL anti-CD3/28 the day before the experiment and allowed to sit overnight at 37° C., and spun for 5 min at 500 RPM at 37° C. The cells were placed in an incubator.

24 hours later, 1 ml of fresh media, with an additional 300 IU/mL of recombinant human IL-2, was added to each well. 48 hours later, the cells were ready for use. The cells were collected from the wells, spun down at 1500 RPM for 5 minutes at 30° C., and counted. Samples were taken to check transfection efficiency.

Example 6—Vimentin siRNA Transfection Methods

Regulatory T-cells (Tregs) were purified from lymph nodes and spleens of C57Bl/6 mice using a two-step process: Step 1: CD4 negative selection—selection of CD4+ T-cells was accomplished using eBioscience biotinylated Ab (anti-CD19, B220, CD8, NK1.1, gamma delta TCR) and StemCell technologies streptavidin RapidSpheres; and Step 2: CD25 positive selection—after CD4+ negative selection, CD25 positive selection was completed using eBioscience anti-CD25 PE Ab and Miltenyi anti-PE microbeads.

Once purified, Tregs were brought to a volume of about 1e6/mL in complete media with 300 IU/mL recombinant human IL-2, and the cells were rested for 2 hours at 37° C. in an incubator in a 24-well plate. After resting, Tregs were counted and split into 2 groups: one for transfection of control GFP siRNA and one for transfection of vimentin siRNA. After being split, Tregs were diluted in Amaxa Nucleofection Solution at a concentration of 5.5e6/100 µL and contacted with either 2.5 µg of control GFP plasmid or 5 µM vimentin siRNA per 100 µL.

A mixture of 4 siRNA oligonucleotides were combined in equal ratios such that the final concentration of the siRNA mixture is 5 µM. The siRNA oligonucleotides that were used have the following sequences: siRNA 1: CCA GAG AGA GGA AGC CGA A (SEQ ID NO: 13); siRNA 2: AGG AAG AGA UGG CUC GUC A (SEQ ID NO: 14); siRNA 3: GUC UUG ACC UUG AAC GGA A (SEQ ID NO: 15); and siRNA 4: AAG CAG GAG UCA AAC GAG U (SEQ ID NO: 16).

Cells were then placed in Lonza cuvettes (100 µL per cuvette) and electroporated using program X-001 in a Lonza Nucleofector II machine. After transfection, cells were placed in 2 mL of warmed complete Amaxa media (5% FBS, Pen/Strep, 10 µL/mL of Lonza media supplement) in a 12-well plate and incubated at 37° C. for 4 hours. After 4 hours, cells were removed from the wells, spun down (1500 RPM for 5 minutes), then diluted in 2 mL of warmed Amaxa complete media supplemented with 300 IU/mL recombinant human IL-2 and plated on a 12-well placed coated with anti-CD3 and anti-CD28 (10 µg/mL of each antibody). 24 hours after transfection (2D), 1 mL of Lonza complete media with 300 IU rhIL-2 was added to each well. 48 hours after transfection (3D), cells were removed from the wells, counted and used in functional studies.

Example 7—Vimentin siRNA Results

The experiments described herein demonstrated that vimentin siRNA significantly decreased vimentin levels in Tregs and that vimentin siRNA treatment increased the in vitro suppressive function in Tregs.

FIG. 2A shows that vimentin is highly enriched in Tregs compared to conventional CD4+ T-cells (CD4 Tcon). FIG. 2B shows that, compared to the transfection control (top panel), transfection with GFP-siRNA using the transfection protocol described herein yielded 50-60% or more transfection of Tregs. FIG. 2C shows that, compared to control GFP-siRNA (GFP), vimentin levels were knocked down by 15-30% in the presence of vimentin siRNA (vim siRNA). In total, the protocol described herein yielded 50-60% Tregs transfected with siRNA, and a 15-30% reduction in vimentin levels in transfected cells.

In standard in vitro suppression assays, vimentin siRNA-transfected Tregs (Vim) were able to suppress proliferation of both CD4 conventional T-cells (FIG. 3A) and CD8 conventional T-cells (FIG. 3B) significantly better than the control GFP-siRNA-transfected Tregs (GFP). Treg: Tcon ratios of 1:1-1:27 are represented with the 1:1, 1:3, etc., denotations in the x-axis labels.

Example 8—Suppression Assay

On day 3 after transfection, CD4/8 Tcon and T-cell depleted splenoctyes were isolated for a suppression assay. CD4/CD8 Tcon were purified from spleen of CD45.1 C57BL/6 mice using negative selection with eBioscience biotinylated Ab (anti-CD19, B220, NK1.1, gamma-delta TCR) and StemCell technologies streptavidin RapidSphere technology. Once isolated, Tcon were labeled with CFSE (2.5 µM) for 5 minutes at room temperature with constant agitation.

Responder Tcon were provided with 0.75 µg/mL soluble anti-CD3 mAb. This 0.75 µg/mL was equivalent to a 3× concentration such that the final concentration of anti-CD3, once Teff were mixed with stimulator splenocytes and Tregs, was 0.25 µg/mL.

Splenocytes from 1 CD45.1 C57BL/6 mouse were depleted of T-cells and NK cells using eBioscience biotinylated mAb (anti-CD4, CD8, NK1.1, gamma delta TCR) and StemCell technologies streptavidin RapidSphere technology. These TCD splenocytes were used as stimulator cells.

Ratios of 0:1, 1:1, 1:3, 1:9 and 1:27 Treg:Teff were made. Four replicates of each ratio were made and plated in a 96-well, round bottom plate. After 3 days in culture, the cells from each well were harvested, washed with PBS and then stained with antibodies for flow cytometry analysis of CFSE dilution (proliferation) of CD4 and CD8 Tcon. The antibodies used were as follows: CD4-BV510, CD8-PE-ef610, CD25-BV605, Nrp1-PerCP-ef710, Lag3-APC, Fixable viability dye-APC-ef780, Foxp3-PE-Cy7, and Vimentin-PE.

Example 9—Phosphoproteomic Screen with Human Treg Cells

Utilizing mass spectroscopy, a total of 12,452 phosphorylation sites were quantified from human Tregs. In order to determine significant differences between DMSO-treated and AEB071-treated Tregs, two experiments were performed concurrently:
Forward experiment: This experiment utilized heavy isotope-labeled Tregs treated with AEB071 and medium isotope-labeled Tregs treated with DMSO.
Reverse experiment: medium isotope-labeled Tregs treated with AEB071 and heavy isotope-labeled Tregs treated with DMSO.

After processing the raw spectra with Max Quant software, the positively identified phosphopeptides were analyzed using Persus software. Contaminating peptides and reverse database hits were filtered out and the peptide intensity values and normalized H/M ratios were log 2 transformed. The significances of the individual H/M ratios calculated using the Significance B test with a false discovery rate of 0.05 for the forward and reverse experiment separately.

Relying only on the Sig B test, the overlap between the two data sets was low with only 15% overlap. In order to improve the overlap between the two data sets, the data was filtered based on fold change (<1.5), consistency of ratios, phospho site localization probability (<75%), and the MaxQuant score (<75). By filtering the results, the overlap improved to 60%. See Table 1.

TABLE 1

| Significant Category | Sig B Test Only | Sig B Test and Filters |
|---|---|---|
| Forward Experiment | 380 | 96 |
| Reverse Experiment | 448 | 92 |
| Either For or Rev | 723 | 117 |
| Both | 105 (105/772 = 15%) | 72 (72/117 = 62%) |

Histograms show a nice symmetrical distribution centered at 0 (Log2 transformed data), indicating equal amounts of samples and labeling overall. See FIG. 4A. The scatter plot provides an indication of the consistency between samples. The red crosses are consistent between samples and, for the most part, cluster in the upper left quadrant as expected, since the inhibitor should decrease the levels of phosphorylation. See FIG. 4B.

The results of the phosphoproteomic screen pointed toward the PKC-θ adapter and interaction partner, RLTPR. The RLTPR protein had significantly reduced phosphorylation at the PKC-theta consensus site: IGVSRGS(ph)GAEGK (SEQ ID NO:17), with the phosphorylation site on the serine at residue 1226 indicated by the (ph) after the amino acid.

Example 10—RLTPR siRNA Transfection Methods and Results

Tregs were contacted with either 2.5 µg of control GFP plasmid or 1 µM, 5 µM, or 10 RLTPR siRNA per 100 µL. Cells were then placed in Lonza cuvettes (100 µL per cuvette) and electroporated using program X-001 in a Lonza Nucleofector II machine. After transfection, cells were placed in 2 mL of warmed complete Amaxa media (5% FBS, Pen/Strep, 10 µL/mL of Lonza media supplement) in a 12-well plate and incubated at 37° C. for 4 hours. After 4 hours, cells were removed from the wells, spun down (1500 RPM for 5 minutes), then diluted in 2 mL of warmed Amaxa complete media supplemented with 300 IU/mL recombinant human IL-2 and plated on a 12-well placed coated with anti-CD3 and anti-CD28 (10 µg/mL of each antibody). 24 hours after transfection (2D), 1 mL of Lonza complete media with 300 IU rhIL-2 was added to each well. 48 hours after transfection (3D), cells were removed from the wells and counted. The cells contacted with the 10 µM of RLTPR siRNA were used in functional studies.

FIGS. 5A-5D show that RLTPR siRNA significantly decreased RLTPR protein levels in Tregs. Results also demonstrated that RLTPR siRNA treatment (at 10 µM)

increased in vitro suppressive function (see FIGS. 6A and 6B) and augmented Nrp1 (see FIG. 7C).

Example 11—PKC-θ Inhibition Alters PKC-θ Localization and Vimentin Interaction

Since PKC-θ localization and function appear to be linked, experiments were performed to understand whether PKC-θ inhibition modulated PKC-θ localization. Consistent with previous work, PKC-θ accumulated at the distal pole of control Tregs after 5 minutes of anti-CD3/CD28 mAb activation (FIG. 8A, top). It was also found that PKC-θ was tightly associated with the intermediate filament, vimentin (FIG. 8A, top), a molecule that was found to be more highly expressed in Tregs compared to CD4+ Tcons (FIG. 10A). In contrast to controls, in AEB071-pre-treated Tregs, PKC-θ was dispersed throughout the cell after activation, and the overlap between PKC-θ and vimentin was reduced (FIG. 8A, middle). Since PKC-θ inhibition dispersed PKC-θ and reduced PKC-θ/vimentin overlap, experiments were performed to determine whether modifying vimentin levels with siRNA might result in comparable changes. Indeed, vimentin knockdown by as little as 30% resulted in a similar pattern as AEB071: dispersed PKC-θ, and reduced PKC-θ/vimentin overlap (FIG. 8A, bottom). These data demonstrate that inhibition of PKC-θ or vimentin alters PKC-θ localization and increases Treg function, and that PKC-θ/vimentin interactions may be important for PKC-θ trafficking.

Example 12—Vimentin siRNA Reduces PKC-θ Activity and Augments Treg Function

To better characterize whether PKC-θ/vimentin interactions were facilitating PKC-θ function, PKC-θ activity and Treg suppressive function were analyzed after treatment with vimentin siRNA. Using phosphoflow, it was noted that, similar to treatment with AEB071, PKC-θ auto-phosphorylation at Ser676 was significantly reduced in vimentin siRNA-treated Tregs compared with controls (FIG. 8B). Furthermore, vimentin siRNA-treated Tregs were significantly better at suppressing CD4+ and CD8+ Tcon proliferation in standard in vitro suppression assays compared to control Tregs (FIG. 8C, FIG. 10B). This increased Treg function correlated with a significant increase in surface expression of Nrp1 (FIG. 8D) and Lag3 (FIG. 10C). All other Treg suppressive molecules remained unchanged (FIG. 8D, and other data not shown).

To determine whether vimentin siRNA treatment would augment the ability of Treg to suppress GVHD, control- and vimentin siRNA-treated Tregs were compared using the GVHD model. Recipients given vimentin siRNA-treated Tregs had significantly increased survival and reduced GVHD severity compared with controls (FIG. 9A-B, FIG. 10D). As with AEB071 treatment, vimentin siRNA did not increase GI homing molecule expression (FIG. 10E). In combination, these results suggest that vimentin plays a key role in coordinating PKC-θ activity, and that vimentin knockdown in Tregs results in a similar functional enhancement as direct PKC-θ inhibition.

Example 13—Vimentin siRNA Augments Treg Metabolic Activity and Reduces mTORC2 Function Since PKC-θ inhibition modulated Treg metabolism and mTORC2 function, experiments were performed to determine whether vimentin siRNA might have a similar effect. As with PKC-θ inhibition, treatment with vimentin siRNA significantly increased basal and maximal OCR, but did not alter ECAR (FIG. 9C). In GVHD, vimentin siRNA-treated Treg also had increased $BoDipy_{C1-C12}$ uptake, and augmented expression of CD71, CD98, and CPT1a, but not Glut1 (FIG. 9D-E, FIG. 10F). $BoDipy_{C1-C12}$ uptake was also increased in vitro. Since mTORC2 signaling was reduced after PKC-θ inhibition, it was hypothesized that mTORC2 activity also could be reduced after treatment with vimentin siRNA. Consistent with this hypothesis, phosphoflow analysis demonstrated reduced phosphorylation of Akt at Ser473 and Foxo3a (FIG. 9F), but no change in the phosphorylation of S6 or 4E-BP-1 (FIG. 10G), in vimentin siRNA-treated Tregs versus controls. Together, these data demonstrate that reducing vimentin levels alters Treg metabolism (e.g., vimentin siRNA increases Treg function) and mTORC2 activity in a manner similar to PKC-θ inhibition.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of reducing or eliminating a cytoskeleton protein in Treg cells, comprising: contacting the Treg cells with a cytoskeleton protein-specific inhibitory nucleic acid molecule, wherein the cytoskeleton protein is a type III intermediate filament protein, and wherein the type III intermediate filament protein is vimentin.

2. The method of claim 1, wherein the cytoskeleton protein-specific inhibitory nucleic acid molecule is a RNAi nucleic acid molecule.

3. The method of claim 1, wherein the cytoskeleton protein-specific inhibitory nucleic acid molecule is an antisense nucleic acid molecule.

4. The method of claim 1, wherein the cytoskeleton protein-specific inhibitor nucleic acid molecule is a siRNA nucleic acid molecule.

5. The method of claim 1, wherein the vimentin-specific inhibitory nucleic acid molecule has the sequence shown in SEQ ID NO: 13, 14, 15 or 16.

6. The method of claim 1, wherein the Treg cells are contacted in vitro.

7. The method of claim 1, wherein the Treg cells are contacted in situ.

8. The method of claim 1, wherein the Treg cells are contacted in vivo in an individual who has received or is receiving a bone marrow transplant.

9. The method of claim 1, wherein the Treg cells exhibit a phenotype of at least one of the following:
 reduced PKC-θ auto-phosphorylation at Ser676;
 improved ability to suppress CD4+ and CD8+ Tcon proliferation;
 increased surface expression of Nrp1;
 increased surface expression of Lag3;
 increased basal and maximal oxygen consumption rate (OCR);
 increased BoDipy$_{C1-C12}$ uptake;
 increased expression of CD71;
 increased expression of CD98;
 increased expression of CPT1a; or
 reduced activity of mTORC2, relative to Tregs that lack the cytoskeleton protein-specific inhibitory nucleic acid molecule.

10. A method of increasing or augmenting the suppressor cell potency of Treg cells, comprising: reducing or eliminating vimentin in the Treg cells, wherein reducing or eliminating the vimentin in the Treg cells comprises contacting the Treg cells with a nucleic acid.

11. The method of claim 10, wherein the nucleic acid is a vimentin-specific inhibitory nucleic acid molecule.

12. The method of claim 11, wherein the vimentin-specific inhibitory nucleic acid molecule is a siRNA nucleic acid molecule.

13. The method of claim 10, wherein the method is performed in vitro.

14. The method of claim 10, wherein the method is performed in situ.

15. The method of claim 14, wherein the method is performed on an individual who has received or is receiving a bone marrow transplant.

16. The method of claim 10, wherein the Treg cells in which the vimentin has been reduced or eliminated exhibit a phenotype of at least one of the following:
 reduced PKC-θ auto-phosphorylation at Ser676;
 improved ability to suppress CD4+ and CD8+ Tcon proliferation;
 increased surface expression of Nrp1;
 increased surface expression of Lag3;
 increased basal and maximal oxygen consumption rate (OCR);
 increased BoDipy$_{C1-C12}$ uptake;
 increased expression of CD71;
 increased expression of CD98;
 increased expression of CPT1a; or
 reduced activity of mTORC2, relative to Tregs in which vimentin is not reduced or eliminated.

* * * * *

SEQUENCE LISTING

<160> NUMBER OF SEQ ID NOS: 17

<210> SEQ ID NO 1
<211> LENGTH: 9659
<212> TYPE: DNA
<213> ORGANISM: Homo sapiens

<400> SEQUENCE: 1
tttgtgttac ataattgcct ttcatttgaa ctcattaatc aaattggggt ttttaagcaa    60

-continued

```
cacctaatta attctttaac tggctcatat tataccttta atgacttcca ccagggtaaa      120
aaccactgat cactgagttc tattttgaaa ctacggacgt cgagtttcct ctttcaccca      180
gaattttcag atcttgttta aaaagttggg tgtggtttca tggggggagg gggaagagcg      240
agaggagacc agagggacgg gggcggggac tctgcaagaa aaaccttccc ggtgcaatcg      300
tgatctggga ggcccacgta tggcgcctct ccaaaggctg cagaagtttc ttgctaacaa      360
aaagtccgca cattcgagca aagacaggct ttagcgagtt attaaaaact taggggcgct      420
cttgtccccc acagggcccg accgcacaca gcaaggcgat ggcccagctg taagttggta      480
gcactgagaa ctagcagcgc gcgcggagcc cgctgagact tgaatcaatc tggtctaacg      540
gtttccccta aaccgctagg agccctcaat cggcgggaca gcagggcgcg gtgagtcacc      600
gccggtgact aagcgacccc accctctcc ctcgggcttt cctctgccac cgccgtctcg      660
caactcccgc cgtccgaagc tggactgagc ccgttaggtc cctcgacaga acctcccctc      720
cccccaacat ctctccgcca aggcaagtcg atggacagag gcgcgggccg gagcagcccc      780
cctttccaag cgggcggcgc gcgaggctgc ggcgaggcct gagccctgcg ttcctgcgct      840
gtgcgcgccc ccaccccgcg ttccaatctc aggcgctctt tgtttctttc tccgcgactt      900
cagatctgag ggattcctta ctctttcctc ttcccgctcc tttgcccgcg ggtctccccg      960
cctgaccgca gccccgagac cgccgcgcac ctcctcccac gcccctttgg cgtggtgcca     1020
ccggacccct ctggttcagt cccaggcgga cccccccctc accgcgcgac cccgcctttt     1080
tcagcacccc agggtgagcc cagctcgac tatcatccgg aaagccccca aaagtcccag      1140
cccagcgctg aagtaacggg accatgccca gtcccaggcc ccggagcagg aaggctcgag     1200
ggcgccccca ccccacccgc ccaccctccc cgcttctcgc taggtcccta ttggctggcg     1260
cgctccgcgg ctgggatggc agtgggaggg gaccctcttt cctaacgggg ttataaaaac     1320
agcgccctcg gcggggtcca gtcctctgcc actctcgctc cgaggtcccc gcgccagaga     1380
cgcagccgcg ctcccaccac ccacacccac cgcgccctcg ttcgcctctt ctccgggagc     1440
cagtccgcgc caccgccgcc gcccaggcca tcgccaccct ccgcagccat gtccaccagg     1500
tccgtgtcct cgtcctccta ccgcaggatg ttcgcggcc cgggcaccgc gagccggccg      1560
agctccagcc ggagctacgt gactacgtcc acccgcacct acagcctggg cagcgcgctg     1620
cgccccagca ccagccgcag cctctacgcc tcgtccccgg gcggcgtgta tgccacgcgc     1680
tcctctgccg tgcgcctgcg gagcagcgtg cccggggtgc ggctcctgca ggactcggtg     1740
gacttctcgc tggccgacgc catcaacacc gagttcaaga acacccgcac caacgagaag     1800
gtggagctgc aggagctgaa tgaccgcttc gccaactaca tcgacaaggt gcgcttcctg     1860
gagcagcaga ataagatcct gctggccgag ctcgagcagc tcaagggcca aggcaagtcg     1920
cgcctggggg acctctacga ggaggagatg cgggagctgc gccggcaggt ggaccagcta     1980
accaacgaca aagcccgcgt cgaggtggag gcgacaacc tggccgagga catcatgcgc     2040
ctccgggaga agtaaggctg cgcccatgca agtagctggg cctcggagg gggctggagg      2100 gagaggggaa cgcccccccg gccccgcgca gagctgccac gcccttgggg atgtggccgg     2160
ggggaggcct gccagggaga cagcggagag cggggctgtg gctgtggtgg cgcagccccg     2220
cccagaaccc agaccttgca gttcgcattt cctcctctgt ccccacacat gcccaagga      2280 cgctccgttt caagttacag atttcttaaa actaccactt tgtgtgcagt tgaaggccct     2340
tgggcacaat gagagccagt cctccaaact ttcagaaagt ttcctgcccc ttctggcagg     2400
```

```
ctgccaatca ccgggcggga aaggaagga ggggaaggcg gtggagggag cgagacaaag   2460
ggatggtccc tcggggcgg ggatggcggg gctgtcctgt aggtctgtgc ggccaccgtg   2520
attgcccctc tgcgcggtgc ccgaagtccc gctgaaacct gccgagggca gcaggtctga   2580
aagctgcagg cgctagttgc gcggaggtgg cgcagctgct ctggaggcgc agagcgaata   2640
cgtggtgttt gggtgtggcc gccccgcccc tggcggtttc ctcgttcccc tttggttaat   2700
gcgcaactgt ttcagattgc aggaggagat gcttcagaga gaggaagccg aaaacaccct   2760
gcaatctttc agacaggttt gtagactctc ttcccactcg cagccgcctg accccaccca   2820
acacaaccca cgagcaattc taaaagttgc ttaactcacg tctaaaaagt gcaaaacttc   2880
agggctgcgc gtaaagccct ctagtggcgg aagaccaca ggttggagct tctcatgatt   2940
agaaaaatat aataaaaacc ccttgagcga ttttttttt tttttgaga cggagtctta   3000
ctctgtcgcc caggctggag tgcagtggcg agatcttggc tcactgcatc ctccgcctcc   3060
cgggttcaag cgatccttga atgatttcta agcagttcct tgggacataa agaaaaatct   3120
tttaactttt tactttgttt cccaaatgtt gcacagtttt gcaacacatt gaccttctgg   3180
tttcgaacgg ttacaatttt agattgtggt ttgccaaagt caagttgctt aattttaca   3240
aggccacaaa aagcgcaatt atgccctgca gtttaaaatg gaaaacgtgt tggaagataa   3300
gaaaacttag tttccaactg gaatggagcc agcaagtttc ttttcttctt tgcaaattct   3360
attgtgtcat taaagttcga tggaagtatc actatgcaca actattttgt gatctaataa   3420
gggtgaaaag gagccatctg tccccttggc taaggggtat taatggtttc tatgggcttc   3480
actatggaat gtagatacag acattctggc aaatgtggtg gctctggaca gaataatag    3540
gagtctttgt attcccaggg aagctttgca acaggctaca ttcttactga atatgtaatg   3600
atgtaagcac ggttctaatt ggacacaagt atttgctaac atccgttatc taatatctgg   3660
cccagacttg agaagtaggt aatgtaaaaa gttttttaag ctacaagcat acctcacatt   3720
ttaaaagtcc tttcttgatt gggttcttgt gttcttagc actcttgcca taaaaaataa   3780
taacagtaat aaacccaagg ctgaaaaact gaattttaac taaagggttt ttgtgcgtgt   3840
tttttttttt tttcaccaaa attagatgga cttacagaat tttttaactta aaattggaat   3900
ccaaaagcca gaagatcccc attatagttt atagttgtat tccctggaat atttactggg   3960
attaactgca aagcactctc agatgaatag tgtagtataa cattttgaaa ctgaaataca   4020
tttaccaaat taatttaacc acagcaatgt gtgtggttca ttttagtcct tgagcatttt   4080
tgattatcat acctgtcatg ttttctgcag tgtagtgagt taacataaaa caacatcaat   4140
acaaaagatc ctctgtttcg agattaagca aaattcctca ttctcttcaa tgtgatagaa   4200
taccacattg atctttcttt ggaggttagt aaaatatctt ttatgtattt ttcagggctt   4260
aacaagtaaa aatcaatgtt ttcatcaagt ctgatctttt tgtcacccac tcttcattca   4320
tttttccact aaggtgatag aaaagtctca acagtttaag accgtaaggc tatgaactcc   4380
aaatataatt gctgacaaga taagcaatcc tcacgcatcc ttttgagagg aaataaaatc   4440
ttagttgcaa gattacatat tctgatttgg aatgctgagc ttttaaatg gaaatataga   4500
aggacggctg aatcagcaaa aatcctttat gtagtttcat tctttgcaag cttgaccagt   4560
cattctgaaa caggctaact gaactgatac agtggcaagt gaaaaagaca tgcctttaca   4620
ggatgagtca aaggagtttt agaagaaaaa tccaccagag aaagccaagc aaatacagtt   4680
cagagttaca tttcttttcc attttttcct gaactgaatc tttggcatgc atatcctgaa   4740
ttgggttatt gaatataaat ctagccttgt acaatggatg ccagatgact acatatttgc   4800
```

```
tttggagcct aaggataagt ttcaaaagat ttgagtggag aagaaaagct aaaactcttg    4860
aagcacaagt ttctgttctc catgtactca agtgtacatg aagttgtgaa aatttgtcca    4920
cctctatcat catgttattc catgaaatta caaaacaaat cttaaaaatg ttgtggcata    4980
gattttctag atttaaaaag taattaaatt aaatgaatta ctttattttt tgagacagag    5040
tgtcactctg ttgcccaggc tggagtgcag tggcactatg ttggctcact gcaacctctg    5100
cctcctgggt tgaagaaatt ctcctgcctc aacctcccaa gtagctggga ctacaggcat    5160
gtgccaccac acccagctaa ttttttgtatt tttggtagag acggggtttc gccatgttgg    5220
ctaggctggt ctcgaactcc tgacctcaag tgatccaccc gtctcagcct cccaaagtgc    5280
tgggattaca ggcataagcc accatgacca gccttaaaaa gtaattttaa aatatcactg    5340
gtaaaatgtg gattcagtca tgattgagtg cagtttacca tgtgtgtgga catttattta    5400
ttttaaaatt gtctgatcac caccttgagt aaaacacaag cagtcacaat taaaatatat    5460
tagtgagcag gagaaagcac agcatattat agcactgaat gatttataaa cctattccag    5520
ggtcataaaa tgtgtcaacg ctttttctat agtaaggaga ctaggttcag atggttaatc    5580
taagacaaat aaatgagata agccatacac ttttacatcc tccatgtcct gtcttttctc    5640
tgttcaaaat aggatgttga caatgcgtct ctggcacgtc ttgaccttga acgcaaagtg    5700
gaatctttgc aagaagagat tgcctttttg aagaaactcc acgaagaggt tagtggagtg    5760
actttcgggg aatgaatgag ggtaaggcag cccccacggt tggcagagct gaccgtctgt    5820
ctgttctttt tgcaggaaat ccaggagctg caggctcaga ttcaggaaca gcatgtccaa    5880
atcgatgtgg atgtttccaa gcctgacctc acggctgccc tgcgtgacgt acgtcagcaa    5940
tatgaaagtg tggctgccaa gaacctgcag gaggcagaag aatggtacaa atccaaggta    6000
ggaaacaaat cagtgcggct tcaaccaaag aaaagcattg tgttctcaaa accccatacc    6060
tgtgtgtgat tcctaaatat cctctagctc caatgcaaag ctggctttga cttcttgctc    6120
atattgtgtt tgccaccaca gcctccccac cactcacatc acctccttta tttatttatt    6180
tattttctta tttatttatg agacagagtc ttgctctact gcccaggctg gagtgcagtg    6240
gcaacatctt ggcacactgc aacctccgcc tcccaggttc aagtgattct cctgcctcag    6300 cccccctaaga gctggaacca caggcaagca ccaccatgcc cggctaattt ttgtattttt    6360
agtagagatg gggtttcacc atgttgacca ggcttctctc aaactcctga cctcaggtga    6420
tccaccctcc tcagcctccc aaaatgttgg gattacaggc atgcgccacc acgcctggcc    6480
acatcacctc cttcagaata gcagactctc ttccccctaa ccttgcctcc aagtaaaccc    6540
caatgccata cctttgacct ccactgtgtt gaaatgagca ctgtagagtg aactctgaaa    6600
atactaatgt cagtactcca ctgctctttc cctggctttc aaaacagaaa tttaaaccta    6660
tactggaaga cattcagtga gaaatatgat ttttttttc taagagagtc aaaagacttg    6720
aatgtgagca atctacattt ctgttttctt cccaacagtt tgctgacctc tctgaggctg    6780
ccaaccggaa caatgacgcc ctgcgccagg caaagcagga gtccactgag taccggagac    6840
aggtgcagtc cctcacctgt gaagtggatg cccttaaagg aaccgtgagt accaaccctg    6900
cagtaaaaga gggaaaataa tgacccattc tgctgactag gctcatgatg ataccctgaac    6960 aaaatgttga gtgagtaaaa atgtatatca taatgcaaag aaaatgagtt atcaagacag    7020
actcaaaagg gacttcatgg aactcttgaa ggttttagct tgcctatatc attgcttcta    7080
atatgaagga cttggtactc gcattctcca cctaaaatta gagtggtcgc catttgccgc    7140
```

```
taatggaaat tattgcagaa ggtctgtaaa tggttctggg aacagctggg tttttctgag    7200
aaataacacc agacatcttt ctcacccct gcagaatgag tccctggaac gccagatgcg    7260
tgaaatggaa gagaactttg ccgttgaagc tgctaactac aagacacta ttggccgcct    7320 gcaggatgag attcagaata tgaaggagga aatggctcgt caccttcgtg aataccaaga    7380
cctgctcaat gttaagatgg cccttgacat tgagattgcc acctacagga agctgctgga    7440
aggcgaggag agcaggtagg gaactcgac ttggatgcgt gaactaatgg tgaccatttg    7500
ttaggccctg tgccactggg ctctaagcag tgtcacattt aatctttaga agtttctttt    7560
gaggtaactg ctttccactt tttgtagagg aggaatttga attgagagag agtaagtgac    7620
ttgctgaaaa agggttaatc aacagcagag ctgggatttg aacccataac tctgtcaaag    7680
cctccactcc taactcctgt tcatgctcct gtggagaaaa tgcttgtagt aacatatttt    7740
aaatgtacta acaagaccag tcatgggaaa atgtttctga gacaaatctc tagtttatga    7800
tttaaaacag tacgttttct tacgtgacga aaacaaaaag tgtgttaatt tgttcccagt    7860
ggttgaagtt atttgccaac aatttactg tttctcttca tctgtttata ggatttctct    7920
gcctcttcca aacttttcct ccctgaacct gagggtaag cattttattt cctttagga    7980 aaaacgtcag ctgcttgtaa ccactgtgtt tatgtcaaag cattcatttt ttttaggata    8040
tctgaaaaaa tgccatataa gagaaaactc tataaaacat ctataatttt cgaacccaag    8100
tacactcttg cattctatgc tttaagttaa atgcaaactc cttttccctt cttcctgctg    8160
caagtactat ctcatcctga tgctcaagag tgtcagggcc tgggtttcca aacagagact    8220
accctaaaat tatttggcga gtagtacttt acacaattgc ctctccccca caaatcataa    8280
ttgtttcagt aaaatggtta cttggttttt ccaagaaaaa actcgttttt actcatttt    8340 ggcctgtttg tttatttaga aactaatctg gattcactcc ctctggttga tacccactca    8400
aaaaggacac ttctgattaa gacggttgaa actagagatg acaggttgg tatcttttaa    8460 ggaaaaaata gggtaatctc agacaggagt tgatatattt taaaatcagt gaatctgaat    8520
ctcagataca gctggctaat ttgagaggtt caggtttcat tcatgcctac taaaaaaga    8580 ataggcttct tcttccagca gtacacacag ccaactaatt atttggctcc tggatgtgaa    8640
gttgagatag cagtcttcct gtgctccaga attagtgatt tgctttggtg cttaatttga    8700
agtgggagta agcttcctta aaccacttcc taaagcagct acatgaaaca gcttcactag    8760
actacctcaa tatgaggaat gttttgatcc tggacatatg gtgtcttcct acctccatac    8820
tttatagatt cctaaaccca tctatataat acaagcatgt gccatacgat catttagttt    8880
cttattacct cccctatgcca ggaaagaaat agttgcaatt tattgtagtc atcatgaaat    8940
cttcccttgc acataaattt aaaatgtacc tgctgcacat tttaatatgt cttaattgct    9000
tttaaacttg gctgtattgt gtacaactat tataccatct tttataaaca cagtttttta    9060
agaaatttct ttttgtaagt tacaacattc cactggatcc ttatattgcc tgtagtggaa    9120
gagggtcttg tgtgtctgcc ccttctagtt ttcactcatg cagaagcaac ataaccttct    9180
gatttgcaca ataaattaca tatatttagc aggatttta tttgccgtga tatataggat    9240
aatttagtct ttggcatgtg gcattatatt tatttggtt ttttttttta aacaggttat    9300
caacgaaact tctcagcatc acgatgacct tgaataaaaa ttgcacacac tcagtgcagc    9360
aatatattac cagcaagaat aaaaagaaa tccatatctt aaagaaacag ctttcaagtg    9420
cctttctgca gttttcagg agcgcaagat agatttggaa taggaataag ctctagttct    9480
taacaaccga cactcctaca agatttagaa aaaagtttac aacataatct agtttacaga    9540
```

```
aaaatcttgt gctagaatac tttttaaaag gtattttgaa taccattaaa actgctttt    9600 tttttccagc aagtatccaa ccaacttggt tctgcttcaa taaatctttg gaaaaactc    9659

<210> SEQ ID NO 2
<211> LENGTH: 466
<212> TYPE: PRT
<213> ORGANISM: Homo sapiens

<400> SEQUENCE: 2

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350
```

```
Val Glu Ala Ala Asn Tyr Gln Asp Thr Ile Gly Arg Leu Gln Asp Glu
            355                 360                 365

Ile Gln Asn Met Lys Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
    450                 455                 460

Leu Glu
465

<210> SEQ ID NO 3
<211> LENGTH: 8515
<212> TYPE: DNA
<213> ORGANISM: Mus musculus

<400> SEQUENCE: 3
ctctgccact cttgctccgg gaccccagag accccagcgc tcctacgatt cacagccacc      60
gcgccctcat tcccttgttg cagttttttcc agccgcagca agccagccca ccttcgaagc    120
catgtctacc aggtctgtgt cctcgtcctc ctaccgcagg atgttcggtg ctccggcac     180 atcgagccgg cccagctcca accggagcta tgtgaccacg tccacacgca cctacagtct    240
gggcagcgca ctgcgcccca gcactagccg cagcctctat tcctcatccc ccggtggcgc    300
ctatgtgacc cggtcctcgg cagtgcgcct gcggagcagc gtgccgggcg tgcggctgct    360
tcaagactcg gtggacttct cgctggccga cgccatcaac actgagttca gaacacccg    420 caccaacgag aaggtagaac tgcaggagct gaatgaccgc tttgccaact acatcgacaa    480
ggtgcgcttc ctcgagcagc agaacaaaat cctgctggct gagctcgagc agctcaaggg    540
ccagggcaag tcgcgcctgg gcgacctgta cgaggaggag atgcgggagc tgcgccggca    600
ggtggatcag ctcaccaacg acaaggcccg tgtcgaggtg gagcgggaca acctggccga    660
ggacatcatg cggctgcgag agaagtaagg cctgacctac gcgagtggtg gggtgtggga    720
gggaggggag tcctgggcct tgcactgggg ctgccacgcc ttggggatg tggctggggt     780 ggcggttgtc tggaggatag cagaggaagc gggcccccacc ctgaacctaa actttgcagt    840
gaacatttct cttttcgcct cactcaagca cttccattga acttttaga aagtttctta     900 ggtccttctt ctgggcttac agttaccaga caggaggaaa gaatgggtgt gaagggttcc    960
agacaaagag atggcaaagg catctgggat attgggacag gggattggct gtaattgtaa   1020
gggaagggca gtgattgtct tttccagtgt gccccaactc cagctaacac ctgcagagag   1080
ctgccacctc gacaagttgc agtaactact gtgggtggag gtgtcacagc agctctggac   1140
tcaaggcttg gcggcatttg tggttgggtg tggccgcccc gcccctggcg ttttccagt    1200 tcccctttga ttaatgtgct gctgcttcag attgcaggag gagatgctcc agagagagga   1260
agccgaaagc accctgcagt cattcagaca ggtttgtaga cttctttttc acatgcagcc   1320
agcagcccaa tggagccaac ccgcgagcgg ttctaaaagt tacttccctt aggttttaaa   1380
aggtgcagaa cttcacgtct gcttgtaaag ccccctggcg gcggaaagcg cacagattga   1440
```

```
aaaactccac tatttagggc agtctttgga acatgaaggc tttattttct gcttcgtttc    1500 cagattttc  tgatccccca cacccccgaa acatttctcc tttcgttttt tgaaacatat    1560
cgacattcgg atattgaatg gttacaattt gattacattg tggattgtga aggtgaaatt    1620
ggctaacttt cacaaggtca taaaaaccac agttgcttcc tccagttgga aatgtagaat    1680
actctggagg atgagaaagt ttaactggaa ttaagccaag ttccctttct tccttcgaag    1740
ttcggcactg cgtgaaagtt agcagaagag tcattgcaca accatttttg aaatctaaca    1800
agggtgaaaa gaagccatct gttcccgtag ctcaagggtg ttaaaggttt ctatgggctt    1860
cactatggaa tgtagatagg gacgttctgg caaatgcggt ggctctggac agaaagaata    1920
ggggcctttg tgttcccaga gcagctttgc aacaggctac attcttattg aatatgtaat    1980
gatgtaacca cagttccaat tggacacaag tatttgctaa catccattat cttgtgtctg    2040
ggccaggctt gtgaggtatg ccgtgtacaa agttcttaaa gctaaagtcc tccctcacat    2100
ttggaaaggc cccctttag  gggggtttgt agactcatta gcaccctcca caaacaaaat    2160
taaaccctaa actgaagaat ggagtatttt atggagggag gatttgtttg tttgtgtttg    2220
ttccagggtt aggcattacc ttagcatccc gaagtggaca gatggccagt tcagtcttgt    2280
ttggaacact tgttaggatc aacagccaaa ctctccagat gaatgttcta aggtagcatt    2340
ctgaaggcat ttgcatcctt aatggcagta gacgaatatg cagccccttt cagtcactgg    2400
gcattttcag tcatcaccaa aggaatgttt tctacaaagc actgagttaa tacacaccat    2460
ctcttatttg tggactaaaa attgtttcat tcattcattt aaatgaaatg acacatttag    2520 ctgaacttt  tcgagaaggt tagtccaata tcatttatat atttttgat  ggcttagcag    2580 aagtcagaaa tgaatgatac tactatttaa gttcttatat tctttttaa  attagtattt    2640 tctttgggac tgatagagta actcaacatt atagttataa actatactgc aaatacagtt    2700
gcttacaagg gaagtttcca aacatttcct tgaaaggaaa caacatttca catgcaagat    2760
tgaacagtct gtcttaaaat agatcacttt ataaaaactc tgcagagaag tttaagtata    2820
gtttcattgt aagtgttttg atctgtcatc ctaaaacaga caaagtcatt gaaataacac    2880
tgtgacagct gggacaggca gaaatacccct ataggctgag ccagggtgtt ttacacatta    2940
aaaaaattag agaaggcaaa acaatatagt tcaggattat atttctttc  cttcttgccc    3000 gaggagcata tctctgcaaa tgcaagacct ggattttgaa caatgaatta ctacttgata    3060
cgaggctagc ctgggaacct ggatgccaga taactgagtg cttattctaa attccaaaga    3120
taagcatctg aaggtttgaa tacaggaaac aaaaaagagc atgcatatat gttaacccctt   3180 ctgagctcaa ttttaaatga tttttaaaaa atatgtaatg tgtttgtgtc tgtgtgagtg    3240
tataggacat ttctgcaggc ttgcatgagg ccagaagagg gcacctgatg ccctggagtt    3300
ggaatcataa accttcatga actgctccat gtgggtgctg ggaaccaaac taaaatcctc    3360
tgaaagaaca gcattcttta ctactaagcc tcactttaga aaacatttta attttatttt    3420
tgaagctctc attttatat  tacgtgtact caagcaaaca tgaagttgga caatctcatc    3480
aactactatc atcacaaaat tacagactta ttaaatgtga cagaggttta aaactgaaaa    3540 tgaattttc  catatagttc accataccat gtcattgtgc atatacatgt gtttatttt     3600 aacttgtcta ctagttagct tcaatacaac caaatggttt cctattcatt tttaaagcta    3660
agaatgaata ttggaatgtg accctaaatg atttataaat ttatcaaggg tcatgaaatt    3720
ttcagcacct tttctacaat aaggagaatg ggtttacatg gttaatttt  gaacaaataa    3780
```

```
ataaataaat aaataaataa ataaataaat aaataagggg ctgtagagac aggtcaatgg    3840
ttaaaagcac tggctactct tttagggcac ctggaattca atttgcagaa cccacagggc    3900
tgcccacact cttctccagt tccagggcat cttttgctct cttattgctt ttgtggatac    3960
cacatgctcg tggcatactt atatacatgc aggcaaaaca cctttataca aacataaag     4020 tgaaaaggg attaatataa ataagttaga taaaggacag actttatcac cctccacatc     4080
atcttttctc ttttcgaaat aggatgttga caatgcttct ctggcacgtc ttgaccttga    4140
acggaaagtg gaatccttgc aggaagaaat tgccttttg aagaaactgc acgatgaagt     4200
aagtgacacc aatttctgtg ggtgaacaaa gctgcgaccg tgtagtctac gacctctctg    4260
tgtctgttct ttctccagga gatccaggag ctgcaggccc agattcagga acagcatgtc    4320
cagatcgatg tggacgtttc caagcctgac ctcactgctg ccctgcgtga tgtgcgccag    4380
cagtatgaaa gcgtggctgc caagaacctc caggaggccg aggaatggta caagtccaag    4440
gtatgaaatg agccagagtg gcaagaacct ctagctctca gacacgtgcc tctaattcca    4500
ttagtaacct ccagctctac tcagaagctg gcttaaagct tggaccgcca ttgttgtttc    4560
acagcacccc ttcccctca tctccattca cagtttcctt tagtatggca gactcccttt     4620
ccactcattg tcttccctga cttcaaagaa taccttactc tcatgctctt gactgccacc    4680
acttggaaag cattgcagta gagcaaatac tgtttgaaaa cgcaatgctg gtgttctgct    4740
tctctttccc tggttttcca aaagacgttc agacaaattc taggaaacac acaggcagga    4800
tgaagatgcc tctttgttct aagtgagtga aaactcatgg aagtgaacaa tctctacttc    4860
ttttcttttc ttttcttttc ttttcttttc ttttcttttc ttttcttttc ttttctttct    4920
cctcctcctc ctccttctcc tcctcctcct cctcctcctc ttcttcttct tctacttctt    4980
cttcttcttc ttcttcttct tcttcttctt cttcttcttc ttcttcttct tcttcttctt    5040
cttcttcttc ttcttcttcg actaagctca caaccaaaaa caacctctat ttctgattcc    5100
ttcttgacag tttgctgacc tctctgaggc tgccaaccgg aacaacgatg ccctgcgcca    5160
ggccaagcag gagtcaaacg agtaccggag acaggtgcag tcactcacct gtgaagtgga    5220
tgcccttaaa ggcactgtga gtactacagc agcaaagggg gggaaatacc gtgctcagta    5280
ctattctgct gactaggtta acaatgagac ctgtacaaat aaattaaaca cacacggaca    5340
cacacacaca cacttatcca aagagaatga attatcaaga tagttttaag gattatttaa    5400
tgagtacctt gaaagtctta gtttacatat gttattgatt gtaataagag gggttttaga    5460
ggttactcct gtaacctcat cactctggag aatgaggcag ggggattata aattcacagt    5520
taagctaggc tgcatgtaaa agtgttattt catcaaagca aaacatggaa ctgggtgctt    5580
gtgttctctg ttcaaagcta gtgggcacct accattaaaa gaattactgt accttattta    5640
tgaatatttt gggggacagc cgggttttct gggaaatcac atgagaagcc attttgtctt    5700
tctgcagaac gagtccctgg agcgccagat gcgtgagatg gaagagaatt ttgcccttga    5760
agctgctaac taccaggaca ctattggccg cctgcaggat gagatccaaa acatgaagga    5820
agagatggct cgtcaccttc gtgaatacca agatctgctc aatgttaaga tggcccctgga   5880 cattgagatc gccacctaca ggaagctgct ggaaggcgag gagagcaggt atagaaggca    5940
aacgtgcatg tgtgaactaa ctcacagtcg tctttctagg aagatctcat ttaacccaga    6000
caccatatat atgaggaact taacgttgca gagagtaact tgctgtggtc agagataatt    6060
aatagcagag tagatttgaa ctcacagcca tgcaaaagac aatacgttct ccctctataa    6120
attcttctgg ttcatgtttc tgtgtggaaa aaaatatctt ccgaaattta aatgggccaa    6180
```

```
tgagaccaag catgggtaga aagttcttaa acaagtcact aacagcaata gattttcatt    6240
tggtggaaac aagaactgcg aaaacttgtt cctgcttctt gaagtgcttt gttctcaagt    6300
tttttgtgtg tttctttctc tttttatagg atttctctgc ctctgccaac ctttctcttcc   6360 ctgaacctga gaggtaagta cattgtttca tcttatggga aaaaaatgtc acaaggctgt    6420
caccagtcac tctgcctgta gcatagcttc cacattttta aaaatatttt ttattacgta    6480
ttttcctcaa ttacatttcc aatgctatcc caaaagtccc ccataccctc ccccccactc    6540
ctctacccac ccactcccac agtaattctt gattgaactg tgcttttcca agaaaattc     6600 aatgaaacat gatttctctt ttataaatac atgtgtatag ccattttatt ttctgaatat    6660
ttcttttggg cttctgaggt tctgatagag ttaagtcact ttctcgcttc cgtttcttct    6720
ctcgaaacct tccatgtact gcccctgac atatatggct gtcttttcag ttcatggctt     6780 cctttgttt aaatgctgtt acacacacac acacacacac acacacacac acacacacac     6840
acactgtgta ttcttacata catgagtaca atggctcatt ctgtataata ttacttacat    6900
gtatgctttc aggctcgacc atctggtccc ttttttatta tagttctcat gactgctgga    6960
gaccaaaccc agggcaatca gctaagctaa cccacagag ctccacccct agcctgatac      7020
cctcagtttc aaactcgagt acattcttgc ctttgctacc ctgttaagta tagactcagt    7080
ctacttcctg ctaatggcaa agtcagtgaa ctactacctc agcctgaatg aaggagccct    7140
taggtgctgt gtactcaaat ggatagtgct atgtaggatt atgtatgagt agcactttaa    7200
ataaccataa aaataaagtc atgatgcttt gggtaaaatg gtaatgtttt aaacttttc     7260 ttatgttact gccttttttt tttttttttt ttttaattc agaaactaac ctggagtcac     7320
ttcctctggt tgacacccac tcaaaaagaa cactcctgat taagacggtt gagaccagag    7380
atggacaggt cagtattttt tagttaaaat atgggaaagt ttaaaagaag gaatgatgaa    7440
taaactatac aaccacttta aatatgtgtt ggtcccctt aagtcagcaa gcagatatat     7500
cagatatggc agctaactta aggagtcccc gtggatactg gatgaatagc ccccaattcc    7560
accaatgcaa gaaccaacag tctatttggt cttgattagg acagtaaact tcctgcacac    7620
catagtctgt gcactaaaca ggagtaaaac acccttaagg catctcttac attggctgca    7680
ttaaagtgtg tcacttaatg acatccgtga tatcagggat agtttgacat tggacataca    7740
gttctctctc agtgattgtc acctgctat atagtacgag gacccatatg tggtcaatca    7800
ctttcttgtt gccactccat gccagggaag acatagttac aatgagttat aattataaaa    7860
gctcagcctt gcatgaggat ataaaataca tttgccatac ctctacatat gccttagttg    7920
cttttaagct ttgtttggaa ttgcaaaggc caacttccta aacacagttt caaagtattt    7980
tttgtcacac ctttccactg gatacttgta ttgtctgcag gaagaggcca ccctgcctat    8040
gcttctcctt agggcctcgt tctgcagagt cagcataaac tcccagtctg ctcaaccaat    8100
tctgtctgat tagggccata tctccttacc atgagttgat ttttgtttct ttttgagca    8160 ggtgatcaat gagacttctc agcatcacga tgaccttgaa taaaaattgc acacacttgg    8220
tgcaacagtg cagtaccagc aagaaggaaa aaaaatcgt atcttaggaa acagctttc      8280 aagtgccttt actgcagttt ttcaggagcg caagatagat ttggaataga aagagctca    8340 gcacttaaca actgacaccc caaaagacgt agaaaaggtt tacaaaataa tctagtttac    8400
gaagaaatct tgtgctagaa tacttttaa agtattttg aataccatta aaactgcttt      8460
tttccagtaa atatctgacc aacttgttac tgcttcaata aatcttcaaa aatac         8515
```

-continued

```
<210> SEQ ID NO 4
<211> LENGTH: 466
<212> TYPE: PRT
<213> ORGANISM: Mus musculus

<400> SEQUENCE: 4

Met Ser Thr Arg Ser Val Ser Ser Ser Tyr Arg Arg Met Phe Gly
1               5                   10                  15

Gly Ser Gly Thr Ser Ser Arg Pro Ser Ser Asn Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ser Ser Pro Gly Gly Ala Tyr Val Thr Arg
50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Ser Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Asp Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Asn Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Leu Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380
```

```
Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
            405                 410                 415

Thr Phe Ser Ser Leu Asn Leu Arg Glu Thr Asn Leu Gly Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
            450                 455                 460

Leu Glu
465

<210> SEQ ID NO 5
<211> LENGTH: 12566
<212> TYPE: DNA
<213> ORGANISM: Homo sapiens

<400> SEQUENCE: 5
gggcgggcag gtgggactcg gccccctcc cacaacccg ctcccgggca agctctcgag      60
ccgcgaggcc ggggcgggga ggggccgggc cggggcggc ctggcaggaa gcggcgcgca    120
ccttccgccg ccgaggagc aggtggctgc cgtgcgggtc tgggcccag gcttcctgtg     180 tgcgcgctcg tcctctgctg tttccgccg gagctcgttg ggcctcccg gcccgcccgg    240 cccatggccc agacccccga cggcatctcc tgtgagctcc gaggtaagcg ctggcccttc    300
ctgccttctt ggccgggagg aagtagtgca gccccaaaat cagaggccca cccagcgccc    360
cagagggcct ggtcagaggt cctccctgct ccccaggagg gcaggcgccc cagatcctct    420
cccctccttc ctcgctggcc gcagataagc cccagggccc cagcctggca cagactgtgg    480
gcaccagtgg cttctgtgca aggactgaag tcacccagca ggctgccctt ccacaggcga    540
gatcaccagg ttcctgtggc ccaaagaggt ggagctgctg ctgaaaacct ggctacccgg    600
ggagggtgct gtgcaaaacc atgtcctggt atggggcagg ggacagagcc ggggaggcgg    660
ctgtggcccc acagaaagag cctcttgctc tgcccaggat atcagactgt ctttccccag    720
gcactgctac gatggagagc ctacctgctg cacaccacct gcctcccgct gagggtgagt    780
cccagggcct ggccacaccc ccgccgcca gcagctacct tggcagggg ctgcatctgc    840 agagtggtcc ttcttggcct tgtgggccct gactttgcac cagcactggg ctctgggcag    900
ccgacaggag gggagtccag gcagatctgg ctctgcccca ggctgcccaa aggactggac    960
ttccatgagg gcggggctgg gggcttggtc ccagctgatc taggccctt ctaggtggac   1020 tgcacgttca gctacctgga ggtccaggcc atggcgctgc aggagacacc ccctcaggtg   1080
agacacctag taccctacct gggcctgcag cctggtcttc atgctaccac catcacctgc   1140
gcccatgtgt ggagccgagg cctagtagtg tccccttccct aggtcacctt tgagctggag   1200
tccctgcgtg agctggtcct ggagtttcct ggtgtggccg cctggaaca gctggcccag   1260 cacgtggctg cagccatcaa gaaggtcttc cctcgctcga cccttgggtg aggcctggca   1320
aattcgaggg gctggcaggg gaggagggag tgcatgagaa gggctgcttc ccatcccaga   1380
ggctggaagt cctttgcccc cttctcctta accccctacc aggaagctat tccggaggcc   1440
cacaccagcc tccatgctgg ctcggctgga gagaagcagc cctcggagt ccactgaccc   1500 ctgcagcccc tgtggtaagg gtgaaggcag agccacaggc cttccagcct gccccacctc   1560
```

```
tgcctcccca gacccgcaag ctggggggggc cccaaactga acagagccat tcaggtccca    1620
gccaccacct agtctgtggg tctggtcttc ctccatcgct gatgttttgt ctctctcctt    1680
ttccacatcg caccccctatc ccctccccag gtggcttctt ggagacatac gaggctctgt    1740
gtgactacaa tggcttccct ttccgagagg agattcagtg ggtgagggta gggcccttt     1800 gaagggctct ggagacatct ggtcccccat gtgtgctgag cccctccctg cccctttgtgg   1860 ccccaggcga actgtaagca tctccttctc acccaggacg tggacaccat ttaccatcgc    1920
cagggctgcc gccatttcag cctgggagac ttcagccacc tcggcagtcg gtgtgtggcc    1980
tgccaggatg ggagaggagg aagatcccgg ggcccatatc cctgggcctc agtttctcca    2040 tggagggggct gctgggcctg ggacctggct ggagggccct gagctctgcc tctgttccca   2100
ccctcccacc agggacctgg ccttgagtgt ggctgccctg tcctacaacc tgtggttccg    2160
gtgcctctcc tgtgtggaca tgaagctggt gaggggggttc ggggtaaggg cagggagggg   2220
ccaagggtgt gggccagggt gcagcccgct gagggccagg gtgcagcccg tgagccgccg   2280
ccctctgctt ctcagagcct tgaggtctca aacagattc tgcacatgat gagtcagtca    2340
tcacacctgg aggagctggt gctggagacc tgcagcctga gggggtgagg gggacagggc   2400
agggcttgga gaggagagtc tggaggcttg ggactggggg ctagtggcct gggagggggtt  2460 ggcaaaccag gggcagaatc tcatgcctgg ggtctggtcc ccagagactt tgtccgacga   2520
ctggcccagg cgctggcggg acactcaagc tctgggctgc gggagctcag cctcgcgggg   2580
aacctgctgg atgaccgagg tatgactgag cctggggacc gcaggggtgg gcagcaggag   2640
gaggtgagac ccacgtggct gttcccaccc cccaaggcat gactgcactc agcagacacc    2700
tcgagcgttg tccaggagcc ctgaggagac tcagcctggc ccagacaggg ttgacaccgc    2760
gaggtaggct ggatgaggga ggggggtgagg ggagggggggt ggggggtctgt ccaactgctg  2820 agtgaccccg acccaccacc aggaatgagg gctctgggcc gggcactggc caccaatgcc    2880
gccttcgact ccaccctgac ccacctggac cttttctggga atcctggggc gctgggggcc    2940
tccgaggaca gtggggtgag tggctgtctt cagggtggga gcttggggttt gctcataagc   3000 cctgggtagg cgatccccca ctccatcgca ccctgtcct ccctccaggg cctctatagc    3060
ttcctgagcc gtcctaacgt actgtcgttc ctgaatctcg caggcaccga cactgccctg   3120
gacactgtga gggggtgctc cgtgggggga tggatgaccg gcagggcgga ctggagggcg    3180
ggacggggag ggctcggtcc ccccgcgggt gtagccaaca gcctccccccc gcagctcttc   3240 gcagcggtat cccgaggctg ctgcaccagc cttacccacc tcgacgcttc gaggaacgtc   3300
ttctcccgca cgtaagggg acctgtcggg gccggggggag gctgctggaa gccgcctcct    3360
tgcggcccca ggcccacctt cccacttccc ccaggaagtc ccgcgccgcg ccggccgcgc    3420
tgcagctctt cctcagccgc gcgcggacgc tgcggcacct gggcctggcg ggctgcaagc   3480
tgccgcccga cgcgctcagg tcagtgtcgg acccggccca cgccccgcg ggcgctccca    3540 ccctgccctg gccttcgccc ctcccccgctc ctgcttctgt cgctcccaca acctccccca   3600
gatcctggcc ctgcctcctt cgttcgcacc ctggagcccc ctgtcccagc tcccgccacc   3660
ccgtgtaacg tcctctccca gagccctttt ggatggcctc gcgctcaaca cgcacctccg   3720
cgacctgcac ctggacctca cgcgcttgcga ggtgagcgcc ggcccccaga agagaccaca   3780
cattgggaga ggcgctgggga ggcggaaggg cagggccgtg ggccgcctgc ccctcccccac  3840 tcgcggccta agtgggtccc acttcccacc tcccacctcc cacatacagc tgcgctcggc   3900
cggcgcccag gtgatacaag acttagtgtg cgacgcaggc gctgtgagct ccctggatct   3960
```

```
ggcggataac ggtgaggctg caggagagcc catcctcgca tcatccactc gattcccaat    4020
ccccacccta cccttgcaac ttcgcctcgt gcgtgacccg agtcacccccc aggcttcggc    4080 tcagacatgg tgactctggt gctggccatc gggagaagcc ggtccctgag acatgtggcg    4140
cttggaagga acttcaacgt ccggtgcaag tgagccccca ccctactcct gggcctccca    4200
gacaacaccc caccacccct gtccccaca actgcggccc ctgcccacag ggagaccctg    4260
gacgacgtcc tgcaccggat tgtccagctc atgcaggacg acgattgtgt gagttcacgg    4320
gaccttgcag ggcctcgggc aattagacca ctttggtcct cctttctctt gttccctcag    4380
accctgtgac ctgccctcac tgaccccga ctccagccat caatggcttt ctcttaaccc    4440
cagcctcttc agtctctgtc ggtggctgag tctcggctga agctgggtgc cagcgtccta    4500
ctccgggccc tagccaccaa tcctaacctg accgcgctgg atatcagcgg caacgccatg    4560
ggggacgcgg cgccaagtt gctggccaag gcgctgcggg tcaactcgag gctccggtgg    4620
gcggggtcag aggggtggga ccagcggca ggggcgcgg tggagaggag ggcaccgggc    4680
taaggggagg gactgaatga ggcggagcaa atggagcagg ctgacgaggc gaatggacta    4740
ggccgagggt tgggtggggc gttgggaagc tccgtcccg actgaagcca ggcccggccc    4800
aggtctgtgg tctgggaccg gaaccacaca tctgctttgg gtctgctgga cgtggcgcag    4860
gcgctggagc agaaccacag cctgaaggcc atgcctctgc cactgaacga cgtggcccag    4920
gcgcagcgca gccgccggga actgacagca cgtgcagtcc atcaggtggg cgtcccctc    4980 ttcccttgcc cttctctgca cggtaactcc gtccctcggc atttctcaat acccccttgcc    5040 cctagatcca agcctgtctc ttgaggaaca accgcgcaga ccctgcctct tctgaccaca    5100
cgacccgcct tcagccactt ggtctggtct cagaccccctc agagcaggtc aatgtccct    5160 ccccaaccac gagaggtagg gcatgaggag acctgtggca tccgggagcc tccatgagtc    5220
agagggtctg acttttcctgg ggccagggtg cctgagccct gctgtcccac acaaagtccc    5280
tctccttgat ctggaggcgg ctaaacaccc cttaaatagc tctccaaata cacccttgg    5340 ctgcctaacg ttaagcctgt aaacaggctg tcctgttaga gaggaatttt tatgtccttc    5400 ctcaatttttc ccccaattgt agccccatct ctgtcctcac atatacgtga ctcccctccc    5460
ctctccattg tgtgcccaaa cccagctgct ccttcactgt cttcatctcc ctccactacc    5520
ttatctgttg gagatgtttc tacctctcca ttcccaaata cctcttcttt cctaagcttc    5580
agagcccaaa ggtcttaatc cagacatcct gctgggcttc atgctctgca cttctccaag    5640
tgatgtcatc gtcgctcaca aaccctgttg tctaccctgg agcccaatcc cactggtgcc    5700
cacagccacc cagtgctgtg gacagaggtt ggggcaccct tccaggtctc tcctggtcac    5760
actggagccc tcataggcct ccttcgtcct gcctctagac caaccttcat acatgccact    5820
ccttaccccc acaccaatta tcccttgctc ctcctggtcc ctcctccagg gctactcact    5880 ccctttttcta cccctctctc agtctatcct ctgtgtggac agactgagct tctaaaacac    5940
agacatgatt tacaactcct ttccttccta ttctgggcac ttaggaagtg tatataaagt    6000
ccttaaaatg aaccaaagca acagatagtt ccttccctcc ttgaacagat agggttccaa    6060
agtggctggt ctaagggtgt cagcttcagg acctccctct gttaaagagc ctgggaggaa    6120
ggcaggcagg atctgggaga ctggagggg gctaggctga gactgatccc catttcgccc    6180
caggaagtga atgaattgtg tcagtcggtg caggagcatg tggagctgct gggctgtggg    6240
gctgggcccc agggtgaagc cgctgtgcgc caggccgagg atgccatcca aaatgccaac    6300
```

```
ttctctctca gcgtgagcac tccccctcct gctacaagga cccttcccct cttagtcagg    6360
tgtcagctcg caactgcttt tcctctttgg ccctcagatt ctccccattc tatatgaagc    6420
tggaagctcc ccaagccatc actggcagct tgggcagaag ctggagggcc ttctgagaca    6480
ggtgggcgag gtctgccgcc aggacatcca ggtgagaggg tactcctgcc ccaaccccac    6540
ctccgtttgc aggtttgact cccatccttt agttttaact gtgatatccc ctgactcaat    6600
attctgttgg agttggagcc tcaagccagc agcctggtgt ctggccacat cctcaccatg    6660
ctctgactga cctttgtcta ggacttcact caggccacac tggacacagc aaggagcctc    6720
tgcccacaga tgctgcaggg atccagctgg agggagcagc tagaggggt cctggcaggc     6780 tcgaggggcc tcccggagct gctcccagag cagctgctgc aagatgcctt cactaggctc    6840
aggtaggctg gatggggctg ggctgggcaa ggctgagcaa agccagccca ttaacccctg    6900
tcctctcctg cccttaggga catgcggcta tcaatcacgg ggaccttggc agagagcatt    6960
gtggctcagg ctttggcagg cctgagtgca gcccgggatc agctggtgag ggggagatgt    7020
gcacacactt tcgtgcaaac acacacatgc agtgacttgg ccatctccct gcagggggct    7080
ctgtaatgtc ttctggggtc atgtagccca gggctatttc agggtcccct tagttagcat    7140
caatgggatc atggctgagg ccctacctgc catctttggc tgcttggtat tgcaggtgga    7200
gagtctggct cagcaggcaa cagtgacaat gcccctgcc ctaccagcac cggatggagg     7260
tgagcccagc ctccttgagc ctggggaatt ggaaggtctt ttcttcccg aggagaagga     7320 agaggagaag gagaaggtaa gtggttttag aacacggggc atggcactcc cagtcttccc    7380
atcttgctgt ggagtgtgga aggtgaaagg cagctctttt ggttggtgc tctcctaccc     7440 caggctgagt ttgtgccctc cccaccagga tgacagtcct ccacagaaat ggcctgagct    7500
cagccacggt cttcacctgg tccccttcat tcacagtaag tcaggccttt ggggagggga    7560
gtttacgtgg gtgggctgaa gctccattag acttgggac ccggggacct ggatgaactc      7620
attcagcctt gtctgggtac ccaccagccc ttgactgggc caggtcgggc ccttgtgca     7680 acctgcaaag ctggggtctg ctgtggtcag cccggggcgg gacctgggcg gatctgggac    7740
aggacaccgg ctcagctcgc ctccccgcgc ccctttccct accccaggga cgcgcatgct    7800
gggcggcggc gcggagccgc gcgcgctcgg ggccgcgctc agcaccacgg acagcggcgg    7860
cggcggggga ggggcggagg ggcagagggg cgggggacg ggcggcgtag ccgggccct      7920 ccccgcgccc tgggcgggtc ccccgccgcc ctagcgcctc cgccgccacc tccccgggct    7980
cggcgctcgg tgctcttctg gtgctgtccc ctcaggtgct gctgaggaag cggagccgga    8040
gcccgagctg gcggctccgg gagaagatgc agagccgcag gcggggccgt ccgcgcgcgg    8100
ctctccgagc cctgccgccc ctgggccccc ggccggcccg ctgccccgca tggacctgcc    8160
actggcgggg cagcccctgc gccatccgac ccgggcccgg ccgcggccgc gccgccagca    8220
ccaccaccgc ccgccgccgg ggggccccca ggtgagcacc cttcccccac tccggagcgc    8280
gtggaattgg ggatcacggg tggcccggcc gctcctcatg ggtggtagcg gtcaaggaga    8340
gggggtggtg ggggcccaag gccacctggt cgtgcggccg cggtcacatc ctggcttctt    8400
cctgaccacc cccacccca ggccatgcct gtgcgggacc atgggtgtgc gggttccgtt      8460
cggggtgtgc ctgggtgtgg gactccgtct cggggcggcc cgcggcctcc gtggctgcgc    8520
gagagagggt gtccgtcctc cctccctccc ccggggctgc tgagagatgc cgggcagccg    8580
ggtagccgag ccgcggggcc aagcctgcgt ctgctgcgcg tccggcggcg cgcgtgtgg     8640 ggagatgcgt gtgtgggctg caagcccgcg ggggcagcgg gcactggcgg agggcgggga    8700
```

```
ggagccggct tgaggccccc cagagggtct gacgcagcag ccggcgccac tgagccggca    8760
gcaggccggg tggagtgggg gtggggtggg ggacactgca gggaactgtt cggagcagag    8820
ctggtggcaa gtgggaacgg gtgacccegg gggcacgtga gggctaggtt tgctggtgac    8880
cgggtggctc gggcgtgtag gatactctgt ggacaagga cgggtgtgga ctgggtgtgc     8940
gggagccagc agcgagtgag gagtgcgtga aatctggagt ctctgtccag cagcaggaca    9000
gtaggaggct ggtatcagca gcccctaggg tcaccccagt ctggaatcct ggagttattc    9060
agtccaggct gccggccggg ggggggggg ggtagaagcc agagttgcac tcaaccctga     9120 ccctgaccc catgatgccc cccaggtacc cccagccttg ccgcaggaag ggaatgggct     9180 cagtgccgc gtggacgagg gcgtggagga attcttctcc aaaaggctga tccagcagga     9240
tcgcctgtga gtgaggggca tctgctgggg gtgggagagg gtgggatgcc tgatgggctt    9300
tctcgctcac tgctgggtgt ccccacagct gggcccccga ggaggacccg gccactgagg    9360
ggggcgccac tcctgtcccc cgtacactgc gaaagaagct gggcaccctc tttgccttca    9420
agaagcctcg ttcaacgcgg ggtccacgga ctgatctaga gaccagccct ggggcagctc    9480
cccgaacccg aaaaactaca tttggcgacc tactgcggcc gccaacccgt cccagccgtg    9540
gtgaggagct tggtggggct gaggggggaca ccagcagccc tgaccctgcc ggcaggagcc   9600
gacctcgcta cacaagagat agcaaggcct actcgatgat actgctgcct gccgaggagg    9660
aggcaacgct gggtgccaga cccgacaagg tgaggcttgc tgatggggggg tggtgaaggc   9720 gcttctggga cccagggcgc ggactgtctc caactcgagc atctctgtcc ctagcggcgg    9780
cccctggagc ggggagaaac agaactggct ccatcctttg aacagcgggt acaagtaatg    9840
ctgcaggaga taggcgtcag ccgaggcagc gggggtgccg aaggcaagag gaagcaagtg    9900
agttgagggg acctgagcat gaagtgagag ggcagatggc atgctgtggg tgacataagt    9960
gaccaagatg gaggagactc atgacagata ggtctaattg tcagttctac tccattctcc   10020
tcgaaatggt tacagattcg acctttcttc cctcttggct ttgacccagg cacaggccac   10080
cagcatctcc tctttggacc tgagaaagtc ttttctctgc aggtctaata gaaatctgag   10140
gcctgggcca ggcgccatgg ctcacgcctg taatcccgac actttgggag gctgaggcag   10200
gtggattacc tgaggtcagg agttaagaga ccaacctggc caacatggtg aaaccctgtc   10260
tctactaaaa atacaaaaat tagccgggtg tggcggtggg cacttgtagt cccagctact   10320
tgggagggtg aggcacgaga attgcttgaa cctgggagac aggttgcagt gagcctagat   10380
cgtgccacta cacactagcc tggacaacaa gagtgagact catctcaaaa aaagaaaaag   10440
aaaaaaatct gaccttgtca cttgtgcttg aaatagcaag tcctccaggg gcttcctctc   10500
aagacactgt tcagactcca caacctgctt cagagccctg tggggtcttg gcctggcca    10560 ccttaaaacc tcactgcttt cctcccctgg tgcaaatcag agcctccaca cacgtccctg   10620
ggtggtctgg atgtcctccc tgcctcgctt ccagtctcta attgtgggtt acgccaggtc   10680
cctcctcagc catccctgca gtgcccatgg ttcttccctg actctcctct gtgggccacc   10740
ctgctaatgt ctctctcatt agagtcccaa agaaccccag ccctccatac catccattca   10800
atatcttaaa aaacaaaaaa caaaacaaa caaaaaacat gaagtcggcc tgaatttaga   10860
aatattcaag tgtgcaaaga gttctaagag ggctgtactg ggtttgccat gttcttgtcc   10920
agcccatggt gggcattcag tggcaggatt ataagaacaa gaacgaacaa aaggctaggg   10980
tgtggggagc gggcagggct ggaatctgat tgccctgttt cctgcagagc aaagatggcg   11040
```

-continued

```
agatcaagaa agctggctca gatggtaagt gggaccctgg ggtgtggcag tacatttgcc    11100
aggaggtgtc cttatagaca gcccccaagg cacttgctct ccttggggag gaagggga     11160
ggccaggttt ttcttcccct cacctccaag gtctggtacc tgagtcccca gctccgcctt    11220
gcaggtgaca ttatggacag ttccacggag gcccctccca tctcgatcaa gtcccgcacc    11280
cactctgtgt ctgctggtga gtgagggcca ctgtgtgtgt tggtagtggg agcagggaca    11340
ggcaggagtt gggtcagact gttgttcaga cctatcgcca atgcctgacc aggtcttggc    11400
tgacaccttt ctccctacag accttcctg cagacctggc ccagggagcc aggggcctga    11460
gtctgccacc tggaagacac tggggcagca gttgaatgcg gagctcagga gccgtggttg    11520
gggccaacag gatggtccag gccctccctc ccctggtcaa agcccaagtc cctgcagaac    11580
cagcccctcc ccagacagcc tgggcctccc agaggaccct tgcttgggcc cagaaaatga    11640
aggtaggcag gcacctgatt ccccaccca atcctggcct cggggctgga ggagttcctg    11700
ctgggaactc agctcctcta aggacccga gggtgggagg caaggctgg agtgggggca    11760
gctgttggaa taccctgat tccctggcct ccctcagatg ccagctgag gccgaggcct    11820
ctctcggcag ggcggcgagc agtgtctgtg catgaggacc agctccaggc ccctgctggt    11880
gaggggagac acctccacgt gtgcttgaat gcaggagatg tgggagggtg ggcttctggg    11940
gctcccttca tagctttggt ccttggaggg agccaccagt gtgtgaggtc tcaagaaatc    12000
agggagccaa agaccaggt gcaagggttt gacagcaagc ccttccaact agcactggct    12060
ccacttcccg aagagcagcc tctgccaggg gtgaggacgc agggacgggg gatgctctga    12120
aggcagcagt gtgtgtgagt gcatgcttat gtgcactgga ggtggaagag aggggcaggg    12180
gatggacaga ccccaagcct tagcaaccca ccccaagcct ttctgtgtcc cttagaacgg    12240
cccctgagcc tgcagcgctc cccgtcctc aaacgcaggc caaaactcga ggcacctcca    12300
tccccaagcc taggtaagag ggggtccagg ccagctggga gggtggcagg actgcttagc    12360
ccagccctga cccttcctct ctctccctcc ctccccttcac aggatctggc cttggaaccg    12420
agcctctgcc cccacagccc acagagccct ccagccctga gcggagccca ccctccccag    12480
ccacagacca aagaggcggc ggccccaatc cctgatcctc tcctctcctg ccgcatgaga    12540
ttatttatt aaaaaactca aaggaa                                         12566
```

<210> SEQ ID NO 6
<211> LENGTH: 1435
<212> TYPE: PRT
<213> ORGANISM: Homo sapiens

<400> SEQUENCE: 6

```
Met Ala Gln Thr Pro Asp Gly Ile Ser Cys Glu Leu Arg Gly Glu Ile
 1               5                   10                  15

Thr Arg Phe Leu Trp Pro Lys Glu Val Glu Leu Leu Lys Thr Trp
                20                  25                  30

Leu Pro Gly Glu Gly Ala Val Gln Asn His Val Leu Ala Leu Leu Arg
            35                  40                  45

Trp Arg Ala Tyr Leu Leu His Thr Thr Cys Leu Pro Leu Arg Val Asp
        50                  55                  60

Cys Thr Phe Ser Tyr Leu Glu Val Gln Ala Met Ala Leu Gln Glu Thr
 65                  70                  75                  80

Pro Pro Gln Val Thr Phe Glu Leu Glu Ser Leu Arg Glu Leu Val Leu
                85                  90                  95

Glu Phe Pro Gly Val Ala Ala Leu Glu Gln Leu Ala Gln His Val Ala
```

100                 105                 110
Ala Ala Ile Lys Lys Val Phe Pro Arg Ser Thr Leu Gly Lys Leu Phe
            115                 120                 125

Arg Arg Pro Thr Pro Ala Ser Met Leu Ala Arg Leu Glu Arg Ser Ser
        130                 135                 140

Pro Ser Glu Ser Thr Asp Pro Cys Ser Pro Cys Gly Gly Phe Leu Glu
145                 150                 155                 160

Thr Tyr Glu Ala Leu Cys Asp Tyr Asn Gly Phe Pro Phe Arg Glu Glu
                165                 170                 175

Ile Gln Trp Asp Val Asp Thr Ile Tyr His Arg Gln Gly Cys Arg His
            180                 185                 190

Phe Ser Leu Gly Asp Phe Ser His Leu Gly Ser Arg Asp Leu Ala Leu
        195                 200                 205

Ser Val Ala Ala Leu Ser Tyr Asn Leu Trp Phe Arg Cys Leu Ser Cys
    210                 215                 220

Val Asp Met Lys Leu Ser Leu Glu Val Ser Glu Gln Ile Leu His Met
225                 230                 235                 240

Met Ser Gln Ser Ser His Leu Glu Glu Leu Val Leu Glu Thr Cys Ser
                245                 250                 255

Leu Arg Gly Asp Phe Val Arg Arg Leu Ala Gln Ala Leu Ala Gly His
            260                 265                 270

Ser Ser Ser Gly Leu Arg Glu Leu Ser Leu Ala Gly Asn Leu Leu Asp
        275                 280                 285

Asp Arg Gly Met Thr Ala Leu Ser Arg His Leu Glu Arg Cys Pro Gly
    290                 295                 300

Ala Leu Arg Arg Leu Ser Leu Ala Gln Thr Gly Leu Thr Pro Arg Gly
305                 310                 315                 320

Met Arg Ala Leu Gly Arg Ala Leu Ala Thr Asn Ala Ala Phe Asp Ser
                325                 330                 335

Thr Leu Thr His Leu Asp Leu Ser Gly Asn Pro Gly Ala Leu Gly Ala
            340                 345                 350

Ser Glu Asp Ser Gly Gly Leu Tyr Ser Phe Leu Ser Arg Pro Asn Val
        355                 360                 365

Leu Ser Phe Leu Asn Leu Ala Gly Thr Asp Thr Ala Leu Asp Thr Val
    370                 375                 380

Arg Gly Cys Ser Val Gly Gly Trp Met Thr Gly Arg Ala Asp Trp Arg
385                 390                 395                 400

Ala Gly Arg Gly Gly Leu Gly Pro Pro Ala Gly Val Ala Asn Ser Leu
                405                 410                 415

Pro Pro Gln Leu Phe Ala Ala Val Ser Arg Gly Cys Cys Thr Ser Leu
            420                 425                 430

Thr His Leu Asp Ala Ser Arg Asn Val Phe Ser Arg Thr Lys Ser Arg
        435                 440                 445

Ala Ala Pro Ala Ala Leu Gln Leu Phe Leu Ser Arg Ala Arg Thr Leu
    450                 455                 460

Arg His Leu Gly Leu Ala Gly Cys Lys Leu Pro Pro Asp Ala Leu Arg
465                 470                 475                 480

Ala Leu Leu Asp Gly Leu Ala Leu Asn Thr His Leu Arg Asp Leu His
                485                 490                 495

Leu Asp Leu Ser Ala Cys Glu Leu Arg Ser Ala Gly Ala Gln Val Ile
            500                 505                 510

Gln Asp Leu Val Cys Asp Ala Gly Ala Val Ser Ser Leu Asp Leu Ala
        515                 520                 525

```
Asp Asn Gly Phe Gly Ser Asp Met Val Thr Leu Val Leu Ala Ile Gly
        530                 535                 540

Arg Ser Arg Ser Leu Arg His Val Ala Leu Gly Arg Asn Phe Asn Val
545                 550                 555                 560

Arg Cys Lys Glu Thr Leu Asp Asp Val Leu His Arg Ile Val Gln Leu
                565                 570                 575

Met Gln Asp Asp Asp Cys Pro Leu Gln Ser Leu Ser Val Ala Glu Ser
            580                 585                 590

Arg Leu Lys Leu Gly Ala Ser Val Leu Leu Arg Ala Leu Ala Thr Asn
        595                 600                 605

Pro Asn Leu Thr Ala Leu Asp Ile Ser Gly Asn Ala Met Gly Asp Ala
610                 615                 620

Gly Ala Lys Leu Leu Ala Lys Ala Leu Arg Val Asn Ser Arg Leu Arg
625                 630                 635                 640

Ser Val Val Trp Asp Arg Asn His Thr Ser Ala Leu Gly Leu Leu Asp
                645                 650                 655

Val Ala Gln Ala Leu Glu Gln Asn His Ser Leu Lys Ala Met Pro Leu
                660                 665                 670

Pro Leu Asn Asp Val Ala Gln Ala Gln Arg Ser Arg Pro Glu Leu Thr
                675                 680                 685

Ala Arg Ala Val His Gln Ile Gln Ala Cys Leu Leu Arg Asn Asn Arg
690                 695                 700

Ala Asp Pro Ala Ser Ser Asp His Thr Thr Arg Leu Gln Pro Leu Gly
705                 710                 715                 720

Leu Val Ser Asp Pro Ser Glu Gln Glu Val Asn Glu Leu Cys Gln Ser
                725                 730                 735

Val Gln Glu His Val Glu Leu Leu Gly Cys Gly Ala Gly Pro Gln Gly
            740                 745                 750

Glu Ala Ala Val Arg Gln Ala Glu Asp Ala Ile Gln Asn Ala Asn Phe
        755                 760                 765

Ser Leu Ser Ile Leu Pro Ile Leu Tyr Glu Ala Gly Ser Ser Pro Ser
770                 775                 780

His His Trp Gln Leu Gly Gln Lys Leu Glu Gly Leu Leu Arg Gln Val
785                 790                 795                 800

Gly Glu Val Cys Arg Gln Asp Ile Gln Asp Phe Thr Gln Ala Thr Leu
                805                 810                 815

Asp Thr Ala Arg Ser Leu Cys Pro Gln Met Leu Gln Gly Ser Ser Trp
            820                 825                 830

Arg Glu Gln Leu Glu Gly Val Leu Ala Gly Ser Arg Gly Leu Pro Glu
        835                 840                 845

Leu Leu Pro Glu Gln Leu Leu Gln Asp Ala Phe Thr Arg Leu Arg Asp
850                 855                 860

Met Arg Leu Ser Ile Thr Gly Thr Leu Ala Glu Ser Ile Val Ala Gln
865                 870                 875                 880

Ala Leu Ala Gly Leu Ser Ala Ala Arg Asp Gln Leu Val Glu Ser Leu
                885                 890                 895

Ala Gln Gln Ala Thr Val Thr Met Pro Pro Ala Leu Pro Ala Pro Asp
            900                 905                 910

Gly Gly Glu Pro Ser Leu Leu Glu Pro Gly Glu Leu Glu Gly Leu Phe
        915                 920                 925

Phe Pro Glu Glu Lys Glu Glu Lys Glu Lys Asp Asp Ser Pro Pro
930                 935                 940
```

```
Gln Lys Trp Pro Glu Leu Ser His Gly Leu His Leu Val Pro Phe Ile
945                 950                 955                 960

His Ser Ala Ala Glu Glu Ala Glu Pro Glu Pro Glu Leu Ala Ala Pro
                965                 970                 975

Gly Glu Asp Ala Glu Pro Gln Ala Gly Pro Ser Ala Arg Gly Ser Pro
            980                 985                 990

Ser Pro Ala Ala Pro Gly Pro Pro  Ala Gly Pro Leu Pro Arg Met Asp
        995                 1000                1005

Leu Pro Leu Ala Gly Gln Pro  Leu Arg His Pro Thr  Arg Ala Arg
    1010                1015                1020

Pro Arg Pro Arg Arg Gln His  His His Arg Pro Pro  Pro Gly Gly
    1025                1030                1035

Pro Gln Val Pro Pro Ala Leu  Pro Gln Glu Gly Asn  Gly Leu Ser
    1040                1045                1050

Ala Arg Val Asp Glu Gly Val  Glu Glu Phe Phe Ser  Lys Arg Leu
    1055                1060                1065

Ile Gln Gln Asp Arg Leu Trp  Ala Pro Glu Glu Asp  Pro Ala Thr
    1070                1075                1080

Glu Gly Gly Ala Thr Pro Val  Pro Arg Thr Leu Arg  Lys Lys Leu
    1085                1090                1095

Gly Thr Leu Phe Ala Phe Lys  Lys Pro Arg Ser Thr  Arg Gly Pro
    1100                1105                1110

Arg Thr Asp Leu Glu Thr Ser  Pro Gly Ala Ala Pro  Arg Thr Arg
    1115                1120                1125

Lys Thr Thr Phe Gly Asp Leu  Leu Arg Pro Pro Thr  Arg Pro Ser
    1130                1135                1140

Arg Gly Glu Glu Leu Gly Gly  Ala Glu Gly Asp Thr  Ser Ser Pro
    1145                1150                1155

Asp Pro Ala Gly Arg Ser Arg  Pro Arg Tyr Thr Arg  Asp Ser Lys
    1160                1165                1170

Ala Tyr Ser Met Ile Leu Leu  Pro Ala Glu Glu Ala  Thr Leu
    1175                1180                1185

Gly Ala Arg Pro Asp Lys Arg  Arg Pro Leu Glu Arg  Gly Glu Thr
    1190                1195                1200

Glu Leu Ala Pro Ser Phe Glu  Gln Arg Val Gln Val  Met Leu Gln
    1205                1210                1215

Arg Ile Gly Val Ser Arg Gly  Ser Gly Gly Ala Glu  Gly Lys Arg
    1220                1225                1230

Lys Gln Ser Lys Asp Gly Glu  Ile Lys Lys Ala Gly  Ser Asp Gly
    1235                1240                1245

Asp Ile Met Asp Ser Ser Thr  Glu Ala Pro Pro Ile  Ser Ile Lys
    1250                1255                1260

Ser Arg Thr His Ser Val Ser  Ala Asp Pro Ser Cys  Arg Pro Gly
    1265                1270                1275

Pro Gly Ser Gln Gly Pro Glu  Ser Ala Thr Trp Lys  Thr Leu Gly
    1280                1285                1290

Gln Gln Leu Asn Ala Glu Leu  Arg Ser Arg Gly Trp  Gly Gln Gln
    1295                1300                1305

Asp Gly Pro Gly Pro Pro Ser  Pro Gly Gln Ser Pro  Ser Pro Cys
    1310                1315                1320

Arg Thr Ser Pro Ser Pro Asp  Ser Leu Gly Leu Pro  Glu Asp Pro
    1325                1330                1335

Cys Leu Gly Pro Arg Asn Glu  Asp Gly Gln Leu Arg  Pro Arg Pro
```

```
                1340              1345              1350
Leu Ser Ala Gly Arg Arg Ala Val Ser Val His Glu Asp Gln Leu
    1355              1360              1365

Gln Ala Pro Ala Glu Arg Pro Leu Arg Leu Gln Arg Ser Pro Val
    1370              1375              1380

Leu Lys Arg Arg Pro Lys Leu Glu Ala Pro Pro Ser Pro Ser Leu
    1385              1390              1395

Gly Ser Gly Leu Gly Thr Glu Pro Leu Pro Pro Gln Pro Thr Glu
    1400              1405              1410

Pro Ser Ser Pro Glu Arg Ser Pro Pro Ser Pro Ala Thr Asp Gln
    1415              1420              1425

Arg Gly Gly Gly Pro Asn Pro
    1430              1435

<210> SEQ ID NO 7
<211> LENGTH: 12186
<212> TYPE: DNA
<213> ORGANISM: Mus musculus

<400> SEQUENCE: 7
```

| | | | | | |
|---|---|---|---|---|---|
| ccgagtacgc | ggaaggaaaa | gtccctgagc | gacagcaaca | gtcaagattc | gaccatcctc | 60 |
| ccacaacctc | ccacccgggg | cgaactcagc | caacgaagcc | ggggcgggga | ggggccgggc | 120 |
| cggggggcggc | ctggcaggaa | gaagcgcgta | ccttccgctg | caggaggagc | aggtggctgc | 180 |
| actgctgcct | gggcccctgg | cttcctgtgt | acgctcctgc | cggctgcttt | tcccgccag | 240 |
| agctcattgg | gccgtcccgg | ccctatggca | cagaccccag | acgacatatc | ctgtgaactg | 300 |
| cgaggtaagc | cctgggagcc | cacctggcca | tgaagagcct | gactccaaac | cagacctctc | 360 |
| ctctcggcgc | cttagggaac | ttgaccaggg | gttttgttc | tggagggagg | gccagtgcct | 420 |
| aaaagtccgc | ttcatttctt | cctagctgat | ccacacatga | atacctgggc | actcagtcta | 480 |
| gcacagacct | tgggcacaga | gtggccctaa | tagaggagcc | aaagtcaccc | agtagactgt | 540 |
| cttccacag | gcgagatcac | caggttcctg | tggcccaagg | aggcggagct | gctgttgaaa | 600 |
| acctggcttc | cccaggaggg | tgccgagcaa | agccatatcc | tggtatggta | gccaggagtg | 660 |
| aagctcagga | cagtggccag | accctgcaca | agaaacttg | atttccctag | agtattagtc | 720 |
| ttttgtctcc | ccccaggcac | tgcttcgatg | gagggcatat | ttgctgcaca | cctgccttcc | 780 |
| cctgagggtg | agtcccaggc | cgggccaaca | ccccttcccc | ttcagcaagg | gactgccttg | 840 |
| cgcagctgtc | ttctttgccc | atgctggctt | ttactttcca | acagcagaca | ggagggaagt | 900 |
| ctgggcaggt | ctagctcagg | atgccacaaa | atcatgggct | gtggagagag | gacctgggtt | 960 |
| caattctccc | accaccaggt | gggctcacaa | gtggttggaa | ctctagttcg | aaggcaccca | 1020 |
| ccaccgtctt | ctggcatctt | tgggaaccag | gcacacaaga | gtggtacaga | gacaaacatg | 1080 |
| ccagcaaaca | cccaatagta | caattttaa | attttaagaa | caagctagga | ggtggtggtg | 1140 |
| cacgccttta | gtcctggcac | tagggagaca | gaggcaggca | ggcctggtct | acagagtgag | 1200 |
| ctccaggaca | gccaggtcta | cacagagaaa | ccctgtctca | ggaaagagaa | agaaagaaag | 1260 |
| aaagaaagaa | agaaagaaag | aaagaaagaa | agaaagaaag | aaagaaagaa | aacgaactag | 1320 |
| gctcaagaga | | | | | |
| gtagcaacag | tcagttggaa | tgactctgat | gctttccagg | tggactgtac | attcagctac | 1380 |
| ctggaggtcc | aggccatggc | actacaggaa | acaccccctc | gggtaagaaa | gctggacccc | 1440 |
| aacttgaaca | tacactccgc | ttgatcattt | attcctacac | atatcactct | gaatggacag | 1500 |
| cgcttccacc | acacagggat | ccaaaaggct | cctccttccc | caggtcacct | ttgagctgga | 1560 |

```
gtccctgcct gaactggtcc tggagtttcc ctgtgtggct gccctcgaac agctggctca    1620
gcatgtagct gctgccatca aaaaggtctt ccctcgctca acccttgggt gaggcttaga    1680
aaatccaagg ggtggggcag ggcctcagtg aaagcttttc atccttcaag gagctagaag    1740
tcccttttgc ctcttctcct tatccctgc ctaggaagct attccggaag cccacaccct    1800
cgtctctgct ggctcgactg gagagaagcc atcccttaga gtccaccata cccagcagtc    1860
cgtgcggtga gggccaagtc agagccgcat aaaccttcca gtttgcctcc atgcaatcct    1920
agtctcttgg tattgggggg gctccccaaa gtgaacaggg ccactttat cactgccgcc    1980 atctactatg gggctgacct tcccctgtct ctgacttagt gcctgtctgt ttccctatca    2040
ctcccccgac acctctctag gtggcttctt ggaaacatac gaagctctgt gcgattacaa    2100
tggcttccca ttccgagagg agattcagtg ggtgagggta gggcccttt ggggagttc    2160 tggggatgtt tgacgcccct tgtgtgtgct aagcccctct acccttttgtg gccccaggct    2220 agctgtgact tttttctttt acatctagga tgtggacact atctaccatc gccagggctg    2280
ccgccacttc tgccttggag atttcagcca ctttggcagc cggtatgagg ccagccagga    2340
ttgggaggcg agaactccag cacccaaatt cctagtctgt ctgtagaggg gggatgctga    2400
ctgagccctg tgtttggaag gccctgagca ctgcattttc tcttccccgc gatagagacc    2460
tggctttgag tgtagctgcc ttatcttata acctgtggtt ccggcgcctc tcctgcgagg    2520
acatgaagct ggtgagagag tacacacaaa agggagtgcc aagggtgtaa gggtcaaagt    2580
tcaacctgat gagtcacgac cctcttgctc tcagagcctg gaggtctcag aacagattct    2640
gcacatgacg agtcaatctt cctatttgga ggagctggtg ttggaggctt gtggtctgcg    2700
agggtgagag gcctgagctg ggcgtgggaa cctgtgatct gcggagagac tgggaatcag    2760
tcttaactgg ggtcttggtc ctcagagact tcgttaggcg actagcccag gccctggcag    2820
gacattttaa ttctggactt cgggagctca gcctgtctgg gaacttgctg gatgacagag    2880
gtatggcaga atctgggaga cccaaggcag ccgagccgga agaggtgagg ttcacagagc    2940
tgctctgtcc acaggtatgg ctgcactcag cagacaccta gagcattgtc caggagcctt    3000
gaggagactc agcctagcac agacaggctt gacacctcga ggtgggtggg actggggagg    3060
gttgggaggg ctcgaggtaa ggtgagcatg tcttgatact cagccgctcc tcccacccac    3120
caccaggaat gagagctcta ggcagggcac tggcaacgaa tgccaccttt gactctaccc    3180
tgacccacct ggatctttct gggaaccctg gggcactggg accctcacag gatagtgggg    3240
tgagtagcag tttttaaagt cagaaactgg gacggccgag tcagtgggat gccagatcct    3300
taggcaaccc ctgcctccct ctctccctcc gtagggcctg tatactttcc tgagccgtcc    3360
taacgtcctg gcgtatttga atcttgcagg cactgacgcc acgctaggca cggtaagagt    3420
gtggtcatgg gggatgcgtg gcagggcttg gctgcgcctg agcagggaag gaaggagagc    3480
ggagcgtggc agagaaagcc agggcttctg gaaggttatc gctaatacca ccttcctctc    3540
agctcttcac ggccttagct ggtggctgct gctccagcct cacccatctg gaagcttcaa    3600
ggaatatctt ctctcgcatg taaggggcac caggcaggct cggaaggacg aggcttgagg    3660
gtatcagctc ccctgagcgt aaatcccact tctgctctcc accctcacc gcaggaagtc    3720 ccaagcggca ccagccgcgc tgcaacgctt ccttggcggt accaggatgc tacggcacct    3780
gggcctggcg ggctgcaagc tgccacctga agcgctcagg tcagtcctcc cgtgcagtca    3840
caaccttgag cagtgtctct tgacctctac tgcctcaccc ctctatgaca cccataatct    3900
```

```
ttcgtaaccc caacctgcct ggcgcttatt cgttcgcacc gagtcccgtg ttcccagatc    3960
ttgtcacctg tgtgttaccc ctctctcagg gcccttctag aaggtcttgc actcaacact    4020
cagatccatg atctgcacct agacctcagc gcgtgtgagg taggtacccg gtcctggttg    4080
tgagctgaga gcacgtccac attattgaga gtgaggctgg gaggccttcc ctacccaggc    4140
ataatcctga gtgcacccta cctccacctc cagctccgct ccgtgggtgc ccaggtgata    4200
caagacttgt tttgtgatgc gggtgccttg agttccttgg atctgtcgga taatggtgag    4260
gccgccaggg aacccatcca tccatgctcc tgttatttgt accagatccc cagggtgggc    4320
accctgacct ggtaggagtg atttgtgcat cactctggtt accctaggc tttggctccg    4380
acatggtgac actggtgctt gccatcggga ggagccggtc tctgaaacac gtggcccttg    4440
gaaggaactt caacgttcgg tgcaagtgag tcccaagctt cccctgtac ctctcaagaa    4500
ggactgcatc acccatttag ttccctaaca gcagccctt tccacaggga gaccctggac    4560
gatgtcctgc atcggatagc ccagctaatg caggatgacg actgtgtgag ttcacagagc    4620
cctgtggggg gtcctcaagc aattaacgtc ttgtaatgct tcttatgtat attccttcaa    4680
accttctttg ctgaacctga gcccatgtat ccatcagtgc cttccttta accccagcct    4740
ttgcagtcac tatccgtggc tgagtcgcgg ttgaagcagg gtgccagcat cctgatccgg    4800
gctttgggca ccaatcctaa actgacagcg ctggatatca gtggcaatgc catagggat    4860
gctggggcca agatgctagc caaggctcta cgcgtcaaca ccaggctacg gtgggtatga    4920
tcatgataag ggctgggacc cgcaggagag ggcaagagtt atataataga cgggtgtatg    4980
ggtttaaggt atacatggtg atgagacagg tgattggata aggccagagg gttgggcggg    5040
gttctgcccc tgctgaagcc tggtggggcc caggtctgtg atctgggacc ggaacaacac    5100
atctgctctg ggcctgctgg atgtggcgca agccctggaa cagaaccaca gcctcaagtc    5160
catgccgctg ccactgaatg acgtaaccca ggctcatcgc agccggccag aactcacaac    5220
tcgagcggtc catcaggtgg gggtccgcgc ttctctctgc ccttttgtgt gtggtgactc    5280
cacccctgg cgtttctcac tatctctttg actgcagatc caagcctgtc tctggaggaa    5340
caaccaagta gactctactt cggacctcaa gccctgcctt cagcccttag gtctgatttc    5400
agaccactca gagcaggtta gtgccccttg ccctaatctt gaatacctga gcacctgagt    5460
cagagtctga cttttctgag ccacagtgct gagttctatg tctcaaacaa tttccttttc    5520
ttggtcaccg ttcttgaaac agcttcccgt gtaacatttg gctgctttaa gggtttaaat    5580
aggctgtcct tgctgtagcc tctttattcg acttcctatt taagggctaa cctctctta    5640
ctgactgtgt ggctagctcc agcagtccta tctctggctt taatttcctt tcattaaccc    5700
atctttttgt attattctta cctctgcatt cccaagcctc aattcttttg tttggtttg    5760
gtttcttgag acagggtttc tctgtgtagc ctgggatatc cttgaactcc cagagatctg    5820
cttgcttctg cctcccaagt gctaggatta aaggcatgtg ccaacactgc ccagcccaag    5880
ccttgattga ttgattgatt gattgattga ttgatttgag acagggtttc tctgtgtaat    5940
ccttgccgtc ttggaattca ctctgtagac caagctggcc tcgaactcag aaatccgcct    6000
gcctctgcct cccaagtgct gggattaaag gcgtgcgcca ccatacacac acacatacac    6060
acaactgttc tctgtatgga tggttaaggt gacatctttg aaatcagagt gaccaaagct    6120
tctttccttc ctgttttagg cctggagaaa ataatcaagt gatcagatag ggtttccctc    6180
acagtttgtc ttcctgtagg aaaaccttgg aaggagacag gcagaatcg gggagactga    6240
tgagaaacaa agggaggact aatccatgac tccctcctgc ctgcccccca ggaggtgaac    6300
```

```
gagctatgcc agtcagtaca ggagcatatg gagctgctgg gctgtgggc tgggcccag    6360 ggtgaggttg ccgtgcacca ggctgaggac gccatccaga atgccaactt ctctctcagt   6420
gtaagcaccc tctttcctgc tctgaggacc tttccgctcc caatcatgtg ccagtttgca   6480
agtccttttg ttccttggcc tccccagatc ctccccattc tctatgaggc tgggagatcc   6540
ccaagccacc actggcagct gcagcagaag ctagagagcc tcctgggtca ggtgggcgag   6600
atctgccgcc aggacatcca ggtaagatac tagtcctgcc ccagccgcac ctccccatgc   6660
aggcttgacc ctcattccac acgcttgtct gggataggcc cttagtcagc agtggtttaa   6720
tgggaactca caccttcaaa gccaaagggg ctgggttttg gcatactgct aacattttgt   6780
aacctttgcc caggacttca ctcagaccac cctggatacc acaaggagcc tctgcccaca   6840
gatgttgcag acacctggct ggaggaagca gctagaggga gttctggtgg gctccggggg   6900
cctcccagag ctgcttccgg aacatctgct gcaagatgcc ttctctaggc tgaggtgagc   6960
aagcccaact gggctgggca atgctggaca gagacagcac actaatcctc actgtctcct   7020
gcctttaggg acatgcgcct gtcaatcact gggaccctag cagagagcat tgtggctcag   7080
gctcttgcag gtcttcatgc agcccgagat cgactggtga gggggaagct ttgaacacat   7140
ttcatagagt aacttgttta accctcacgg gcaaccctga aatgacttct ggggtcataa   7200
gctagctact tagttctgcc tatctttggg tggcctggta ttacaggtgg agaggctaac   7260
tcagcaggca ccagtgacca tggcccctgc tgtaccacca ctgggtggaa atgagctcag   7320
cccccttgag actgggggat tggaagagct tttctttccc acggagaagg aagaggagag   7380
agaaaaggtg agtgtcttca gaatttcaag cctaggaccc cggctggctt tctccttctt   7440
gctctggaat gtagaaggtg aggagcaggt ctgggtcatc ctaaccctag actgaggctg   7500
tacccatccc accaggatga gagttcttca tggaaatggc ttgagcctag taactgtttt   7560
cacctggtct cctcccttca tggtaagtca ggccctggag taagagagtt taatccaagt   7620
ggactgaagc tctgttaaat ctggacactc tttcagccct gtcccgggtg taccctagcc   7680
cttccccgag ccaagccagg aagaaagcca gagtcagctg ttctcagaac cctgtgggac   7740
cagaacagaa taacactaag acacctcctt ccctacctcc tcctcccctt tccctaaccc   7800
caggacgcgc atgcttggcg gctgcacaaa gtcgcgcgca ctcggggccg cgctcagcac   7860
cacggacagc ggcgactggg ggaggggcgg gcggcgtagc cgggccctc cccgcgccct   7920 gggcgggtcc ccgccgccct ccctagctcc tccgccacct cccgggttc gacgctctgt    7980 gctcttctgt tgcttttgcc tcaggtgctg ctgaggaagc ggaacgggac cccgagctgg   8040
cagctccggg ggaagatgca gagccgcagg ctgggccgtc tgcacgcggc tctccaagcc   8100
ccgccgcccc gggccacccc gccggccctc tgcctcgcat ggacctgcca cccgccgggc   8160 aaccccctacg ccacccaacc cgagcccgac cgagaccacg tcgccagcac caccaccgcc   8220
cgccgccggg ggcccccag gtaagtgctt cccttccccc tcgcccctct tgagggtcat    8280
gggtggacca ttcactcttc acttgagata aaagactgga agatggggttg tggaggccca   8340 aggccaccgg atcgcgctct atcatctttc tggccaccct catactcagg ccatggcaat   8400
aacgggccat ggtgtgtggc tttcctgtga ggagctacta gatggtggac cccctccttg   8460
tagtggtctg ctctatgggt gaacatgcga gagcggatgt ccgccttgcc ctccctctcc   8520
taaggttgct gaaaaacact gggcagctgg accgcgggac actcctgcgt ctgctgtgta   8580
ccagcgggtg gatgtatgtg tgggttgggt actggcaagg gtagtgggca ctggcagaag   8640
```

```
gagaggagca gctggcctga ggcccnctga gggtctgacg cagcagcggc gccactgagc   8700
cgggatgaga ggccgggtgg tgtggtgtgg aggtggaagg ttagggtact gcagggaact   8760
gttgggagta gaagggatgg catatttgca atgtgcgacc cataggtgtt tgcttagtga   8820
cagccaggtg gttcagggta tagcagcctc tggactgggt gggtgcgctg tgacagcaat   8880
gaagaatgaa agccagagtg gtacagacag tctccagctc cgggatgtac tcaggccagg   8940
ccactgggaa ggagaggatg tctaggaaga gtcacagttc ccagtcctga ctcctaacct   9000
cccaatgtct cccaggtgcc cccagccctg cttcaagaag gaaatgggct cactgctcgc   9060
gtggatgagg gtgtggagga gttcttctcc aaaaggctga tccagcagga tcacttgtga   9120
gtgagggtcg gttgactggg ggcggaggag ggtggaacat ccccgagttt cttcactcac   9180
tgatggttat tcctacagct gggccccaga ggaggatcca gccactgagg gtggtgccac   9240
tcctgtcccc cgcacacttc gaaagaagct gggtacgctc tttgccttta agaaacctcg   9300
ttcaacaagg ggtccgcgac ctgacctgga gaccagccct ggagcagcag ctcgagccag   9360
aaaatccaca cttggggatc tcctgcgacc accggcccgt ccaggccgtg gtgaggaacc   9420 tggagggcgcg gaaggcggca ccagcagccc tgaccctgct cgcagaaatc ggcctcggta   9480
cacgcgggaa agcaaggcct actccatgat cctgctacct gctgaggagg aagcagccgt   9540
gggtaccaga cctgataagg taaggccagg ggccgggggct gaggctcctc aggaacagag   9600
agcagtgggg ttctctcacc acttaggcat ctctgtcctc agaggcggcc tctgaacgg    9660 ggagacacag aactggctcc atcttttgag cagcgggtac aagtgatgct acagaggatc   9720
ggcgtgagcc gggccagtgg gggtgccgag agcaagagga agcaagtgag ttgggggtga   9780
actgcggggg caggtggcat gtggtaatct gtgggtgaca tatgtgacca agaagggaga   9840
aacacatggt gggaatagat ctaattatca gttacatgtt ctcatccctc aagaggcaag   9900
gaggagaact tcttccctc ttgcttctga cctggttcag atcttctagg gtatagggaa    9960 ctccttttc tgaagaagaa attaacagaa atttgacctt gttttacctg aaagttctcc   10020
aggaacttcc ttatccagat gccttatgtt ttttttttgt tttaatattt atgtgagtac   10080
actgtccctg ccttctgtct tcagacacac cagaaactag cattggatcc cattacagat   10140
agttgccggg agttgaactt gggtcctctg gaagagtagt cagtgctctt agctgctgag   10200
ccgtctctcc agtcccttta tccagattcc taatcccgct gtgagatctc acaggaactt   10260
ggtactggcc accttagacc tgttttcctt tgaagcctca cttggccatt gatttttatt   10320
ctctgactgt cgggtcatgt actggattat acaggctcct ttccagcctt ccctgacacc   10380
cttccatggt caccgggata acattactac aatcatggtc tttattagga actacacctc   10440
tgtatgccat ccatttaaat agcttttccag gaagaacaca tgcagtgaga cctggcctga   10500
atgtagtgat gttaaagtgt ggcaagtcat agaactaatt atctgctgga tgtggcggta   10560
atctcagcat tcagaaaact ggggcaggag gattgcaagt aagactagcc tgagttgtct   10620
acagcaagac tatctcaaaa gcaaagtcta cctgtcatga ccaacatgaa cattttgca    10680 tgttagctat ctgtctatcc cagactgtaa ggtcagaggg tggaaactgg ctttaccatg   10740
ctctggccag cctatgctat gcattctgta gctgggtttt aacaacatgg acagagacaa   10800
ggctagggtc agggcggcag ggctgctgcc tgactcatgt gtttcctaca gagtaaagac   10860
ggcgagatca agaaggcagg ctctgatggt gagtaggacc ccaccgggga caaggagata   10920
tatgttgggg aacaaggtgg cctcagataa cccctaaggc tccctcctc caccactaag    10980 gtctgacacc taagcctcta atccttcctt gcaggtgaca ttatggacag ttccacagag   11040
```

-continued

```
acccctccca tctcaatcaa gtcccgtacc cactctgtgt ctgctggtga gtgagggcca    11100
ctggatatgt taaaggaggt gcaagggttg ggaggggatc ggactgttgc tcagaaccat    11160
tccacagaca ggcttgggtg ttagctgaca ttgtcttctc tacccagatc cctcatgcag    11220
acctgggcca ggaggccagg ggcctgagtc tgccacctgg aagacattgg gacagcagct    11280
gaatgcagag ctcagaggcc gtggttgggg ccaacaggat ggtccagggc ccccctcccc    11340
atgtcccagc ccaagtcccc gaagaaccag ccccgcccca gacatcctga gtctcccaga    11400
ggacccctgc ttgggcccta ggaatgaagg taggtaggca ccccactcct aggctaggaa    11460
cccgactcat ctgggaaggc caaggtgggg aggcgaaggc tgggtgtggg cggagtatgg    11520
gaacgtcctc tgacatctcg gcctcctcta gatggccagc tgaggccgag gcctctttcg    11580
gcaggccggc gagcagtgtc tgtgcatgag gaccagctcc aggcccccgc gggtgaggga    11640
gacccctctg cctgtgcttg agtgcaggag aaaggggggag gtgggctcga tcggtcttgg    11700
tccttggaca gcgccacctc ctgaaggccc acctcagcta gggtgggagg cacttgctg    11760
gacaatctat gggcgtagca tgtgcatggt tttgcgtgca ctcaaggtgg accagagggt    11820
tggggacagc cagtgagttt tttctgtatc cttttagaa cggcccctcc ggctgcagcg    11880
ctcccctgtc ctcaagcgta ggccgaagct cgaggcaccc ccatccccaa gcttaggtga    11940
gagtgggcac gggccagctg ggatgctgat acgactgctc agtacaagcc tagcattgtt    12000
tctctccata acccttcaca ggctctggcc ttggatccaa gcctcttcct ccgtacccca    12060
cagaaccctc cagccctgag cggagccctc cctccccagc cacagaccaa agaggcggcg    12120
gccccaaccc ctgaatctct ctcctcctgc cgcatgaaat tatttatta aaaacttga    12180
atgaaa                                                               12186
```

<210> SEQ ID NO 8
<211> LENGTH: 1295
<212> TYPE: PRT
<213> ORGANISM: Mus musculus

<400> SEQUENCE: 8

```
Met Ala Gln Thr Pro Asp Asp Ile Ser Cys Glu Leu Arg Gly Glu Ile
1               5                   10                  15

Thr Arg Phe Leu Trp Pro Lys Glu Ala Glu Leu Leu Leu Lys Thr Trp
            20                  25                  30

Leu Pro Gln Glu Gly Ala Glu Gln Ser His Ile Leu Ala Leu Leu Arg
        35                  40                  45

Trp Arg Ala Tyr Leu Leu His Thr Cys Leu Pro Leu Arg Val Asp Cys
    50                  55                  60

Thr Phe Ser Tyr Leu Glu Val Gln Ala Met Ala Leu Gln Glu Thr Pro
65                  70                  75                  80

Pro Arg Val Thr Phe Glu Leu Glu Ser Leu Pro Glu Leu Val Leu Glu
                85                  90                  95

Phe Pro Cys Val Ala Ala Leu Glu Gln Leu Ala Gln His Val Ala Ala
            100                 105                 110

Ala Ile Lys Lys Val Phe Pro Arg Ser Thr Leu Gly Lys Leu Phe Arg
        115                 120                 125

Lys Pro Thr Pro Ser Ser Leu Leu Ala Arg Leu Glu Arg Ser His Pro
    130                 135                 140

Leu Glu Ser Thr Ile Pro Ser Ser Pro Cys Gly Gly Phe Leu Glu Thr
145                 150                 155                 160
```

-continued

```
Tyr Glu Ala Leu Cys Asp Tyr Asn Gly Phe Pro Phe Arg Glu Ile
            165                 170                 175
Gln Trp Asp Val Asp Thr Ile Tyr His Arg Gln Gly Cys Arg His Phe
        180                 185                 190
Cys Leu Gly Asp Phe Ser His Phe Gly Ser Arg Asp Leu Ala Leu Ser
        195                 200                 205
Val Ala Ala Leu Ser Tyr Asn Leu Trp Phe Arg Leu Ser Cys Glu
210                 215                 220
Asp Met Lys Leu Ser Leu Glu Val Ser Glu Gln Ile Leu His Met Thr
225                 230                 235                 240
Ser Gln Ser Ser Tyr Leu Glu Glu Leu Val Leu Glu Ala Cys Gly Leu
                245                 250                 255
Arg Gly Asp Phe Val Arg Leu Ala Gln Ala Leu Ala Gly His Phe
            260                 265                 270
Asn Ser Gly Leu Arg Glu Leu Ser Leu Ser Gly Asn Leu Leu Asp Asp
        275                 280                 285
Arg Gly Met Arg Ala Leu Gly Arg Ala Leu Ala Thr Asn Ala Thr Phe
        290                 295                 300
Asp Ser Thr Leu Thr His Leu Asp Leu Ser Gly Asn Pro Gly Ala Leu
305                 310                 315                 320
Gly Pro Ser Gln Asp Ser Gly Gly Leu Tyr Thr Phe Leu Ser Arg Pro
                325                 330                 335
Asn Val Leu Ala Tyr Leu Asn Leu Ala Gly Thr Asp Ala Thr Leu Gly
            340                 345                 350
Thr Leu Phe Thr Ala Leu Ala Gly Gly Cys Cys Ser Ser Leu Thr His
        355                 360                 365
Leu Glu Ala Ser Arg Asn Ile Phe Ser Arg Met Lys Ser Gln Ala Ala
    370                 375                 380
Pro Ala Ala Leu Gln Arg Phe Leu Gly Gly Thr Arg Met Leu Arg His
385                 390                 395                 400
Leu Gly Leu Ala Gly Cys Lys Leu Pro Pro Glu Ala Leu Arg Ala Leu
                405                 410                 415
Leu Glu Gly Leu Ala Leu Asn Thr Gln Ile His Asp Leu His Leu Asp
            420                 425                 430
Leu Ser Ala Cys Glu Leu Arg Ser Val Gly Ala Gln Val Ile Gln Asp
        435                 440                 445
Leu Val Cys Asp Ala Gly Ala Leu Ser Ser Leu Asp Leu Ser Asp Asn
    450                 455                 460
Gly Phe Gly Ser Asp Met Val Thr Leu Val Leu Ala Ile Gly Arg Ser
465                 470                 475                 480
Arg Ser Leu Lys His Val Ala Leu Gly Arg Asn Phe Asn Val Arg Cys
                485                 490                 495
Lys Glu Thr Leu Asp Asp Val Leu His Arg Ile Ala Gln Leu Met Gln
            500                 505                 510
Asp Asp Asp Cys Pro Leu Gln Ser Leu Ser Val Ala Glu Ser Arg Leu
        515                 520                 525
Lys Gln Gly Ala Ser Ile Leu Ile Arg Ala Leu Gly Thr Asn Pro Lys
    530                 535                 540
Leu Thr Ala Leu Asp Ile Ser Gly Asn Ala Ile Gly Asp Ala Gly Ala
545                 550                 555                 560
Lys Met Leu Ala Lys Ala Leu Arg Val Asn Thr Arg Leu Arg Ser Val
                565                 570                 575
Ile Trp Asp Arg Asn Asn Thr Ser Ala Leu Gly Leu Leu Asp Val Ala
```

-continued

```
                580                 585                 590
    Gln Ala Leu Glu Gln Asn His Ser Leu Lys Ser Met Pro Leu Pro Leu
                    595                 600                 605
    Asn Asp Val Thr Gln Ala His Arg Ser Arg Pro Glu Leu Thr Thr Arg
                610                 615                 620
    Ala Val His Gln Ile Gln Ala Cys Leu Trp Arg Asn Asn Gln Val Asp
    625                 630                 635                 640
    Ser Thr Ser Asp Leu Lys Pro Cys Leu Gln Pro Leu Gly Leu Ile Ser
                    645                 650                 655
    Asp His Ser Glu Gln Glu Val Asn Glu Leu Cys Gln Ser Val Gln Glu
                660                 665                 670
    His Met Glu Leu Leu Gly Cys Gly Ala Gly Pro Gln Gly Glu Val Ala
                    675                 680                 685
    Val His Gln Ala Glu Asp Ala Ile Gln Asn Ala Asn Phe Ser Leu Ser
                690                 695                 700
    Ile Leu Pro Ile Leu Tyr Glu Ala Gly Arg Ser Pro Ser His His Trp
    705                 710                 715                 720
    Gln Leu Gln Gln Lys Leu Glu Ser Leu Leu Gly Gln Val Gly Glu Ile
                    725                 730                 735
    Cys Arg Gln Asp Ile Gln Asp Phe Thr Gln Thr Thr Leu Asp Thr Thr
                740                 745                 750
    Arg Ser Leu Cys Pro Gln Met Leu Gln Thr Pro Gly Trp Arg Lys Gln
                    755                 760                 765
    Leu Glu Gly Val Leu Val Gly Ser Gly Leu Pro Glu Leu Leu Pro
                770                 775                 780
    Glu His Leu Leu Gln Asp Ala Phe Ser Arg Leu Arg Asp Met Arg Leu
    785                 790                 795                 800
    Ser Ile Thr Gly Thr Leu Ala Glu Ser Ile Val Ala Gln Ala Leu Ala
                    805                 810                 815
    Gly Leu His Ala Ala Arg Asp Arg Leu Val Glu Arg Leu Thr Gln Gln
                820                 825                 830
    Ala Pro Val Thr Met Ala Pro Ala Val Pro Pro Leu Gly Gly Asn Glu
                    835                 840                 845
    Leu Ser Pro Leu Glu Thr Gly Gly Leu Glu Glu Leu Phe Phe Pro Thr
                850                 855                 860
    Glu Lys Glu Glu Glu Arg Glu Lys Val Leu Leu Arg Lys Arg Asn Gly
    865                 870                 875                 880
    Thr Pro Ser Trp Gln Leu Arg Gly Lys Met Gln Ser Arg Arg Leu Gly
                    885                 890                 895
    Arg Leu His Ala Val Ala Glu Lys His Trp Ala Ala Gly Pro Arg Asp
                900                 905                 910
    Thr Pro Ala Ser Ala Val Tyr Gln Arg Val Asp Val Cys Val Gly Trp
                    915                 920                 925
    Val Pro Pro Ala Leu Leu Gln Glu Gly Asn Gly Leu Thr Ala Arg Val
                930                 935                 940
    Asp Glu Gly Val Glu Glu Phe Phe Ser Lys Arg Leu Ile Gln Gln His
    945                 950                 955                 960
    Phe Trp Ala Pro Glu Glu Asp Pro Ala Thr Glu Gly Gly Ala Thr Pro
                    965                 970                 975
    Val Pro Arg Thr Leu Arg Lys Lys Leu Gly Thr Leu Phe Ala Phe Lys
                980                 985                 990
    Lys Pro Arg Ser Thr Arg Gly Pro  Arg Pro Asp Leu Glu  Thr Ser Pro
                    995                 1000                1005
```

Gly Ala Ala Ala Arg Ala Arg Lys Ser Thr Leu Gly Asp Leu Leu
    1010                1015                1020

Arg Pro Pro Ala Arg Pro Gly Arg Gly Glu Glu Pro Gly Gly Ala
    1025                1030                1035

Glu Gly Gly Thr Ser Ser Pro Asp Pro Ala Arg Arg Asn Arg Pro
    1040                1045                1050

Arg Tyr Thr Arg Glu Ser Lys Ala Tyr Ser Met Ile Leu Leu Pro
    1055                1060                1065

Ala Glu Glu Ala Ala Val Gly Thr Arg Pro Asp Lys Arg Arg
    1070                1075                1080

Pro Leu Glu Arg Gly Asp Thr Glu Leu Ala Pro Ser Phe Glu Gln
    1085                1090                1095

Arg Val Gln Val Met Leu Gln Arg Ile Gly Val Ser Arg Ala Ser
    1100                1105                1110

Gly Gly Ala Glu Ser Lys Arg Lys Gln Ser Lys Asp Gly Glu Ile
    1115                1120                1125

Lys Lys Ala Gly Ser Asp Gly Asp Ile Met Asp Ser Ser Thr Glu
    1130                1135                1140

Thr Pro Pro Ile Ser Ile Lys Ser Arg Thr His Ser Val Ser Ala
    1145                1150                1155

Asp Pro Ser Cys Arg Pro Gly Pro Gly Gly Gln Gly Pro Glu Ser
    1160                1165                1170

Ala Thr Trp Lys Thr Leu Gly Gln Gln Leu Asn Ala Glu Leu Arg
    1175                1180                1185

Gly Arg Gly Trp Gly Gln Gln Asp Gly Pro Gly Pro Pro Ser Pro
    1190                1195                1200

Cys Pro Ser Pro Ser Pro Arg Arg Thr Ser Pro Ala Pro Asp Ile
    1205                1210                1215

Leu Ser Leu Pro Glu Asp Pro Cys Leu Gly Pro Arg Asn Glu Glu
    1220                1225                1230

Arg Pro Leu Arg Leu Gln Arg Ser Pro Val Leu Lys Arg Arg Pro
    1235                1240                1245

Lys Leu Glu Ala Pro Pro Ser Pro Ser Leu Gly Ser Gly Leu Gly
    1250                1255                1260

Ser Lys Pro Leu Pro Pro Tyr Pro Thr Glu Pro Ser Ser Pro Glu
    1265                1270                1275

Arg Ser Pro Pro Ser Pro Ala Thr Asp Gln Arg Gly Gly Gly Pro
    1280                1285                1290

Asn Pro
    1295

<210> SEQ ID NO 9
<211> LENGTH: 3295
<212> TYPE: DNA
<213> ORGANISM: Homo sapiens

<400> SEQUENCE: 9
ccgccagccc cgccagtccc cgcgcagtcc ccgcgcagtc cccgcgcagt cccagcgcca      60
ccgggcagca gcggcgccgt gctcgctcca gggcgcaacc atgtcgccat ttcttcggat     120
tggcttgtcc aactttgact gcgggtcctg ccagtcttgt cagggcgagg ctgttaaccc     180
ttactgtgct gtgctcgtca aagagtatgt cgaatcagag aacgggcaga tgtatatcca     240
gaaaaagcct accatgtacc caccctggga cagcactttt gatgcccata tcaacaaggg     300

```
aagagtcatg cagatcattg tgaaaggcaa aaacgtggac ctcatctctg aaaccaccgt    360
ggagctctac tcgctggctg agaggtgcag gaagaacaac gggaagacag aaatatggtt    420
agagctgaaa cctcaaggcc gaatgctaat gaatgcaaga tactttctgg aaatgagtga    480
cacaaaggac atgaatgaat ttgagacgga aggcttcttt gctttgcatc agcgccgggg    540
tgccatcaag caggcaaagg tccaccacgt caagtgccac gagttcactg ccaccttctt    600
cccacagccc acattttgct ctgtctgcca cgagtttgtc tggggcctga caaacaggg     660 ctaccagtgc cgacaatgca atgcagcaat tcacaagaag tgtattgata agttatagc     720 aaagtgcaca ggatcagcta tcaatagccg agaaaccatg ttccacaagg agagattcaa    780
aattgacatg ccacacagat ttaaagtcta caattacaag agcccgacct tctgtgaaca    840
ctgtgggacc ctgctgtggg gactggcacg gcaaggactc aagtgtgatg catgtggcat    900
gaatgtgcat catagatgcc agacaaaggt ggccaacctt tgtggcataa accagaagct    960
aatggctgaa gcgctggcca tgattgagag cactcaacag gctcgctgct taagagatac   1020
tgaacagatc ttcagagaag gtccggttga aattggtctc ccatgctcca tcaaaaatga   1080
agcaaggccg ccatgtttac cgacaccggg aaaagagag cctcagggca tttcctggga    1140
gtctccgttg gatgaggtgg ataaaatgtg ccatcttcca gaacctgaac tgaacaaaga   1200
aagaccatct ctgcagatta aactaaaaat tgaggatttt atcttgcaca aaatgttggg   1260
gaaaggaagt tttggcaagg tcttcctggc agaattcaag aaaaccaatc aatttttcgc   1320
aataaaggcc ttaagaaaag atgtggtctt gatggacgat gatgttgagt gcacgatggt   1380
agagaagaga gttctttcct tggcctggga gcatccgttt ctgacgcaca tgttttgtac   1440
attccagacc aaggaaaacc tctttttttgt gatggagtac ctcaacggag gggacttaat   1500
gtaccacatc caaagctgcc acaagttcga ccttccaga gcgacgtttt atgctgctga    1560
aatcattctt ggtctgcagt tccttcattc caaaggaata gtctacaggg acctgaagct   1620
agataacatc ctgttagaca aagatggaca tatcaagatc gcggattttg aatgtgcaa    1680 ggagaacatg ttaggagatg ccaagacgaa taccttctgt gggacacctg actacatcgc   1740
cccagagatc ttgctgggtc agaaatacaa ccactctgtg gactggtggt ccttcggggt   1800
tctcctttat gaaatgctga ttggtcagtc gcctttccac gggcaggatg aggaggagct   1860
cttccactcc atccgcatgg acaatccctt ttacccacgg tggctggaga aggaagcaaa   1920
ggaccttctg gtgaagctct tcgtgcgaga acctgagaag aggctgggcg tgaggggaga   1980
catccgccag caccctttgt ttcgggagat caactgggag gaacttgaac ggaaggagat   2040
tgacccaccg ttccggccga aagtgaaatc accatttgac tgcagcaatt tcgacaaaga   2100
attcttaaac gagaagcccc ggctgtcatt tgccgacaga gcactgatca acagcatgga   2160
ccagaatatg ttcaggaact tttccttcat gaaccccggg atggagcggc tgatatcctg   2220
aatcttgccc ctccagagac aggaaagaat tgccttctc cctgggaact ggttcaagag    2280
acactgcttg ggttccttttt tcaacttgga aaagaaaga aacactcaac aataaagact   2340
gagacccgtt cgcccccatg tgactttat ctgtagcaga aaccaagtct acttcactaa    2400
tgacgatgcc gtgtgtctcg tctcctgaca tgtctcacag acgctcctga agttaggtca   2460
ttactaacca tagttattta cttgaaagat gggtctccgc acttggaaag gtttcaagac   2520
ttgatactgc aataaattat ggctcttcac ctgggcgcca actgctgatc aatgaaatgc   2580
ttgttgaatc aggggcaaac ggagtacaga cgtctcaaga ctgaaacggc cccattgcct   2640
ggtctagtag cggatctcac tcagccgcag acaagtaatc actaacccgt tttattctat   2700
```

```
tcctatctgt ggatgtgtaa atggctgggg ggccagccct ggataggttt ttatgggaat    2760
tctttacaat aaacatagct tgtaacttga gatctacaaa tccattcatc ctgattgggc    2820
atgaaatcca tggtcaagag gacaagtgga aagtgagagg gaaggtttgc tagacacctt    2880
cgcttgttat cttgtcaaga tagaaaagat agtatcattt cacccttgcc agtaaaaacc    2940
tttccatcca cccattctca gcagactcca gtattggcac agtcactcac tgccattctc    3000
acactataac aagaaaagaa atgaagtgca taagtctcct gggaaaagaa ccttaacccc    3060
ttctcgtgcc atgactggtg atttcatgac tcataagccc ctccgtaggc atcattcaag    3120
atcaatggcc catgcatgct gtttgcagca gtcaattgag ttgaattaga attccaacca    3180
tacattttaa aggtatttgt gctgtgtgta tattttgata aaatgttgtg acttcatggc    3240
aaacaggtgg atgtgtaaaa atggaataaa aaaaaaaaaa gagtcaaaaa aaaaa         3295
```

<210> SEQ ID NO 10
<211> LENGTH: 706
<212> TYPE: PRT
<213> ORGANISM: Homo sapiens

<400> SEQUENCE: 10

```
Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270
```

```
Cys Gln Thr Lys Val Ala Asn Leu Cys Gly Ile Asn Gln Lys Leu Met
        275                 280                 285
Ala Glu Ala Leu Ala Met Ile Glu Ser Thr Gln Gln Ala Arg Cys Leu
    290                 295                 300
Arg Asp Thr Glu Gln Ile Phe Arg Glu Gly Pro Val Glu Ile Gly Leu
305                 310                 315                 320
Pro Cys Ser Ile Lys Asn Glu Ala Arg Pro Pro Cys Leu Pro Thr Pro
                325                 330                 335
Gly Lys Arg Glu Pro Gln Gly Ile Ser Trp Glu Ser Pro Leu Asp Glu
            340                 345                 350
Val Asp Lys Met Cys His Leu Pro Glu Pro Glu Leu Asn Lys Glu Arg
            355                 360                 365
Pro Ser Leu Gln Ile Lys Leu Lys Ile Glu Asp Phe Ile Leu His Lys
        370                 375                 380
Met Leu Gly Lys Gly Ser Phe Gly Lys Val Phe Leu Ala Glu Phe Lys
385                 390                 395                 400
Lys Thr Asn Gln Phe Phe Ala Ile Lys Ala Leu Lys Lys Asp Val Val
                405                 410                 415
Leu Met Asp Asp Asp Val Glu Cys Thr Met Val Glu Lys Arg Val Leu
            420                 425                 430
Ser Leu Ala Trp Glu His Pro Phe Leu Thr His Met Phe Cys Thr Phe
            435                 440                 445
Gln Thr Lys Glu Asn Leu Phe Phe Val Met Glu Tyr Leu Asn Gly Gly
        450                 455                 460
Asp Leu Met Tyr His Ile Gln Ser Cys His Lys Phe Asp Leu Ser Arg
465                 470                 475                 480
Ala Thr Phe Tyr Ala Ala Glu Ile Ile Leu Gly Leu Gln Phe Leu His
                485                 490                 495
Ser Lys Gly Ile Val Tyr Arg Asp Leu Lys Leu Asp Asn Ile Leu Leu
            500                 505                 510
Asp Lys Asp Gly His Ile Lys Ile Ala Asp Phe Gly Met Cys Lys Glu
            515                 520                 525
Asn Met Leu Gly Asp Ala Lys Thr Asn Thr Phe Cys Gly Thr Pro Asp
        530                 535                 540
Tyr Ile Ala Pro Glu Ile Leu Leu Gly Gln Lys Tyr Asn His Ser Val
545                 550                 555                 560
Asp Trp Trp Ser Phe Gly Val Leu Leu Tyr Glu Met Leu Ile Gly Gln
                565                 570                 575
Ser Pro Phe His Gly Gln Asp Glu Glu Glu Leu Phe His Ser Ile Arg
            580                 585                 590
Met Asp Asn Pro Phe Tyr Pro Arg Trp Leu Glu Lys Glu Ala Lys Asp
            595                 600                 605
Leu Leu Val Lys Leu Phe Val Arg Glu Pro Glu Lys Arg Leu Gly Val
        610                 615                 620
Arg Gly Asp Ile Arg Gln His Pro Leu Phe Arg Glu Ile Asn Trp Glu
625                 630                 635                 640
Glu Leu Glu Arg Lys Glu Ile Asp Pro Pro Phe Arg Pro Lys Val Lys
                645                 650                 655
Ser Pro Phe Asp Cys Ser Asn Phe Asp Lys Glu Phe Leu Asn Glu Lys
            660                 665                 670
Pro Arg Leu Ser Phe Ala Asp Arg Ala Leu Ile Asn Ser Met Asp Gln
        675                 680                 685
```

```
Asn Met Phe Arg Asn Phe Ser Phe Met Asn Pro Gly Met Glu Arg Leu
        690                 695                 700

Ile Ser
705

<210> SEQ ID NO 11
<211> LENGTH: 3313
<212> TYPE: DNA
<213> ORGANISM: Mus musculus

<400> SEQUENCE: 11
cttgggtcgc caggcccgcg ccagtccccg ccatccgagc aacagcggcg ctgctctggg       60
accgcggccg cgacaccagg gaacaaccat gtcaccgttt cttcgaatcg gtttatccaa      120
ctttgactgt gggacctgcc aagcttgtca gggagaggca gtgaacccct actgcgctgt      180
gcttgtcaaa gagtatgtgg aatcagaaaa tgggcagatg tacatccaga aaaagccaac      240
catgtaccca ccttgggaca gcaccttga cgcccacatt aacaagggaa gggtgatgca      300
gatcatcgtg aagggcaaga atgtagacct catctcagaa acaaccgtgg aactctactc      360
cctggcggag agatgccgca gaacaatgg gcggacagaa atatggttag agctgaaacc      420
tcaaggccga atgctaatga atgcaagata ctttctggaa atgagtgaca caaaggacat      480
gagtgagttt gagaatgaag gattctttgc actgcatcag cgccgaggag ccatcaaaca      540
ggccaaagtc caccatgtca agtgtcacga gttcacggcc accttttttcc ctcaacccac      600 attttgctct gtctgccatg aatttgtctg gggcctgaac aagcagggtt accagtgccg      660
acagtgtaat gcagcgattc acaagaagtg cattgataaa gtgatagcca agtgcacagg      720
atccgcaatc aatagccgag aaaccatgtt ccataaggag agattcaaga tcgacatgcc      780
acacagattc aaagtctaca actacaagag tccaaccttc tgtgagcact gtggtaccct      840
gctctggggg ctggcgaggc aaggactcaa atgtgatgca tgtggcatga acgtccacca      900
ccgatgccag acaaaggttg ccaatctttt tggtataaac cagaagctaa tggctgaagc      960
actagcgatg attgaaagca cccaacaggc tcgctcctta cgagattcag aacacatctt     1020
ccgagaaggc ccagttgaaa ttggtctccc atgctccacc aaaaacgaaa ccaggccacc     1080
atgcgtacca acacctggga aaagagaacc ccagggcatt tcctgggatt ccccttttgga    1140 tgggtcaaat aaatcggccg gtcctcctga acccgaagtg agcatgcgca ggacttcact     1200
gcagctgaaa ctgaagatcg atgacttcat cctgcacaag atgttgggaa aggaagtttt     1260
tggcaaggtc ttcctggcag agttcaagag aaccaatcag tttttcgcaa taaaagcctt     1320
aaagaaagat gtggtgttga tggatgatga cgtcgagtgt acaatggtgg aaaagagggt     1380
tctgtccttg gcatgggagc atccatttct aacacacatg ttctgcacat tccagaccaa     1440
ggaaaatctc tttttcgtga tggagtatct caatggaggc gacttaatgt accacatcca     1500
aagttgccac aaatttgatc tttccagagc cacgttttat gctgctgagg tcatccttgg     1560
tctgcagttc cttcattcca aaggaattgt ctacaggac ctgaagcttg ataatatcct     1620
gttagacaga gatggacata tcaaaatagc agactttggg atgtgcaaag aacatgct     1680 aggagatgcg aagacaaata ctttctgtgg aactcctgac tacattgctc ggagatctt     1740 gctgggtcag aagtacaacc attccgtcga ctggtggtcc ttcggggtgc tcgtttatga     1800
gatgctgatt ggccagtccc ccttccacgg gcaggacgag gaggagctgt tccactccat     1860
ccgcatggac aaccccttct acccgaggtg gctcgaaagg gaggccaagg accttctagt     1920
gaagcttttt gtgagagaac ctgagaagag gctgggagtg agaggagaca tccgccagca     1980
```

```
tcctttgttt cgagagatca actgggaaga gcttgaaagg aaagagattg acccacccttt    2040 cagaccaaaa gtgaaatcac catatgactg tagcaatttc gacaaggaat tcctaagtga    2100
gaaaccccgg ctatcattcg ccgacagagc actcatcaac agcatggacc agaacatgtt    2160
cagcaacttt tccttcatta acccagggat ggagactctc atttgctcct gaacctcatc    2220
tgtctccaga ctggaaggga tttgccttct ctctgggaac tggttcaagt aacacttctg    2280
ggggtggggg tctcttttc acgttagaga agaaaagaaa cactgcaaag gcagggagga    2340
ctgctgagct ccttgtgtga cttgttacct acagcacaaa ccacgcctac ttcactaatg    2400
acatcatccc taatgacatc atcccgttat atctcctgga atctctcaca gcagcccttg    2460
aagttagatc attattaact ctagtcattt acttgaaaga tggttcccga tgctgtgaaa    2520
gattcgaaat gcagttctgc tcttgcccta gacaacagct gctggttggt gatgaaccaa    2580
ggcgcaagtg aacagatttt ctcaagactg gagcagtgat cgcctgttat agaagtcaat    2640
tccactcaac cacagagaag gaaccactaa gccacgttga tgtgtgcatg tctgtggaaa    2700
tgtcgatgac agaagggagg gaaaggggaa gctctgagca gattgtaatg ggaagctctc    2760
caataaacat agcatgaaac ttgaaattta caaatctgtt cattctggct agccccaaaa    2820
ttcccaaggc agaggaaagt aaagggcagt gagcttagca gagcccttg tcgccaacag    2880 ggaagggtaa ggatgtcgcc tacgtggaac atcttataca cacagaagga agtataacc    2940 aacaagggca gggtggttta cagctgccaa tcaaacctgc cctccccct ctgttctcag    3000 ttgatctctc tgtcagcgta ggtaggcact cattaccatc ctcccatcat acaagaaata    3060
aaatgcatga ctcttctaag ataaagaaaa ccaatcccctt atcacgttgt tcccagtgat    3120
ttgatggcaa ataagtccct ccttaggcat cctgcaagac aacccaaccc atgcatgcta    3180
tttgcagtag tcagtcctgt tgagttagag tcctaactat acacaatatc gtgcgatgtt    3240
tatatatgtt gatgagatgt tgtgatgata acgtggatat gtaaaaggga ataaaagaag    3300
aaagaaagat gcc                                                      3313
```

<210> SEQ ID NO 12
<211> LENGTH: 707
<212> TYPE: PRT
<213> ORGANISM: Mus musculus

<400> SEQUENCE: 12

```
Met Ser Pro Phe Leu Arg Ile Gly Leu Ser Asn Phe Asp Cys Gly Thr
1               5                   10                  15

Cys Gln Ala Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Arg Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125
```

-continued

```
Lys Asp Met Ser Glu Phe Glu Asn Glu Gly Phe Phe Ala Leu His Gln
130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Ser Leu
290                 295                 300

Arg Asp Ser Glu His Ile Phe Arg Glu Gly Pro Val Glu Ile Gly Leu
305                 310                 315                 320

Pro Cys Ser Thr Lys Asn Glu Thr Arg Pro Pro Cys Val Pro Thr Pro
                325                 330                 335

Gly Lys Arg Glu Pro Gln Gly Ile Ser Trp Asp Ser Pro Leu Asp Gly
            340                 345                 350

Ser Asn Lys Ser Ala Gly Pro Pro Glu Pro Glu Val Ser Met Arg Arg
        355                 360                 365

Thr Ser Leu Gln Leu Lys Leu Lys Ile Asp Asp Phe Ile Leu His Lys
370                 375                 380

Met Leu Gly Lys Gly Ser Phe Gly Lys Val Phe Leu Ala Glu Phe Lys
385                 390                 395                 400

Arg Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
450                 455                 460

Asp Leu Met Tyr His Ile Gln Ser Cys His Lys Phe Asp Leu Ser Arg
465                 470                 475                 480

Ala Thr Phe Tyr Ala Ala Glu Val Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Arg Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
530                 535                 540

Tyr Ile Ala Pro Glu Ile Leu Leu Gly Gln Lys Tyr Asn His Ser Val
```

```
            545                 550                 555                 560
Asp Trp Trp Ser Phe Gly Val Leu Val Tyr Glu Met Leu Ile Gly Gln
                565                 570                 575

Ser Pro Phe His Gly Gln Asp Glu Glu Leu Phe His Ser Ile Arg
            580                 585                 590

Met Asp Asn Pro Phe Tyr Pro Arg Trp Leu Glu Arg Glu Ala Lys Asp
        595                 600                 605

Leu Leu Val Lys Leu Phe Val Arg Glu Pro Glu Lys Arg Leu Gly Val
    610                 615                 620

Arg Gly Asp Ile Arg Gln His Pro Leu Phe Arg Glu Ile Asn Trp Glu
625                 630                 635                 640

Glu Leu Glu Arg Lys Glu Ile Asp Pro Pro Phe Arg Pro Lys Val Lys
            645                 650                 655

Ser Pro Tyr Asp Cys Ser Asn Phe Asp Lys Glu Phe Leu Ser Glu Lys
        660                 665                 670

Pro Arg Leu Ser Phe Ala Asp Arg Ala Leu Ile Asn Ser Met Asp Gln
    675                 680                 685

Asn Met Phe Ser Asn Phe Ser Phe Ile Asn Pro Gly Met Glu Thr Leu
690                 695                 700

Ile Cys Ser
705

<210> SEQ ID NO 13
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 13
ccagagagag gaagccgaa                                                19

<210> SEQ ID NO 14
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 14
aggaagagau ggcucguca                                                19

<210> SEQ ID NO 15
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 15
gucuugaccu ugaacggaa                                                19

<210> SEQ ID NO 16
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 16
aagcaggagu caaacgagu                                                19
```

```
<210> SEQ ID NO 17
<211> LENGTH: 13
<212> TYPE: PRT
<213> ORGANISM: Artificial Sequence
<220> FEATURE:
<223> OTHER INFORMATION: synthetic oligopeptide

<400> SEQUENCE: 17

Ile Gly Val Ser Arg Gly Ser Gly Gly Ala Glu Gly Lys
1               5                   10
```